US009580501B2

(12) United States Patent
Ariaans et al.

(10) Patent No.: US 9,580,501 B2
(45) Date of Patent: Feb. 28, 2017

(54) ANTI-TNF ALPHA MONOCLONAL SECRETORY IGA ANTIBODIES AND METHODS FOR TREATING INFLAMMATORY DISEASES

(71) Applicant: Synthon Biopharmaceuticals B.V., Nijmegen (NL)

(72) Inventors: Gerardus Joseph Andreas Ariaans, Nijmegen (NL); Frans van Dalen, Nijmegen (NL); Declan Thomas Nolan, Nijmegen (NL)

(73) Assignee: Synthon Biopharmaceuticals B.V., Numegen (NL)

( * ) Notice: Subject to any disclaimer, the term of this patent is extended or adjusted under 35 U.S.C. 154(b) by 0 days.

(21) Appl. No.: 14/365,839

(22) PCT Filed: Dec. 14, 2012

(86) PCT No.: PCT/EP2012/075671
§ 371 (c)(1),
(2) Date: Jun. 16, 2014

(87) PCT Pub. No.: WO2013/087912
PCT Pub. Date: Jun. 20, 2013

(65) Prior Publication Data
US 2014/0356357 A1 Dec. 4, 2014

Related U.S. Application Data

(60) Provisional application No. 61/576,727, filed on Dec. 16, 2011, provisional application No. 61/576,922, filed on Dec. 16, 2011.

(51) Int. Cl.
C07K 16/24 (2006.01)
C12N 15/82 (2006.01)
A61K 9/00 (2006.01)
A61K 39/00 (2006.01)

(52) U.S. Cl.
CPC .......... *C07K 16/241* (2013.01); *A61K 9/0053* (2013.01); *C07K 16/244* (2013.01); *C12N 15/8258* (2013.01); *A61K 39/00* (2013.01); *A61K 2039/505* (2013.01); *A61K 2039/54* (2013.01); *C07K 2317/13* (2013.01); *C07K 2317/24* (2013.01); *C07K 2317/41* (2013.01); *C07K 2317/565* (2013.01); *C07K 2317/76* (2013.01)

(58) Field of Classification Search
CPC ................. A61K 9/0053; A61K 39/00; A61K 2039/505; A61K 2039/54; C07K 16/241; C07K 2317/13; C07K 2317/24; C07K 2317/41; C07K 2317/76; C07K 2317/565
See application file for complete search history.

(56) References Cited

U.S. PATENT DOCUMENTS

| | | |
|---|---|---|
| 4,771,002 A | 9/1988 | Gelvin |
| 5,075,236 A | 12/1991 | Yone et al. |
| 5,428,147 A | 6/1995 | Barker et al. |
| 5,605,690 A | 2/1997 | Jacobs et al. |
| 5,656,272 A | 8/1997 | Le et al. |
| 5,919,452 A | 7/1999 | Le et al. |
| 6,040,498 A | 3/2000 | Stomp et al. |
| 6,090,382 A | 7/2000 | Salfeld et al. |
| 6,451,982 B1 | 9/2002 | Chou et al. |
| 6,790,444 B2 | 9/2004 | Le et al. |
| 6,902,724 B1 | 6/2005 | Parekh et al. |
| 6,902,734 B2 | 6/2005 | Giles-Komar et al. |
| 6,914,128 B1 | 7/2005 | Salfeld et al. |
| 7,012,135 B2 | 3/2006 | Athwal et al. |
| 7,147,854 B2 | 12/2006 | Ye |
| 7,161,064 B2 | 1/2007 | Stomp et al. |
| 7,176,024 B2 | 2/2007 | Branson et al. |
| 7,186,820 B2 | 3/2007 | Athwal et al. |
| 7,622,573 B2 | 11/2009 | Dickey et al. |
| 7,632,983 B2 | 12/2009 | Dickey et al. |
| 7,883,704 B2 | 2/2011 | Salfeld et al. |
| 7,884,264 B2 | 2/2011 | Dickey et al. |
| 8,034,916 B2 | 10/2011 | Dickey et al. |
| 2009/0060921 A1 | 3/2009 | Dickey et al. |
| 2009/0214528 A1 | 8/2009 | Dorai et al. |
| 2010/0209966 A1 | 8/2010 | Everett et al. |
| 2012/0190004 A1 | 7/2012 | Parsons et al. |
| 2014/0359902 A1 | 12/2014 | Ariaans et al. |
| 2015/0010544 A1 | 1/2015 | Ariaans et al. |
| 2015/0166649 A1 | 6/2015 | Ariaans et al. |

FOREIGN PATENT DOCUMENTS

| | | |
|---|---|---|
| EP | 0449769 B1 | 12/1993 |
| EP | 0932415 A1 | 8/1999 |
| EP | 0602126 B1 | 3/2003 |
| EP | 1309692 B1 | 5/2009 |
| EP | 1313769 B2 | 11/2011 |

(Continued)

OTHER PUBLICATIONS

Chan AC, et al. Nature Reviews Immunology. 10(5):301-316, May 5, 2010.*
Worledge KL, et al. Digestive Diseases and Sciences. 45(12):2298-2305, Dec. 1, 2000.*
Berdoz J, et al. Proc. Natl. Acad. Sci. 96(6):3029-3034, Mar. 16, 1999.*
Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Akdis, C.A., "Therapies for Allergic Inflammation: Refining Strategies to Induce Tolerance," Nature Medicine 18(5):736-749, Nature Publishing Company, United States (2012).

(Continued)

*Primary Examiner* — Robert Landsman
(74) *Attorney, Agent, or Firm* — Sterne Kessler Goldstein & Fox

(57) ABSTRACT

A monoclonal secretory IgA antibody, which binds to and neutralizes human TNFα. The secretory antibody is useful in treating a variety of inflammatory conditions in humans.

21 Claims, 17 Drawing Sheets

(56) References Cited

FOREIGN PATENT DOCUMENTS

| | | |
|---|---|---|
| EP | 0783893 B1 | 4/2012 |
| EP | 1776142 B3 | 6/2015 |
| WO | WO-8907452 A1 | 8/1989 |
| WO | WO-9216553 A1 | 10/1992 |
| WO | WO-9222653 A1 | 12/1992 |
| WO | WO-9729131 A1 | 8/1997 |
| WO | WO-9949024 A2 | 9/1999 |
| WO | WO-2005007699 A2 | 1/2005 |
| WO | WO-2005035768 A1 | 4/2005 |
| WO | WO-2007028106 A2 | 3/2007 |
| WO | WO-2007084672 A2 | 7/2007 |
| WO | WO-2007084922 A2 | 7/2007 |
| WO | WO-2007084926 A2 | 7/2007 |
| WO | WO-2007124186 A2 | 11/2007 |
| WO | WO-2009086003 A1 | 7/2009 |
| WO | WO-2011/047238 A1 | 4/2011 |
| WO | WO 2011/047328 * | 4/2011 |
| WO | WO-2012162367 A1 | 11/2012 |
| WO | WO-2013087911 A1 | 6/2013 |
| WO | WO-2013087913 A1 | 6/2013 |
| WO | WO-2013087914 A1 | 6/2013 |

OTHER PUBLICATIONS

Bakker, H., et al., "An Antibody Produced in Tobacco Expressing a Hybrid β-1,4-galactosyltransferase is Essentially Devoid of Plant Carbohydrate Epitopes," Proceedings of the National Academy of Sciences USA 103(20):7577-7582, National Academy of Sciences, United States (2006).

Berdoz, J., et al., "In Vitro Comparison of the Antigen-binding and Stability Properties of the Various Molecular Forms of IgA Antibodies Assembled and Produced in CHO Cells," Proceedings of the National Academy of Sciences USA 96(6):3029-3034, National Academy of Sciences, United States (1999).

Berdoz, J. and Corthesy, B., "Human Polymeric IgA is Superior to IgG and Single-chain Fv of the Same Monoclonal Specificity to Inhibit Urease Activity Associated with *Helicobacter Pylori*," Molecular Immunology 41(10):1013-1022, Elsevier, Netherlands (2004).

Beyer, T., et al., "Serum-free Production and Purification of Chimeric IgA Antibodies," Journal of Immunological Methods 346(1-2):26-37, Elsevier, Netherlands (2009).

Brooks, D., et al., "Phase Ia Trial of Murine Immunoglobulin A Antitransferrin Receptor Antibody 42/6," Clinical Cancer Research 1(11):1259-1265, American Association for Cancer Research, United States (1995).

Brown, M., et al., "Tolerance to Single, but Not Multiple, Amino Acid Replacements in Antibody$V_H$ CDR2: A Means of Minimizing B Cell Wastage from Somatic Hypermutation?," Journal of Immunology 156(9):3285-3291, American Association of Immunologists, United States (1996).

Carter, P., et al., "Humanization of an Anti-p185$^{HER2}$ Antibody for Human Cancer Therapy," Proceedings of the National Academy of Sciences USA 89(10):4285-4289, National Academy of Sciences, United States (1992).

Chan, A.C. and Carter, P.J., "Therapeutic Antibodies for Autoimmunity and Inflammation," Nature Reviews Immunology 10(5):301-316, Macmillan Publishers Limited, England (2010).

Chintalacharuvu, K.R. and Morrison, S.L., "Production of Secretory Immunoglobulin A by a Single Mammalian Cell," Proceedings of the National Academy of Sciences USA 94(12):6364-6368, National Academy of Sciences, United States (1997).

Chintalacharuvu, K.R., et al., "Divergence of Human α-chain Constant Region Gene Sequences: A Novel Recombinant α 2 Gene," Journal of Immunology 152(11):5299-5304, American Association of Immunologists, United States (1994).

Corthesy, B., "Recombinant Immunoglobulin A: Powerful Tools for Fundamental and Applied Research," Trends in Biotechnology 20(2):65-71, Elsevier Science Publishers, England (2002).

Cox, K.M., et al., "Glycan Optimization of a Human Monoclonal Antibody in the Aquatic Plant Lemna Minor," Nature Biotechnology 24(12):1591-1597, Nature America Publishing, United States (2006).

Dechant, M. and Valerius, T., "IgA Antibodies for Cancer Therapy," Critical Reviews in Oncology/Hematology 39(1-2):69-77, Elsevier Science Ireland, Ireland (2001).

Dechant, M., et al., "Chimeric IgA Antibodies Against HLA Class II Effectively Trigger Lymphoma Cell Killing," Blood 100(13):4574-4580, American Society of Hematology, United States (2002).

Dechant, M., et al.. "Effector Mechanisms of Recombinant IgA Antibodies Against Epidermal Growth Factor Receptor," Journal of Immunology 179(5):2936-2943, American Association of Immunologists, United States (2007).

Durocher, Y., et al., "High-level and High-throughput Recombinant Protein Production by Transient Transfection of Suspension-growing Human 293-EBNA 1 Cells," Nucleic Acids Research 30(2):E9, Oxford University Press, England (2002).

Favre, L.I., et al., "Simplified Procedure to Recover Recombinant Antigenized Secretory IgA to be Used as a Vaccine Vector," Journal of Chromatography. B 786(1-2):143-151, Elsevier, Netherlands (2003).

Fernandes, D., "Demonstrating Comparability of Antibody Glycosylation During Biomanufacturing," European Pharmaceutical Review 106-110, Samedan Ltd., Germany (2005).

Garber, K., "Anti-IL-17 mAbs Herald New Options in Psoriasis," Nature Biotechnology 30(6):475-477, Nature America Publishing, United States (2012).

Gasdaska, J.R., et al., "Advantages of Therapeutic Protein Production in the Aquatic Plant Lemna," Bioprocessing Journal 2(2):49-56, Williamsburg Bioprocessing Foundation, United States (2003).

GenBank, "Rice alpha-amylase mRNA, complete cds, clone pOS103" Accession No. M24286.1, accessed at http://www.ncbi.nlm.nih.gov/nuccore/M24286, accessed on Dec. 12, 2015, 2 pages.

GenBank, "Lemna minor alpha-1,3-fucosyltransferase (FuctI) mRNA, complete cds" Accession No. DQ789145.1, accessed at http://www.ncbi.nlm.nih.gov/nuccore/DQ789145, accessed on Dec. 12, 2015, 2 pages.

GenBank, "Lemma minor beta-1,2-xylosyltransferase isoform 1 (Xylt1) mRNA, partial cds" Accession No. DQ789146.1, accessed at http://www.ncbi.nlm.nih.gov/nuccore/DQ789146, accessed on Dec. 12, 2015, 2 pages.

Graf, H., et al., "Ion Exchange Resins for the Purification of Monoclonal Antibodies from Animal Cell Culture," Bioseparation 4(1):7-20, Kluwer Academic Publishers, Netherlands (1994).

Hepburn, A.G., et al., "The Use of pNJ5000 as an Intermediate Vector for the Genetic Manipulation of Agrobacterium Ti-plasmids," Journal of General Microbiology 131(11):2961-2969, Society for General Microbiology, England (1985).

Huls, G., et al., "Antitumor Immune Effector Mechanisms Recruited by Phage Display-derived Fully Human IgG1 and IgA1 Monoclonal Antibodies," Cancer Research 59(22):5778-5784, American Association for Cancer Research, United States (1999).

Iansante, V., et al., "Biotechnological Approaches for the Treatment of Inflammatory Disease " Anti-Inflammatory and Anti-Allergy Agents in Medicinal Chemistry 8(1):51-71 (2009).

International Search Report and Written Opinion for International Application No. PCT/EP2012/075670, European Patent Office, Netherlands, mailed on Apr. 12, 2013, 14 pages.

International Search Report and Written Opinion for International Application No. PCT/EP2012/075671, European Patent Office, Netherlands, mailed on May 7, 2013, 14 pages.

International Search Report and Written Opinion for International Application No. PCT/EP2012/075672, European Patent Office, Netherlands, mailed on Mar. 21, 2013, 14 pages.

International Search Report and Written Opinion for International Application No. PCT/EP2012/075673, European Patent Office, Netherlands, mailed on Apr. 5, 2013, 13 pages.

Jefferis, R., "Glycosylation as a Strategy to Improve Antibody-based Therapeutics," Nature Reviews. Drug Discovery 8(3):226-234, Macmillan Publishers Ltd., England (2009).

(56) References Cited

OTHER PUBLICATIONS

Kalliolias, G.D. and Ivashkiv, L.B., "Targeting Cytokines in Inflammatory Diseases: Focus on Interleukin-1-mediated Autoinflammation," F1000 Biology Reports 1:70, Faculty of 1000, England (2009).

Karnoup, A.S., et al., "O-linked Glycosylation in Maize-expressed Human IgA1," Glycobiology 15(10):965-981, Oxford University Press, England (2005).

Knight, D.M., et al., "Construction and Initial Characterization of a Mouse-human Chimeric Anti-TNF Antibody," Molecular Immunology 30(16):1443-1453, Pergamon Press, England (1993).

Lash, A., "Making the Case for Antibody-Drug Conjugates," In Vivo: The Business and Medicine Report 28(11):32-38, Informa Business Information, Inc,, England (2010).

Lohse, S., et al., "Recombinant Dimeric IgA Antibodies Against the Epidermal Growth Factor Receptor Mediate Effective Tumor Cell Killing," Journal of Immunology 186(6):3770-3778, American Association of Immunologists, United States (2011).

Ma, J.K-C., et al., "Characterization of a Recombinant Plant Monoclonal Secretory Antibody and Preventive Immunotherapy in Humans," Nature Medicine 4(5):601-606, Nature Publishing Company, United States (1998).

Ma, J.K-C., et al., "Generation and Assembly of Secretory Antibodies in Plants," Science 268(5211):716-719, American Association for the Advancement of Science, United States (1995).

Ma, J.K-C., et al., "The Production of Recombinant Pharmaceutical Proteins in Plants," Nature Reviews Genetics 4(10):794-805, Nature Publishing Group, England (2003).

Maddox, D.E., et al., "Elevated Serum Levels in Human Pregnancy of a Molecule Immunochemically Similar to Eosinophil Granule Major Basic Protein," Journal of Experimental Medicine 158(4):1211-1226, Rockefeller University Press, United States (1983).

Morelle, W. and Michalski, J.C., "The Mass Spectrometric Analysis of Glycoproteins and their Glycan Structures," Current Analytical Chemistry 1(1):29-57, Bentham Science Publishers, United Arab Emirates (2005).

Morlot, C., et al., "Cloning, Expression, Crystallization and Preliminary X-ray Analysis of the First Two Ig Domains from Human Roundabout 1 (Robot)," Acta Crystallographica. Section F 63:689-691, Wiley-Blackwell, England (2007).

Negrouk, V., et al., "Highly Efficient Transient Expression of Functional Recombinant Antibodies in Lettuce," Plant Science 169(2):433-438, Elsevier Ireland Ltd., Ireland (2005).

Nguyen, L.V., et al., "Genetic Engineering of a Lemna Isoleucine Auxotroph," Transgenic Research 21(5):1071-1083, Springer Science and Business Media B.V., Netherlands (2012).

Ni, M., et al., "Strength and Tissue Specificity of Chimeric Promoters Derived from the Octopine and Mannopine Synthase Genes," The Plant Journal 7(4):661-676, John Wiley and Sons, United States (1995).

Pabst, O., "New Concepts in the Generation and Functions of IgA," Nature Reviews. Immunology 12(12):821-832, Macmillan Publishers Limited, England (2012).

Pleass, R.J, et al., "Novel Antimalarial Antibodies Highlight the Importance of the Antibody Fc Region in Mediating Protection," Blood 102(13):4424-4430, American Society of Hematology, United States (2003).

Preston, M.J., et al., "Production and Characterization of a Set of Mouse-human Chimeric Immunoglobulin G (IgG) Subclass and IgA Monoclonal Antibodies with Identical Variable Regions Specific for Pseudomonas Aeruginosa Serogroup O6 Lipopolysaccharide," Infection and Immunity 66(9):4137-4142, American Society for Microbiology, United States (1998).

Reichert, J.M., "Antibody-based Therapeutics to Watch in 2011," mAbs 3(1):76-99, Landes Bioscience, United States (2011).

Reichert, J.M., "Which are the Antibodies to Watch in 2012?," mAbs 4(1):1-3 Landes Biosciences, United States (2012).

Reimund, J.M., et al., "Anti-Tumor Necrosis Factor-alpha (TNF-α) Treatment Strategies in Crohn's Disease," Recent Patents on Inflammation and Allergy Drug Discovery 1(1):21-34, Bentham Science Publishers, United Arab Emirates (2007).

Schenk, R.U. and Hildebrandt, A.C., "Medium and Techniques for Induction and Growth of Monocotyledonous and Dicotyledonous Plant Cell Cultures," Canadian Journal of Botany 50(1):199-204, Canadian Science Publishers, Canada (1972).

Senior, B.W. and Woof, J.M., "The Influences of Hinge Length and Composition on the Susceptibility of Human IgA to Cleavage by Diverse Bacterial IgA1 Proteases," Journal of Immunology 174(12):7792-7799, American Association of Immunologists, United States (2005).

Snoeck, V., et al., "The IgA System: A Comparison of Structure and Function in Different Species," Veterinary Research 37(3):455-467, IRA/EDP Sciences, France (2006).

Stubbe, H., et al, "Polymeric IgA is Superior to Monomeric IgA and IgG Carrying the Same Variable Domain in Preventing Clostridium Difficile Toxin A Damaging of T84 Monolayers," Journal of Immunology 164(4):1952-1960, American Association of Immunologists, United States (2000).

Sun, L.K., et al., "Human IgA Monoclonal Antibodies Specific for a Major Ragweed Pollen Antigen," Biotechnology 13(8):779-786, Nature Publishing Company, United States (1995).

Synthon: LEX System Overview, Sep. 2012, Retrieved from the Internet: URL:http://www.molecularfarming.org/FA0804_Dickey_Warsaw_2012.pdf, retrieved on Feb. 26, 2013, 34 pages.

Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).

Van Der Vossen, E.A., et al., "Role of the 5' Leader Sequence of Alfalfa Mosaic Virus RNA 3 in Replication and Translation of the Viral RNA," Nucleic Acids Research 21(6):1361-1367, Oxford University Press, England (1993).

Van Engelen, F.A., et al., "Coordinate Expression of Antibody Subunit Genes Yields High Levels of Functional Antibodies in Roots of Transgenic Tobacco," Plant Molecular Biology 26(6):1701-1710, Kluwer Academic, Netherlands (1994).

Van Engelen, F.A., et al., "pBINPLUS: An Improved Plant Transformation Vector Based on pBIN19," Transgenic Research 4(4):288-290, Chapman & Hall, England (1995).

Vidarsson, G., et al., "Activity of Human IgG and IgA Subclasses in Immune Defense Against Neisseria Meningitidis Serogroup B," Journal of Immunology 166(10):6250-6256, American Association of Immunologists, United States (2001).

Wang, L. and Roossinck, M.J., "Comparative Analysis of Expressed Sequences Reveals a Conserved Pattern of Optimal Codon Usage in Plants," Plant Molecular Biology 61(4-5):699-710, Springer Science and Business Media B.V., Netherlands (2006).

Worledge, K.L., et al., "Oral Administration of Avian Tumor Necrosis Factor Antibodies Effectively Treats Experimental Colitis in Rats," Digestive Diseases and Sciences 45(12):2298-2305, Plenam Publishing Corporation, United States (2000).

Wycoff, K.L., "Secretory IgA Antibodies from Plants," Current Pharmaceutical Design 11(19):2429-2437, Bentham Science Publishers, United Arab Emirates (2005).

Yamashita, M., et al., "Recent Advances in the Generation of Human Monoclonal Antibody," Cytotechnology 55(2-3):55-60, Springer Science and Business Media B.V., Netherlands (2007).

Ye, D., et al., "Molecular Mechanism of Tumor Necrosis Factor-alpha Modulation of Intestinal Epithelial Tight Junction Barrier," American Journal of Physiology. Gastrointestinal and Liver Physiology 290(3):G496-G504, American Physiological Society, United States (2006).

Non-final Office Action in U.S. Appl. No. 14/365,867, mailed Nov. 6, 2015, Gerardus et al., filed Jun. 16, 2014.

Non-final Office Action in U.S. Appl. No. 14/365,940, mailed Jan. 5, 2016, Gerardus et al., filed Jun. 16, 2014.

* cited by examiner

FIGURE 1

```
             |                        Cα1
α1      ASPTSPKVFPLSLCSTQPDGNVVIACLVQGFFPQEPLSVTWSESGQGVTARNFPPSQDAS
α2m(1)  ASPTSPKVFPLSLDSTPQDGNVVVACLVQGFFPQEPLSVTWSESGQNVTARNFPPSQDAS
α2m(2)  ASPTSPKVFPLSLDSTPQDGNVVVACLVQGFFPQEPLSVTWSESGQNVTARNFPPSQDAS
α2(n)   ASPTSPKVFPLSLDSTPQDGNVVVACLVQGFFPQEPLSVTWSESGQNVTARNFPPSQDAS
        ..........|...^...^^.|....^.....|..........|......^..|.........|
        1         10        20        30        40        50        60
                                                        || Hinge
α1      GDLYTTSSQLTLPATQCLAGKSVTCHVKHYTNPSQDVTVPCPVPSTPPTPSPSTPPTPSP
α2m(1)  GDLYTTSSQLTLPATQCPDGKSVTCHVKHYTNPSQDVTVPCPVP              PPP
α2m(2)  GDLYTTSSQLTLPATQCPDGKSVTCHVKHYTNSSQDVTVPCRVP              PPP
α2(n)   GDLYTTSSQLTLPATQCPDGKSVTCHVKHYTNSSQDVTVPCRVP              PPP
        ..........|.......^^.|..........|.....^....|..^......|.........|
                  70        80        90        100       110       120
        /|                       Cα2
α1      SCCHPRLSLHRPALEDLLLGSEANLTCTLTGLRDASGVTFTWTPSSGKSAVQGPPERDLC
α2m(1)  PCCHPRLSLHRPALEDLLLGSEANLTCTLTGLRDASGATFTWTPSSGKSAVQGPPERDLC
α2m(2)  PCCHPRLSLHRPALEDLLLGSEANLTCTLTGLRDASGATFTWTPSSGKSAVQGPPERDLC
α2(n)   PCCHPRLSLHRPALEDLLLGSEANLTCTLTGLRDASGATFTWTPSSGKSAVQGPPERDLC
        ..........|..........|..........|........^.|..........|.........|
                  130       140       150       160       170       180
                                                ||
α1      GCYSVSSVLPGCAEPWNHGKTFTCTAAYPESKTPLTATLSKSGNTFRPEVHLLPPPSEEL
α2m(1)  GCYSVSSVLPGCAQPWNHGETFTCTAAHPELKTPLTANITKSGNTFRPEVHLLPPPSEEL
α2m(2)  GCYSVSSVLPGCAQPWNHGETFTCTAAHPELKTPLTANITKSGNTFRPEVHLLPPPSEEL
α2(n)   GCYSVSSVLPGCAQPWNHGETFTCTAAHPELKTPLTANITKSGNTFRPEVHLLPPPSEEL
        ..........|...^.....^.......^.|^....^^^.....|..........|.........|
                  190       200       210       220       230       240
                                 Cα3
α1      ALNELVTLTCLARGFSPKDVLVRWLQGSQELPREKYLTWASRQEPSQGTTTFAVTSILRV
α2m(1)  ALNELVTLTCLARGFSPKDVLVRWLQGSQELPREKYLTWASRQEPSQGTTTFAVTSILRV
α2m(2)  ALNELVTLTCLARGFSPKDVLVRWLQGSQELPREKYLTWASRQEPSQGTTTYAVTSILRV
α2(n)   ALNELVTLTCLARGFSPKDVLVRWLQGSQELPREKYLTWASRQEPSQGTTTFAVTSILRV
        ..........|..........|..........|..........|..........|.^.......|
                  250       260       270       280       290       300
                                                        || Tailpiece
α1      AAEDWKKGDTFSCMVGHEALPLAFTQKTIDRLAGKPTHVNVSVVMAEVDGTCY
α2m(1)  AAEDWKKGDTFSCMVGHEALPLAFTQKTIDRLAGKPTHVNVSVVMAEVDGTCY
α2m(2)  AAEDWKKGETFSCMVGHEALPLAFTQKTIDRLAGKPTHINVSVVMAEADGTCY
α2(n)   AAEDWKKGDTFSCMVGHEALPLAFTQKTIDRLAGKPTHVNVSVVMAEVDGTCY
        ........^.|..........|..........|.....^...|......^.|....
                  310       320       330       340       350 353
```

FIGURE 2A
```
LPAQVAFTPYAPEPGSTCRLREYYDQTAQMCCSKCSPGQHAKVFCTKTSDTVCDSCEDST
.........|.........|.........|.........|.........|.........|
         10        20        30        40        50        60

YTQLWNWVPECLSCGSRCSSDQVETQACTREQNRICTCRPGWYCALSKQEGCRLCAPLRK
.........|.........|.........|.........|.........|.........|
         70        80        90       100       110       120

CRPGFGVARPGTETSDVVCKPCAPGTFSNTTSSTDICRPHQICNVVAIPGNASMDAVCTS
.........|.........|.........|.........|.........|.........|
        130       140       150       160       170       180

TSPTRSMAPGAVHLPQPVSTRSQHTQPTPEPSTAPSTSFLLPMGPSPPAEGSTGD
.........|.........|.........|.........|.........|......
        190       200       210       220       230
```

FIGURE 2B
```
        FR1                |--CDR1--|    FR2         |----CDR2--
EVKLEESGGGLVQPGGSMKLSCVASGFIFSNHWMNWVRQSPEKGLEWVAEIRSKSINSAT
.........|.........|.........|.........|.........|.........|
1        10        20        30        40        50        60

-------|           FR3                  |-CDR3--|      FR4
HYAESVKGRFTISRDDSKSAVYLQMTDLRTEDTGVYYCSRNYYGSTYDYWGQGTTLTVSS
.........|.........|.........|.........|.........|.........|
         70        80        90       100       110       120
```

FIGURE 2C
```
        FR1                 |--CDR1---|    FR2          |-CDR2|
DILLTQSPAILSVSPGERVSFSCRASQFVGSSIHWYQQRTNGSPRLLIKYASESMSGIPS
.........|.........|.........|.........|.........|.........|
1        10        20        30        40        50        60

FR3               |--CDR3-|    FR4
RFSGSGSGTDFTLSINTVESEDIADYYCQQSHSWPFTFGSGTNLEVK
.........|.........|.........|.........|........
         70        80        90       100      107
```

FIGURE 2D
```
        FR1                |--CDR1--|    FR2         |----CDR2--
EVQLVESGGGLVQPGRSLRLSCAASGFTFDDYAMHWVRQAPGKGLEWVSAITWNSGHIDY
.........|.........|.........|.........|.........|.........|
1        10        20        30        40        50        60

-----|            FR3                   |-CDR3--|      FR4
ADSVEGRFTISRDNAKNSLYLQMNSLRAEDTAVYYCAKVSYLSTASSLDYWGQGTLVTVSS
.........|.........|.........|.........|.........|.........|.
         70        80        90       100       110       121
```

FIGURE 2E
```
        FR1                 |--CDR1---|    FR2          |-CDR2|
DIQMTQSPSSLSASVGDRVTITCRASQGIRNYLAWYQQKPGKAPKLLIYAASTLQSGVPS
.........|.........|.........|.........|.........|.........|
1        10        20        30        40        50        60

FR3               |--CDR3-|    FR4
RFSGSGSGTDFTLTISSLQPEDVATYYCQRYNRAPYTFGQGTKVEIK
.........|.........|.........|.........|........
         70        80        90       100      107
```

FIGURE 2F
```
        FR1                |--CDR1--|    FR2         |----CDR2--
QVQLVESGGGVVQPGRSLRLSCAASGFIFSSYAMHWVRQAPGNGLEWVAFMSYDGSNKKY
```

```
         ........|.........|.........|.........|.........|.........|
         1       10        20        30        40        50        60

-----|           FR3                 |------CDR3-----|    FR4
         ADSVKGRFTISRDNSKNTLYLQMNSLRAEDTAVYYCARDRGIAAGGNYYYYGMDVWGQGTTVTVSS
         ........|.........|.........|.........|.........|.........|......
                 70        80        90        100       110       120  126
```

FIGURE 2G

```
                FR1             |--CDR1---|      FR2          |-CDR2|
         EIVLTQSPATLSLSPGERATLSCRASQSVYSYLAWYQQKPGQAPRLLIYDASNRATGIPA
         ........|.........|.........|.........|.........|.........|
         1       10        20        30        40        50        60
                   FR3              |--CDR3--|   FR4
         RFSGSGSGTDFTLTISSLEPEDFAVYYCQQRSNWPPFTFGPGTKVDIK
         ........|.........|.........|.........|........
                 70        80        90        100     108
```

FIGURE 2H

```
                FR1                |--CDR1--|      FR2           |----CDR2--
         EVQLVESGGGLVQPGGSLRLSCAASGYVFTDYGMNWVRQAPGKGLEWMGWINTYIGEPIY
         ........|.........|.........|.........|.........|.........|
         1       10        20        30        40        50        60

-----|           FR3                    |--CDR3-|    FR4
         ADSVKGRFTFSLDTSKSTAYLQMNSLRAEDTAVYYCARGYRSYAMDYWGQGTLVTVSS
         ........|.........|.........|.........|.........|........
                 70        80        90        100       110     118
```

FIGURE 2I

```
                FR1             |--CDR1---|      FR2          |-CDR2|
         DIQMTQSPSSLSASVGDRVTITCKASQNVGTNVAWYQQKPGKAPKALIYSASFLYSGVPY
         ........|.........|.........|.........|.........|.........|
         1       10        20        30        40        50        60
                   FR3              |--CDR3-|   FR4
         RFSGSGSGTDFTLTISSLQPEDFATYYCQQYNIYPLTFGQGTKVEIK
         ........|.........|.........|.........|.......
                 70        80        90        100   107
```

FIGURE 3A

```
            |                                      CL
κ    RTVAAPSVFIFPPSDEQLKSGTASVVCLLNNFYPREAKVQWKVDNALQSGNSQESVTEQD
     .........|.........|.........|.........|.........|.........|
     1        10        20        30        40        50        60

|
     SKDSTYSLSSTLTLSKADYEKHKVYACEVTHQGLSSPVTKSFNRGEC
     .........|.........|.........|.........|.......
              70        80        90        100  107
```

FIGURE 3B

```
            |                                      CL
λ1   GQPKANPTVTLFPPSSEELQANKATLVCLISDFYPGAVTVAWKADGSPVKAGVETTKPSK
λ2   GQPKAAPSVTLFPPSSEELQANKATLVCLISDFYPGAVTVAWKADSSPVKAGVETTTPSK
λ3   GQPKAAPSVTLFPPSSEELQANKATLVCLISDFYPGAVTVAWKADSSPVKAGVETTTPSK
λ6   GQPKAAPSVTLFPPSSEELQANKATLVCLISDFYPGAVKVAWKADGSPVNTGVETTTPSK
λ7   GQPKAAPSVTLFPPSSEELQANKATLVCLVSDFYPGAVTVAWKADGSPVKVGVETTKPSK
     .........|.........|.........|.........|.........|.........|
     1        10        20        30        40        50        60

|
     QSNNKYAASSYLSLTPEQWKSHRSYSCQVTHEGSTVEKTVAPTECS
     QSNNKYAASSYLSLTPEQWKSHRSYSCQVTHEGSTVEKTVAPTECS
     QSNNKYAASSYLSLTPEQWKSHKSYSCQVTHEGSTVEKTVAPTECS
     QSNNKYAASSYLSLTPEQWKSHRSYSCQVTHEGSTVEKTVAPAECS
     QSNNKYAASSYLSLTPEQWKSHRSYSCRVTHEGSTVEKTVAPAECS
     .........|.........|.........|.........|......
              70        80        90        100  106
```

FIGURE 4

```
QEDERIVLVDNKCKCARITSRIIRSSEDPNEDIVERNIRIIVPLNNRENISDPTSPLRTR
.........|.........|.........|.........|.........|.........|
1        10        20        30        40        50        60

FVYHLSDLCKKCDPTEVELDNQIVTATQSNICDEDSATETCYTDRNKCYTAVVPLVYGG
.........|.........|.........|.........|.........|.........|
         70        80        90        100       110       120

ETKMVETALTPDACYPD
.........|.......
         130   137
```

FIGURE 5

```
KSPIFGPEEVNSVEGNSVSITCYYPPTSVNRHTRKYWCRQGARGGCITLISSEGYVSSKY
.........|.........|.........|.........|.........|.........|
1         10        20        30        40        50        60

AGRANLTNFPENGTFVVNIAQLSQDDSGRYKCGLGINSRGLSFDVSLEVSQGPGLLNDTK
.........|.........|.........|.........|.........|.........|
          70        80        90       100       110       120

VYTVDLGRTVTINCPFKTENAQKRKSLYKQIGLYPVLVIDSSGYVNPNYTGRIRLDIQGT
.........|.........|.........|.........|.........|.........|
         130       140       150       160       170       180

GQLLFSVVINQLRLSDAGQYLCQAGDDSNSNKKNADLQVLKPEPELVYEDLRGSVTFHCA
.........|.........|.........|.........|.........|.........|
         190       200       210       220       230       240

LGPEVANVAKFLCRQSSGENCDVVVNTLGKRAPAFEGRILLNPQDKDGSFSVVITGLRKE
.........|.........|.........|.........|.........|.........|
         250       260       270       280       290       300

DAGRYLCGAHSDGQLQEGSPIQAWQLFVNEESTIPRSPTVVKGVAGSSVAVLCPYNRKES
.........|.........|.........|.........|.........|.........|
         310       320       330       340       350       360

KSIKYWCLWEGAQNGRCPLLVDSEGWVKAQYEGRLSLLEEPGNGTFTVILNQLTSRDAGF
.........|.........|.........|.........|.........|.........|
         370       380       390       400       410       420

YWCLTNGDTLWRTTVEIKIIEGEPNLKVPGNVTAVLGETLKVPCHFPCKFSSYEKYWCKW
.........|.........|.........|.........|.........|.........|
         430       440       450       460       470       480

NNTGCQALPSQDEGPSKAFVNCDENSRLVSLTLNLVTRADEGWYWCGVKQGHFYGETAAV
.........|.........|.........|.........|.........|.........|
         490       500       510       520       530       540

YVAVEERKAAGSRDVSLAKADAAPDEKVLDSGFREIENKAIQDPR
.........|.........|.........|.........|....
         550       560       570       580  585
```

FIGURE 14
| Treatment | PBS Oral | ADB-SA1g Oral | Adalimumab Subcutaneous |
|---|---|---|---|
| Mini-endoscopy Day t=15 | 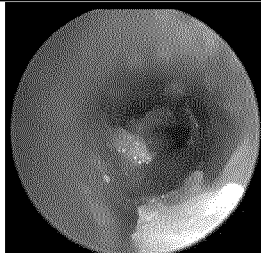 | 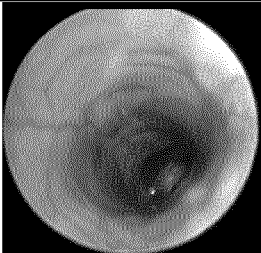 | 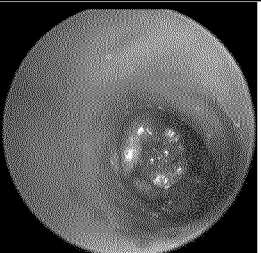 |

SEQUENCE LISTING

```
<160> NUMBER OF SEQ ID NOS: 36

<210> SEQ ID NO 1
<211> LENGTH: 235
<212> TYPE: PRT
<213> ORGANISM: Artificial Sequence
<220> FEATURE:
<223> OTHER INFORMATION: Amino acid sequence of the soluble TNFalpha
      receptor of etanercept (extracellular part of TNF receptor 2:
      amino acids 23-257 of UniProtKB/Swiss-Prot database entry P20333
      TNR1B_HUMAN).

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125
```

-continued

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

<210> SEQ ID NO 2
<211> LENGTH: 120
<212> TYPE: PRT
<213> ORGANISM: Artificial Sequence
<220> FEATURE:
<223> OTHER INFORMATION: Amino acid sequence of the heavy chain variable
      region of infliximab (cA2).

<400> SEQUENCE: 2

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120

<210> SEQ ID NO 3
<211> LENGTH: 107
<212> TYPE: PRT
<213> ORGANISM: Artificial Sequence
<220> FEATURE:
<223> OTHER INFORMATION: Amino acid sequence of the light chain variable
      region of infliximab (cA2).

<400> SEQUENCE: 3

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105

<210> SEQ ID NO 4
<211> LENGTH: 121
<212> TYPE: PRT
<213> ORGANISM: Artificial Sequence
<220> FEATURE:
<223> OTHER INFORMATION: Amino acid sequence of the heavy chain variable
      region of adalimumab (D2E7).

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Amino acid sequence of the light chain variable
      region of adalimumab (D2E7).

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 6

```
<211> LENGTH: 126
<212> TYPE: PRT
<213> ORGANISM: Artificial Sequence
<220> FEATURE:
<223> OTHER INFORMATION: Amino acid sequence of the heavy chain variable
      region of golimumab.

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 7
<211> LENGTH: 108
<212> TYPE: PRT
<213> ORGANISM: Artificial Sequence
<220> FEATURE:
<223> OTHER INFORMATION: Amino acid sequence of the light chain variable
      region of golimumab.

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 8
<211> LENGTH: 118
<212> TYPE: PRT
<213> ORGANISM: Artificial Sequence
<220> FEATURE:
<223> OTHER INFORMATION: Amino acid sequence of the heavy chain variable
      region of certolizumab pegol.

<400> SEQUENCE: 8

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
            115

<210> SEQ ID NO 9
<211> LENGTH: 107
<212> TYPE: PRT
<213> ORGANISM: Artificial Sequence
<220> FEATURE:
<223> OTHER INFORMATION: Amino acid sequence of the light chain variable
      region of certolizumab pegol.

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 10
<211> LENGTH: 353
<212> TYPE: PRT
<213> ORGANISM: Homo sapiens

<400> SEQUENCE: 10

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95
```

-continued

Val Thr Val Pro Cys Pro Val Pro Ser Thr Pro Thr Pro Ser Pro
            100                 105                 110

Ser Thr Pro Pro Thr Pro Ser Pro Ser Cys Cys His Pro Arg Leu Ser
    115                 120                 125

Leu His Arg Pro Ala Leu Glu Asp Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
    195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
    260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 11
<211> LENGTH: 340
<212> TYPE: PRT
<213> ORGANISM: Homo sapiens

<400> SEQUENCE: 11

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

```
Arg Leu Ser Leu His Arg Pro Ala Leu Glu Asp Leu Leu Gly Ser
        115                 120                 125
Glu Ala Asn Leu Thr Cys Thr Leu Thr Gly Leu Arg Asp Ala Ser Gly
130                 135                 140
Ala Thr Phe Thr Trp Thr Pro Ser Ser Gly Lys Ser Ala Val Gln Gly
145                 150                 155                 160
Pro Pro Glu Arg Asp Leu Cys Gly Cys Tyr Ser Val Ser Ser Val Leu
                165                 170                 175
Pro Gly Cys Ala Gln Pro Trp Asn His Gly Glu Thr Phe Thr Cys Thr
            180                 185                 190
Ala Ala His Pro Glu Leu Lys Thr Pro Leu Thr Ala Asn Ile Thr Lys
        195                 200                 205
Ser Gly Asn Thr Phe Arg Pro Glu Val His Leu Leu Pro Pro Pro Ser
210                 215                 220
Glu Glu Leu Ala Leu Asn Glu Leu Val Thr Leu Thr Cys Leu Ala Arg
225                 230                 235                 240
Gly Phe Ser Pro Lys Asp Val Leu Val Arg Trp Leu Gln Gly Ser Gln
                245                 250                 255
Glu Leu Pro Arg Glu Lys Tyr Leu Thr Trp Ala Ser Arg Gln Glu Pro
            260                 265                 270
Ser Gln Gly Thr Thr Thr Phe Ala Val Thr Ser Ile Leu Arg Val Ala
        275                 280                 285
Ala Glu Asp Trp Lys Lys Gly Asp Thr Phe Ser Cys Met Val Gly His
290                 295                 300
Glu Ala Leu Pro Leu Ala Phe Thr Gln Lys Thr Ile Asp Arg Leu Ala
305                 310                 315                 320
Gly Lys Pro Thr His Val Asn Val Ser Val Val Met Ala Glu Val Asp
                325                 330                 335
Gly Thr Cys Tyr
            340

<210> SEQ ID NO 12
<211> LENGTH: 340
<212> TYPE: PRT
<213> ORGANISM: Homo sapiens

<400> SEQUENCE: 12

Ala Ser Pro Thr Ser Pro Lys Val Phe Pro Leu Ser Leu Asp Ser Thr
1               5                   10                  15
Pro Gln Asp Gly Asn Val Val Val Ala Cys Leu Val Gln Gly Phe Phe
                20                  25                  30
Pro Gln Glu Pro Leu Ser Val Thr Trp Ser Glu Ser Gly Gln Asn Val
            35                  40                  45
Thr Ala Arg Asn Phe Pro Pro Ser Gln Asp Ala Ser Gly Asp Leu Tyr
        50                  55                  60
Thr Thr Ser Ser Gln Leu Thr Leu Pro Ala Thr Gln Cys Pro Asp Gly
65                  70                  75                  80
Lys Ser Val Thr Cys His Val Lys His Tyr Thr Asn Ser Ser Gln Asp
                85                  90                  95
Val Thr Val Pro Cys Arg Val Pro Pro Pro Cys Cys His Pro
            100                 105                 110
Arg Leu Ser Leu His Arg Pro Ala Leu Glu Asp Leu Leu Gly Ser
        115                 120                 125
Glu Ala Asn Leu Thr Cys Thr Leu Thr Gly Leu Arg Asp Ala Ser Gly
130                 135                 140
```

```
Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
        180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
        275                 280                 285

Ala Glu Asp Trp Lys Lys Gly Glu Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
                325                 330                 335

Gly Thr Cys Tyr
            340

<210> SEQ ID NO 13
<211> LENGTH: 340
<212> TYPE: PRT
<213> ORGANISM: Homo sapiens

<400> SEQUENCE: 13

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro Arg
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
```

```
                        165                 170                 175
Pro Gly Cys Ala Gln Pro Trp Asn His Gly Glu Thr Phe Thr Cys Thr
                180                 185                 190
Ala Ala His Pro Glu Leu Lys Thr Pro Leu Thr Ala Asn Ile Thr Lys
            195                 200                 205
Ser Gly Asn Thr Phe Arg Pro Glu Val His Leu Leu Pro Pro Pro Ser
        210                 215                 220
Glu Glu Leu Ala Leu Asn Glu Leu Val Thr Leu Thr Cys Leu Ala Arg
225                 230                 235                 240
Gly Phe Ser Pro Lys Asp Val Leu Val Arg Trp Leu Gln Gly Ser Gln
                245                 250                 255
Glu Leu Pro Arg Glu Lys Tyr Leu Thr Trp Ala Ser Arg Gln Glu Pro
            260                 265                 270
Ser Gln Gly Thr Thr Phe Ala Val Thr Ser Ile Leu Arg Val Ala
        275                 280                 285
Ala Glu Asp Trp Lys Lys Gly Asp Thr Phe Ser Cys Met Val Gly His
    290                 295                 300
Glu Ala Leu Pro Leu Ala Phe Thr Gln Lys Thr Ile Asp Arg Leu Ala
305                 310                 315                 320
Gly Lys Pro Thr His Val Asn Val Ser Val Val Met Ala Glu Val Asp
                325                 330                 335
Gly Thr Cys Tyr
            340

<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 15
<211> LENGTH: 106
<212> TYPE: PRT
<213> ORGANISM: Homo sapiens

<400> SEQUENCE: 15

Gly Gln Pro Lys Ala Asn Pro Thr Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Gly Ser Pro
```

```
                35                  40                  45
Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 16
<211> LENGTH: 106
<212> TYPE: PRT
<213> ORGANISM: Homo sapiens

<400> SEQUENCE: 16

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 17
<211> LENGTH: 106
<212> TYPE: PRT
<213> ORGANISM: Homo sapiens

<400> SEQUENCE: 17

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Ala Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 18
<211> LENGTH: 106
<212> TYPE: PRT
<213> ORGANISM: Homo sapiens

<400> SEQUENCE: 18
```

-continued

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 19
<211> LENGTH: 106
<212> TYPE: PRT
<213> ORGANISM: Homo sapiens

<400> SEQUENCE: 19

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 20
<211> LENGTH: 137
<212> TYPE: PRT
<213> ORGANISM: Homo sapiens

<400> SEQUENCE: 20

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
            115                 120                 125

Leu Thr Pro Asp Ala Cys Tyr Pro Asp
    130                 135

<210> SEQ ID NO 21
<211> LENGTH: 585
<212> TYPE: PRT
<213> ORGANISM: Homo sapiens

<400> SEQUENCE: 21

Lys Ser Pro Ile Phe Gly Pro Glu Val Asn Ser Val Glu Gly Asn
1               5                   10                  15

Ser Val Ser Ile Thr Cys Tyr Tyr Pro Pro Thr Ser Val Asn Arg His
            20                  25                  30

Thr Arg Lys Tyr Trp Cys Arg Gln Gly Ala Arg Gly Gly Cys Ile Thr
        35                  40                  45

Leu Ile Ser Ser Glu Gly Tyr Val Ser Lys Tyr Ala Gly Arg Ala
    50                  55                  60

Asn Leu Thr Asn Phe Pro Glu Asn Gly Thr Phe Val Val Asn Ile Ala
65                  70                  75                  80

Gln Leu Ser Gln Asp Asp Ser Gly Arg Tyr Lys Cys Gly Leu Gly Ile
                85                  90                  95

Asn Ser Arg Gly Leu Ser Phe Asp Val Ser Leu Glu Val Ser Gln Gly
            100                 105                 110

Pro Gly Leu Leu Asn Asp Thr Lys Val Tyr Thr Val Asp Leu Gly Arg
        115                 120                 125

Thr Val Thr Ile Asn Cys Pro Phe Lys Thr Glu Asn Ala Gln Lys Arg
    130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
                165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro
    210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
    290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
                325                 330                 335

Ser Pro Thr Val Val Lys Gly Val Ala Gly Gly Ser Val Ala Val Leu

-continued

```
                340                 345                 350
Cys Pro Tyr Asn Arg Lys Glu Ser Lys Ser Ile Lys Tyr Trp Cys Leu
        355                 360                 365
Trp Glu Gly Ala Gln Asn Gly Arg Cys Pro Leu Leu Val Asp Ser Glu
    370                 375                 380
Gly Trp Val Lys Ala Gln Tyr Glu Gly Arg Leu Ser Leu Leu Glu Glu
385                 390                 395                 400
Pro Gly Asn Gly Thr Phe Thr Val Ile Leu Asn Gln Leu Thr Ser Arg
                405                 410                 415
Asp Ala Gly Phe Tyr Trp Cys Leu Thr Asn Gly Asp Thr Leu Trp Arg
            420                 425                 430
Thr Thr Val Glu Ile Lys Ile Ile Glu Gly Glu Pro Asn Leu Lys Val
        435                 440                 445
Pro Gly Asn Val Thr Ala Val Leu Gly Glu Thr Leu Lys Val Pro Cys
    450                 455                 460
His Phe Pro Cys Lys Phe Ser Ser Tyr Glu Lys Tyr Trp Cys Lys Trp
465                 470                 475                 480
Asn Asn Thr Gly Cys Gln Ala Leu Pro Ser Gln Asp Glu Gly Pro Ser
                485                 490                 495
Lys Ala Phe Val Asn Cys Asp Glu Asn Ser Arg Leu Val Ser Leu Thr
            500                 505                 510
Leu Asn Leu Val Thr Arg Ala Asp Glu Gly Trp Tyr Trp Cys Gly Val
        515                 520                 525
Lys Gln Gly His Phe Tyr Gly Glu Thr Ala Ala Val Tyr Val Ala Val
    530                 535                 540
Glu Glu Arg Lys Ala Ala Gly Ser Arg Asp Val Ser Leu Ala Lys Ala
545                 550                 555                 560
Asp Ala Ala Pro Asp Glu Lys Val Leu Asp Ser Gly Phe Arg Glu Ile
                565                 570                 575
Glu Asn Lys Ala Ile Gln Asp Pro Arg
            580                 585
```

<210> SEQ ID NO 22
<211> LENGTH: 22
<212> TYPE: PRT
<213> ORGANISM: Homo sapiens

<400> SEQUENCE: 22

```
Met Lys Asn His Leu Leu Phe Trp Gly Val Leu Ala Val Phe Ile Lys
1               5                   10                  15
Ala Val His Val Lys Ala
            20
```

<210> SEQ ID NO 23
<211> LENGTH: 19
<212> TYPE: PRT
<213> ORGANISM: Artificial Sequence
<220> FEATURE:
<223> OTHER INFORMATION: Amino acid sequence for a signal peptide (heavy chain secretion signal).

<400> SEQUENCE: 23

```
Met Glu Leu Gly Leu Cys Trp Val Phe Leu Val Ala Ile Leu Glu Gly
1               5                   10                  15
Val Gln Cys
```

<210> SEQ ID NO 24

```
<211> LENGTH: 22
<212> TYPE: PRT
<213> ORGANISM: Artificial Sequence
<220> FEATURE:
<223> OTHER INFORMATION: Amino acid sequence for a signal peptide (light
      chain secretion signal).

<400> SEQUENCE: 24

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 25
<211> LENGTH: 20
<212> TYPE: PRT
<213> ORGANISM: Artificial Sequence
<220> FEATURE:
<223> OTHER INFORMATION: Amino acid sequence for a signal peptide (SC
      chain secretion signal).

<400> SEQUENCE: 25

Met Ala Met Leu Leu Phe Val Leu Thr Cys Leu Leu Ala Val Phe Pro
1               5                   10                  15

Ala Ile Ser Thr
            20

<210> SEQ ID NO 26
<211> LENGTH: 31
<212> TYPE: PRT
<213> ORGANISM: Artificial Sequence
<220> FEATURE:
<223> OTHER INFORMATION: Amino acid sequence for rice alpha-amylase
      signal peptide (secretion signal).

<400> SEQUENCE: 26

Met Gln Val Leu Asn Thr Met Val Asn Lys His Phe Leu Ser Leu Ser
1               5                   10                  15

Val Leu Ile Val Leu Leu Gly Leu Ser Ser Asn Leu Thr Ala Gly
            20                  25                  30

<210> SEQ ID NO 27
<211> LENGTH: 1440
<212> TYPE: DNA
<213> ORGANISM: Artificial Sequence
<220> FEATURE:
<223> OTHER INFORMATION: DNA sequence for infliximab heavy chain
      IgA2m(n) optimized for maize.

<400> SEQUENCE: 27
atggagctgg gcctgtgctg ggtgttcctg gtggccatcc tcgagggcgt ccagtgcgag      60
gtgaagctcg aggagtccgg cggcggcctg gtccagcctg gcggctccat gaagctgtcc     120
tgcgtggcct ccggcttcat cttctccaac cactggatga actgggtgcg ccagtccccc     180
gagaagggcc tcgagtgggt ggccgagatc cgctccaagt ccatcaactc cgccacccac     240
tacgccgagt ccgtcaaggg caggttcacc atctcccgcg acgactccaa gtccgccgtg     300
tacctccaga tgaccgacct cgcaccgag gacaccggcg tgtactactg ctcccgcaac     360
tactacggct ccacctacga ctactggggc cagggcacca ccctgaccgt gtcctccgct     420
agccccacct cccccaaggt gttcccctg tccctggact ccacccccca ggacggcaac     480
gtggtggtgg cctgcctggt ccagggcttc ttccccagg agccctgtc cgtcacctgg     540 agcgagtccg ccagaacgt gaccgcccgc aacttccccc cctcccagga cgcttccggc     600
```

```
gacctgtaca ccacctcctc ccagctgacc ctgcccgcta cccagtgccc cgacggcaag      660
tccgtgacct gccacgtgaa gcactacacc aactccagcc aggacgtgac cgtgccctgc      720
cgcgtgcctc ctccccctcc ctgctgccac ccaggctgt  cctgcacag  gcccgctctc      780 gaggacctgc tgctgggctc cgaggccaac ctgacctgca ccctgaccgg cctgagggac      840
gcctccggcg ctaccttcac ctggaccccc tcctccggca agtccgctgt ccaaggccca      900
cctgagcgtg atctctgcgg ctgctactcc gtgtccagcg tgctgcccgg ctgcgcccag      960
ccctggaacc acggcgagac cttcacctgc accgccgctc accccgagct taagacccccc     1020 ctgaccgcca acatcaccaa gtccggcaac accttccgcc cgaggtgca  cctgctgccc      1080 cctccctccg aggagctggc cctgaacgag ctggtgaccc tgacctgcct cgccagggc       1140 ttctccccga aggacgtgct tgtgcgctgg ctccagggct cccaggagct gccccgcgag      1200
aagtacctga cctgggcctc caggcaggag ccttcccagg gcaccaccac cttcgccgtg      1260
acctccatcc tgagggtggc cgccgaggac tggaagaagg cgacaccttt cagctgcatg     1320
gtgggtcacg aggctctgcc cctggccttc acccaaaaga ccatcgaccg cctggctggc      1380
aagcccaccc acgtgaacgt gtccgtggtg atggccgagg tggacggcac ctgctactga     1440

<210> SEQ ID NO 28
<211> LENGTH: 6910
<212> TYPE: DNA
<213> ORGANISM: Artificial Sequence
<220> FEATURE:
<223> OTHER INFORMATION: DNA sequence for infliximab heavy chain IgA1
      and light chain kappa optimized for HEK.

<400> SEQUENCE: 28
gcttcgcgat gtacgggcca gatatacgcg ttgacattga ttattgacta gttattaata       60
gtaatcaatt acggggtcat tagttcatag cccatatatg gagttccgcg ttacataact      120
tacggtaaat ggcccgcctg gctgaccgcc caacgacccc cgcccattga cgtcaataat      180
gacgtatgtt cccatagtaa cgccaatagg gactttccat tgacgtcaat gggtggagta      240
tttacggtaa actgcccact tggcagtaca tcaagtgtat catatgccaa gtacgccccc      300
tattgacgtc aatgacggta aatggcccgc ctggcattat gcccagtaca tgaccttatg      360
ggactttcct acttggcagt acatctacgt attagtcatc gctattacca tggtgatgcg      420
gttttggcag tacatcaatg ggcgtggata gcggtttgac tcacggggat ttccaagtct      480
ccaccccatt gacgtcaatg ggagtttgtt ttggcaccaa aatcaacggg actttccaaa      540
atgtcgtaac aactccgccc cattgacgca aatgggcggt aggcgtgtac ggtgggaggt      600
ctatataagc agagctctct ggctaactag agaacccact gcttactggc ttatcgaaat      660
taatacgact cactataggg agacccaagc tagcttggta ccgggccgac ctcaccatgg      720
gatggagctg tatcatcctc ttcttggtag caacagctac aggtaagggg ctcacagtag      780
caggcttgag gtctggacat atatatgggt gacaatgaca tccactttgc ctttctctcc      840
acaggtgtgc attccgaagt gaagctggag gagtctggag gcggcttggt gcaacctgga      900
ggctccatga aactctcctg tgttgcctct ggattcattt tcagtaacca ctggatgaac      960
tgggtccgcc agtctccaga aggggcttt  gaatggggttg ctgaaattag atcaaaatcc     1020
attaattctg caacacatta tgccgagtct gtgaaaggga ggttcaccat ctcaagagat      1080
gattccaaaa gtgctgtgta cctgcaaatg accgacctga aactgaagga cactggcgtt      1140
tattactgtt ccaggaatta ctacggtagt acctacgact actggggcca aggcaccact      1200
```

```
ctcacagtgt cctcaggtga gtcgtacgct agcaagcttg atgacctggg ctgagctgga    1260
ctaagctggg ctgacctggg ctgggatggg atgggctagg atgacttggg ctggactggg    1320
cgggactgag ctggactggc ctgggctgag ctgggctggg ctggactgag ctggactggc    1380
ctgggctggg ctgggcggga tgggctgagg tggctgctaa tgtgggaaag aggccgtggg    1440
ttgagtgtga ttccacctgc agagccctga gcccagctgt gttcttaggg gttctgaggg    1500
ccacgcagct ctgttgcacc atgattctgt cttctctctt gcccactgcc tgaaggaaat    1560
ttggagtggg ctgggcccag agctcccctg tatagcaggc cctgtcctgg agggcctggc    1620
agggacatgc cttagcctgt tggcctctag tcccgagacc tcataggcca caggggtcca    1680
ctgtggcttg tttgggcctg ggtgggggct catggagtgg tgggtgttgg actgagactc    1740
tgaccaggga caggggatg gggtcacagc caagccactc caccctacc ccatgcacac      1800
agcactcaga gcccagaccc tctcctaaga gcccccacca aaatcctctc taggggcagg    1860
ggatagagca agacatgtcc cccacccaga gcagggctg cggtcaggga gctcagggga     1920
ctcagccact ccatggcaga gccctgtta atacaacttg tgtctgggat ggcctggatc     1980
agagaccta tctaaggagc atgttcagaa accatgttgc tgggatcaga cagcagggtc     2040
caactgcagg cctgtggtgc aggagctgtg tgaccatggg gctgtcacca ggcctctctg    2100
tgctgggttc ctccagtata gaggagaggc agtatagagg agaggccgc gtcctcacag     2160
tgcattctgt gttccagcat ccccgaccag ccccaaggtc ttcccgctga gcctctgcag    2220
cacccagcca gatgggaacg tggtcatcgc ctgcctggtc cagggcttct tccccccagga   2280
gccactcagt gtgacctgga gcgaaagcgg acagggcgtg accgccagaa acttcccacc    2340
cagccaggat gcctccgggg acctgtacac cacgagcagc cagctgaccc tgccggccac    2400
acagtgccta gccggcaagt ccgtgacatg ccacgtgaag cactacacga atcccagcca    2460
ggatgtgact gtgccctgcc caggtcagag ggcaggctgg ggagtggggc ggggccaccc    2520
cgtcgtgccc tgacactgcg cctgcacccg tgttccccac agggagccgc cccttcactc    2580
acaccagagt ggaccgcggg ccgagcccca ggaggtggtg gtggacaggc caggaggggc    2640
gaggcggggg catgggaag tatgtgctga ccagctcagg ccatctctcc actccagttc     2700
cctcaactcc acctacccca tctccctcaa ctccacctac cccatctccc tcatgctgcc    2760
acccccgact gtcactgcac cgaccggccc tcgaggacct gctcttaggt tcagaagcga    2820
acctcacgtg cacactgacc ggcctgagag atgcctcagg tgtcaccttc acctggacgc    2880
cctcaagtgg gaagagcgct gttcaaggac cacctgagcg tgacctctgt ggctgctaca    2940
gcgtgtccag tgtcctgccg ggctgtgccg agccatggaa ccatgggaag accttcactt    3000
gcactgctgc ctaccccgag tccaagaccc cgctaaccgc cacctctca aaatccggtg     3060
ggtccagacc ctgctcgggg ccctgctcag tgctctggtt tgcaaagcat attcctggcc    3120
tgcctcctcc ctcccaatcc tgggctccag tgctcatgcc aagtacagag ggaaactgag    3180
gcaggctgag gggccaggac acagcccggg gtgcccacca gagcagaggg gctctctcat    3240
cccctgccca gcccctgac ctggctctct accctccagg aaacacattc cggcccgagg     3300
tccacctgct gccgccgccg tcggaggagc tggccctgaa cgagctggtg acgctgacgt    3360
gcctggcacg cggcttcagc cccaaggacg tgctggttcg ctggctgcag ggtcacagg    3420
agctgccccg cgagaagtac ctgacttggg catcccggca ggagcccagc cagggcacca    3480
ccaccttcgc tgtgaccagc atactgcgcg tggcagccga ggactggaag aagggggaca    3540
```

```
ccttctcctg catggtgggc cacgaggccc tgccgctggc cttcacacag aagaccatcg    3600
accgcttggc gggtaaaccc acccatgtca atgtgtctgt tgtcatggcg gaggtggacg    3660
gcacctgcta ctgagccgcc cgcctgtccc caccccctgaa taaactccat gctcccccaa   3720
gcagccccac gcttccatcc ggcgcctgtc tgtccatcct cagggtctca gcacttggga    3780
aagggccagg gcatggacag ggaagaatac cccctgccct gagcctcggg gggcccctgg    3840
caccccatg agactttcca ccctggtgtg agtgtgagtt gtgagtgtga gagtgtgtgg    3900
tgcaggaggc ctcgctggtg tgagatccac tagttctaga ggatctcccg atcccctatg    3960
gtgcactctc agtacaatct gctctgatgc cgcatagtta agccagtatc tgctccctgc    4020
ttgtgtgttg gaggtcgctg agtagtgcgc gagcaaaatt taagctacaa caaggcaagg    4080
cttgaccgac aattaattgc atgaagaatc tgcttagggt taggcgtttt gcgctgcttc    4140
gcgatgtacg ggccagatat acgcgttgac attgattatt gactagttat taatagtaat    4200
caattacggg gtcattagtt catagcccat atatggagtt ccgcgttaca taacttacgg    4260
taaatggccc gcctggctga ccgcccaacg accccgccc attgacgtca ataatgacgt    4320
atgttcccat agtaacgcca tagggactt tccattgacg tcaatgggtg gagtatttac    4380
ggtaaactgc ccacttggca gtacatcaag tgtatcatat gccaagtacg ccccctattg    4440
acgtcaatga cggtaaatgg cccgcctggc attatgccca gtacatgacc ttatgggact    4500
ttcctacttg gcagtacatc tacgtattag tcatcgctat taccatggtg atgcggtttt    4560
ggcagtacat caatgggcgt ggatagcggt ttgactcacg gggatttcca agtctccacc    4620
ccattgacgt caatgggagt ttgttttggc accaaaatca acgggacttt ccaaaatgtc    4680
gtaacaactc cgccccattg acgcaaatgg gcggtaggcg tgtacggtgg gaggtctata    4740
taagcagagc tctctggcta actagagaac ccactgctta ctggcttatc gaaattaata    4800
cgactcacta tagggagacc caagctagct tggtaccggg ccgacctcac catgggatgg    4860
agctgtatca tcctcttctt ggtagcaaca gctacaggta aggggctcac agtagcaggc    4920
ttgaggtctg acatatata tgggtgacaa tgacatccac tttgcctttc tctccacagg    4980
tgtgcattcc gacatcttgc tgactcagtc tccagccatc ctgtctgtga gtccaggaga    5040
aagagtcagt ttctcctgta gggccagtca gttcgttggc tcaagcatcc actggtatca    5100
gcaaagaaca atggttctc caaggcttct cataaagtat gcttctgagt ctatgtctgg    5160
catccctagc agatttagtg gcagtggatc agggacagat tttactctta gcatcaacac    5220
tgtggagtct gaagatattg cagattatta ctgtcaacaa agtcattcct ggccattcac    5280
gttcggcagc gggacaaatt tggaagtgaa acgtgagtag aacgtacgct agcaagcttg    5340
atatcgaatt ctaaactctg aggggggtcgg atgacgtggc cattctttgc ctaaagcatt    5400
gagtttactg caaggtcaga aaagcatgca aagccctcag aatggctgca aagagctcca    5460
acaaaacaat ttagaacttt attaaggaat aggggggaagc taggaagaaa ctcaaaacat    5520
caagattta aatacgcttc ttggtctcct tgctataatt atctgggata gcatgctgt    5580
tttctgtctg tccctaacat gccctgtgat tatccgcaaa caacacaccc aagggcagaa    5640
ctttgttact aaacaccat cctgtttgct tctttcctca ggaactgtgg ctgcaccatc    5700
tgtcttcatc ttcccgccat ctgatgagca gttgaaatct ggaactgcct ctgttgtgtg    5760
cctgctgaat aacttctatc ccagagaggc caaagtacag tggaaggtgg ataacgccct    5820
ccaatcgggt aactcccagg agagtgtcac agagcaggac agcaaggaca gcacctacag    5880
cctcagcagc accctgacgc tgagcaaagc agactacgag aaacacaaag tctacgcctg    5940
```

```
cgaagtcacc catcagggcc tgagctcgcc cgtcacaaag agcttcaaca ggggagagtg    6000
ttagagggag aagtgccccc acctgctcct cagttccagc ctgacccccct cccatccttt   6060 ggcctctgac ccttttttcca caggggacct accccctattg cggtcctcca gctcatcttt  6120
cacctcaccc ccctcctcct ccttggcttt aattatgcta atgttggagg agaatgaata    6180
aataaagtga atctttgcac ctgtggtttc tctctttcct catttaataa ttattatctg    6240
ttgttttacc aactactcaa tttctcttat aagggactaa atatgtagtc atcctaaggc    6300
gcataaccat ttataaaaat catccttcat tctattttac cctatcatcc tctgcaagac    6360
agtcctccct caaacccaca agccttctgt cctcacagtc ccctgggcca tggtaggaga    6420
gacttgcttc cttgttttcc cctcctcagc aagccctcat agtcctttt aagggtgaca     6480 ggtcttacag tcatatatcc tttgattcaa ttccctgaga atcaaccaaa gcaaattcct    6540
gcagcccggg ggatccacta gtaacggccg ccagtgtgct ggaattctgc agatatccat    6600
cacactggcg gccgctcgag catgcatcta gagggcccta ttctatagtg tcacctaaat    6660
gctagagctc gctgatcagc ctcgactgtg ccttctagtt gccagccatc tgttgtttgc    6720 ccctccccccg tgccttcctt gaccctggaa ggtgccactc ccactgtcct ttcctaataa   6780
aatgaggaaa ttgcatcgca ttgtctgagt aggtgtcatt ctattctggg gggtggggtg    6840
gggcaggaca gcaaggggga ggattgggaa gacaatagca ggcatgctgg ggatgcggtg    6900
ggctctatgg                                                           6910

<210> SEQ ID NO 29
<211> LENGTH: 711
<212> TYPE: DNA
<213> ORGANISM: Artificial Sequence
<220> FEATURE:
<223> OTHER INFORMATION: DNA sequence for infliximab light chain
      optimized for maize.

<400> SEQUENCE: 29
atgaagtacc tgctgcccac cgctgctgct ggcctgctgc tgctcgctgc ccagcccgct     60
atggccgaca tcctgctgac ccagtccccc gccatcctgt ccgtgtcccc aggcgagcgc    120
gtgtccttct cctgccgcgc ctcccagttc gtgggctcct ccatccactg gtatcagcag    180
cgcaccaacg gctcccccag gctgctgatc aagtacgcct ccgagtccat gtccggcatc    240
ccgtccaggt tctccggctc cggcagcggc accgacttca cccttgtccat caacaccgtg   300 gagtccgagg acatcgccga ctactactgc cagcagtccc actcctggcc cttcaccttc    360
ggctccggca ccaacctcga ggtgaagcgt acggtggctg ccccctccgt gttcatcttc    420 ccccctccg acgagcagct gaagtccggc accgcctccg ttgtctgcct ccttaacaac     480
ttctaccccc gcgaggccaa ggtccagtgg aaggtggaca acgccctcca gtccggcaac    540
tcccaggagt ccgtcaccga gcaggactcc aaggacagca cctactccct gtcctccacc    600
ctgaccctgt ccaaggccga ctacgagaag cacaaggtgt acgcctgcga ggtgacccac    660
cagggcctgt cctcccccgt caccaagtcc ttcaaccgcg gcgagtgctg a             711

<210> SEQ ID NO 30
<211> LENGTH: 3092
<212> TYPE: DNA
<213> ORGANISM: Artificial Sequence
<220> FEATURE:
<223> OTHER INFORMATION: DNA sequence for SC- and J-chains optimized for
      HEK.
```

```
<400> SEQUENCE: 30
gcttcgcgat gtacgggcca gatatacgcg ttgacattga ttattgacta gttattaata      60
gtaatcaatt acggggtcat tagttcatag cccatatatg gagttccgcg ttacataact     120
tacggtaaat ggcccgcctg gctgaccgcc caacgacccc cgcccattga cgtcaataat     180
gacgtatgtt cccatagtaa cgccaatagg gactttccat tgacgtcaat gggtggagta     240
tttacggtaa actgcccact tggcagtaca tcaagtgtat catatgccaa gtacgccccc     300
tattgacgtc aatgacggta aatggcccgc ctggcattat gcccagtaca tgaccttatg     360
ggactttcct acttggcagt acatctacgt attagtcatc gctattacca tggtgatgcg     420
gttttggcag tacatcaatg ggcgtggata gcggtttgac tcacggggat ttccaagtct     480
ccacccatt gacgtcaatg ggagtttgtt ttggcaccaa aatcaacggg actttccaaa     540
atgtcgtaac aactccgccc cattgacgca atgggcggt aggcgtgtac ggtgggaggt     600
ctatataagc agagctctct ggctaactag agaacccact gcttactggc ttatcgaaat     660
taatacgact cactataggg agacccaagc tagcttggta ccgggccgac ctcaccatga     720
agaaccacct gctgttctgg ggcgtgctgg ccgtgttcat caaggccgtg cacgtgaagg     780
ctcaggagga tgagcgcatc gtcctcgtgg acaacaagtg caagtgcgcc cgcatcacct     840
cccgcatcat ccgctcctcc gaggacccca acgaggacat cgtggagcgc aacatccgca     900
tcatcgtgcc cctgaacaac gcgagaaca tctccgaccc cacctccccc ctgaggaccc     960
gcttcgtgta ccacctgtcc gacctgtgca agaagtgcga ccccaccgag gtggagctgg    1020
acaaccagat cgtgaccgcc acccagtcca acatctgcga cgaggactcc gccaccgaga    1080
cctgctacac ctacgaccgc aacaagtgct acaccgccgt ggtgcccctg gtgtacggcg    1140
gcgagaccaa gatggtggag accgccctga ccccgacgc ttgctacccc gactgataat    1200
ctagaggatc tcccgatccc ctatggtgca ctctcagtac aatctgctct gatgccgcat    1260
agttaagcca gtatctgctc cctgcttgtg tgttggaggt cgctgagtag tgcgcgagca    1320
aaatttaagc tacaacaagg caaggcttga ccgacaatta attgcatgaa gaatctgctt    1380
agggttaggc gttttgcgct gcttcgcgat gtacgggcca gatatacgcg ttgacattga    1440
ttattgacta gttattaata gtaatcaatt acggggtcat tagttcatag cccatatatg    1500
gagttccgcg ttacataact tacggtaaat ggcccgcctg gctgaccgcc caacgacccc    1560
cgcccattga cgtcaataat gacgtatgtt cccatagtaa cgccaatagg gactttccat    1620
tgacgtcaat gggtggagta tttacggtaa actgcccact tggcagtaca tcaagtgtat    1680
catatgccaa gtacgccccc tattgacgtc aatgacggta aatggcccgc ctggcattat    1740
gcccagtaca tgaccttatg ggactttcct acttggcagt acatctacgt attagtcatc    1800
gctattacca tggtgatgcg gttttggcag tacatcaatg ggcgtggata gcggtttgac    1860
tcacggggat ttccaagtct ccacccatt gacgtcaatg ggagtttgtt ttggcaccaa    1920
aatcaacggg actttccaaa atgtcgtaac aactccgccc cattgacgca atgggcggt    1980
aggcgtgtac ggtgggaggt ctatataagc agagctctct ggctaactag agaacccact    2040
gcttactggc ttatcgaaat taatacgact cactataggg agacccaagc tagcttggta    2100
ccgggccgac ctcaccatga agtacctgct gcccaccgct gctgctggcc tgctgctgct    2160
cgctgcccag cccgctatgg ccgacatcct gctgacccag tccccgcca tcctgtccgt    2220
gtccccaggc gagcgcgtgt ccttctcctg ccgcgcctcc cagttcgtgg gctcctccat    2280
ccactggtat cagcagcgca ccaacggctc ccccaggctg ctgatcaagt acgcctccga    2340
```

```
gtccatgtcc ggcatcccgt ccaggttctc cggctccggc agcggcaccg acttcaccct    2400
gtccatcaac accgtggagt ccgaggacat cgccgactac tactgccagc agtcccactc    2460
ctggcccttc accttcggct ccggcaccaa cctcgaggtg aagcgtacgg tggctgcccc    2520
ctccgtgttc atcttccccc cctccgacga gcagctgaag tccggcaccg cctccgttgt    2580
ctgcctcctt aacaacttct accccgcga ggccaaggtc cagtggaagg tggacaacgc    2640
cctccagtcc ggcaactccc aggagtccgt caccgagcag gactccaagg acagcaccta    2700
ctccctgtcc tccaccctga ccctgtccaa ggccgactac gagaagcaca aggtgtacgc    2760
ctgcgaggtg acccaccagg gcctgtcctc ccccgtcacc aagtccttca accgcggcga    2820
gtgctgataa tctagagggc cgtttaaac ccgctgatca gcctcgactg tgccttctag    2880
ttgccagcca tctgttgttt gcccctcccc cgtgccttcc ttgaccctgg aaggtgccac    2940
tcccactgtc ctttcctaat aaaatgagga aattgcatcg cattgtctga gtaggtgtca    3000
ttctattctg gggggtgggg tggggcagga cagcaagggg gaggattggg aagacaatag    3060
caggcatgct ggggatgcgg tgggctctat gg                                   3092
```

<210> SEQ ID NO 31
<211> LENGTH: 1515
<212> TYPE: DNA
<213> ORGANISM: Artificial Sequence
<220> FEATURE:
<223> OTHER INFORMATION: DNA sequence for adalimumab heavy chain IgA1
      optimized for Lemna.

<400> SEQUENCE: 31

```
atgcaggtcc tgaacacgat ggtcaacaag cacttcctct ccctgtccgt cctcatcgtc      60
ctcctcgggc tgagcagcaa cctcaccgcc ggcgaggtcc agctggtgga gtccggcggg     120
ggcctggtcc agcccggcg ctccctgcgc ctcagctgcg cggccagcgg cttcaccttc      180
gacgattacg ccatgcactg ggtcagacag gccccgggga agggcctcga gtgggtgtcc     240
gccatcactt ggaacagcgg ccacatcgac tacgccgact ccgtggaggg gcggttcacg     300
atcagccggg acaacgccaa gaactccctg tacctgcaga tgaactccct cagagcggag     360
gacactgcgg tctactattg cgccaaggtg agctacctga gcaccgcgtc cagcttggac     420
tactgggggc agggcaccct ggtgacgtg tcctcagcct cgcccacgtc gccgaaggtc      480
ttccccctca gcctctgctc gacgcagccc gacgggaacg ttgtcatcgc ctgcctcgtg     540
cagggcttct ccccgcagga gccgctctcc gtgacctggt ccgagagcgg ccagggcgtt     600
accgctcgga acttcccgcc ctcccaggac gcgagcggcg atctctacac tacgtcctcg     660
cagcttacgc tccggcgac gcaatgcctc gccggcaaga gcgtgacgtg ccacgtcaag     720
cactacacca atcctcgca ggacgtgacc gtgccctgcc cggtgccttc cacgcctccg      780
acgccgagcc cgtccacgcc gccgacccct cgcccagct gctgtcaccc gcgcctctcc      840
ctccaccggc ccgccctgga ggacctgttg ctcgggagca ggcgaacct cacctgcacg      900 ctcacgggcc tgcgcgacgc ctctggcgtt accttcacct ggacgcccts ttccgggaag     960
agcgccgtgc agggcccgcc cgagagagac tctgcggtt gctactccgt gtcgagcgtg    1020
ctcccggggt gcgcggagcc gtggaaccac gggaagacct tcacctgcac cgcggcctac    1080
cctgagtcca agacgcccct gaccgccacc ctgtccaagt ccgggaacac cttccgcccg    1140
gaggtgcact gctgccacc gcccagcgag gaactcgccc tgaacgagct ggtcacgctc    1200
acctgcctgg ctaggggctt ctcgcccaag gacgtgctgg tccgctggtt gcaaggcagc    1260
```

-continued

```
caggagctgc cgcgcgagaa gtacctcacc tgggcctcta ggcaggagcc ctcgcagggc    1320
accactacgt tcgcggtgac ctccatcctc agggtcgccg ctgaggactg aagaaaggc     1380 gacaccttct cctgcatggt cggccacgag gcgctgcccc tcgccttcac ccagaagacc    1440
atcgaccggc tggccgggaa gcccacccac gtcaacgtca gcgtcgttat ggctgaggtt    1500
gacgggacgt gctac                                                     1515
```

<210> SEQ ID NO 32
<211> LENGTH: 735
<212> TYPE: DNA
<213> ORGANISM: Artificial Sequence
<220> FEATURE:
<223> OTHER INFORMATION: DNA sequence for adalimumab light chain kappa
      optimized for Lemna.

<400> SEQUENCE: 32

```
atgcaggtcc tgaacacgat ggtcaacaag cacttcctct ccctgtccgt cctcatcgtc     60
ctcctcgggc tgagcagcaa cctcaccgcc ggcgacatcc agatgacgca gagcccgtcg    120
agcctgtccg cctccgtcgg ggacagggtc acgatcacct gcagagccag ccagggcatc    180
cgcaactacc tggcctggta tcaacagaag cccgggaagg ctccgaagct cctgatctac    240
gcggccagca ccctccagag cggcgtcccg agccggttct ccggcagcgg ctccggcacc    300
gacttcaccc tcaccatcag ctcgctccag cccgaggacg tcgccaccta ctactgccag    360
aggtacaacc gcgcgccgta cacgttcggg cagggcacga aggtggagat caagcgcacg    420
gtggccgcgc ccagcgtctt catcttcccg ccctcggacg agcagctgaa gtccggcact    480
gcctccgtgg tctgcctgct caacaacttc taccccgcg aagccaaggt gcagtggaag    540
gttgacaacg cgctccagag cgggaactcc caggagtccg tgaccgagca ggactccaag    600 gactccaccct acagcctgtc cagcaccctc accctctcca aggccgacta cgagaagcac    660
aaggtgtacg cctgcgaggt gacccaccag ggcctctcct cccgggtgac caagtccttc    720
aaccgcggtg agtgc                                                     735
```

<210> SEQ ID NO 33
<211> LENGTH: 480
<212> TYPE: DNA
<213> ORGANISM: Artificial Sequence
<220> FEATURE:
<223> OTHER INFORMATION: DNA sequence for J-chain optimized for maize.

<400> SEQUENCE: 33

```
atgaagaacc acctgctgtt ctggggcgtg ctggccgtgt tcatcaaggc cgtgcacgtg     60
aaggctcagg aggatgagcg catcgtcctc gtggacaaca gtgcaagtg cgcccgcatc    120 acctcccgca tcatccgctc ctccgaggac cccaacgagg acatcgtgga gcgcaacatc    180
cgcatcatcg tgcccctgaa caaccgcgag aacatctccg accccacctc cccctgaagg    240
acccgcttcg tgtaccacct gtccgacctg tgcaagaagt gcgaccccac cgaggtggag    300
ctggacaacc agatcgtgac cgccacccag tccaacatct gcgacgagga ctccgccacc    360
gagacctgct acacctacga ccgcaacaag tgctacaccg ccgtggtgcc cctggtgtac    420
ggcggcgaga ccaagatggt ggagaccgcc ctgacccccg acgcttgcta ccccgactga    480
```

<210> SEQ ID NO 34
<211> LENGTH: 504
<212> TYPE: DNA
<213> ORGANISM: Artificial Sequence

```
<220> FEATURE:
<223> OTHER INFORMATION: DNA sequence for J-chain optimized for Lemna.

<400> SEQUENCE: 34
atgcaggtcc tgaacacgat ggtcaacaag cacttcctct ccctgtccgt cctcatcgtc      60
ctcctcgggc tgagcagcaa cctcaccgcc ggccaggagg acgagcgcat cgtcctcgtg     120
gacaacaagt gcaagtgcgc gcgcatcacc agccgcatca tccggtccag cgaggacccc     180
aacgaggaca tcgtcgagcg caacatccgc atcatcgtgc ccctgaacaa ccgcgagaac     240
atctccgacc cgacctcccc gctgaggacc cgcttcgtgt accacctgag cgacctctgc     300
aagaagtgcg accccaccga ggtggaactc gacaaccaga tcgtcacggc cacccagagc     360
aacatctgcg acgaggactc cgccaccgag acgtgctaca cctacgacag gaacaagtgc     420
tacacggccg tcgtgccccct cgtgtacggc ggggagacca agatggtcga cacggccctg     480 acccccggacg cgtgctaccc cgac                                           504

<210> SEQ ID NO 35
<211> LENGTH: 1818
<212> TYPE: DNA
<213> ORGANISM: Artificial Sequence
<220> FEATURE:
<223> OTHER INFORMATION: DNA sequence for SC-chain optimized for maize.

<400> SEQUENCE: 35
atggctatgc tgctgttcgt gctgacctgc ctgctggccg tgttccccgc catctccacc      60
aagtccccca tcttcggccc cgaggaggtg aactccgtgg agggcaactc cgtgtccatc     120
acctgctact accccccccac ctccgtgaac cgccacacta ggaagtactg gtgcaggcag     180
ggcgctaggg gcggctgcat cacccctgatc tcctccgagg gctacgtttc tagcaagtac     240
gctggcaggg ccaacctgac caacttcccc gagaacggca ccttcgtggt gaacatcgcc     300
cagctgtccc aggacgactc cggccgctac aagtgcggcc tgggcatcaa ctccagggggc     360 ctgtccttcg acgtgtccct cgaggtgtcc cagggcccag gcctgctgaa cgacaccaag     420
gtgtacaccg tggaccctcgg tcgcaccgtc accatcaact gcccccttcaa gaccgagaac     480 gcccagaagc gcaagtccct gtacaagcag atcggcctgt accccgtgct ggtgatcgac     540
tcctccggct acgtgaaccc caactacacc ggccgcatcc gcctggacat ccagggcact     600
ggccagctgc tgttctccgt ggtgatcaac cagctgcgcc tgtccgatgc tggccaatac     660
ctgtgccaag ctggcgacga ctccaactcc aacaagaaga cgccgaccct ccaggtgctg     720
aagcccgagc ccgagctggt gtacgaggac ctgcgcggct ccgtgacctt ccactgcgct     780
ctgggccccg aggtggcgaa cgttgcgaag ttcctctgca ggcagtcctc cggcgagaac     840
tgcgacgtgg tggtgaacac cctgggcaag cgcgctcccg ctttcgaggg ccgcatcctg     900 ctgaacccccc aggacaagga cggctccttc tccgtcgtca tcaccggcct gcgcaaggag     960
gacgctggcc gctacctctg cggcgctcac tccgacggcc agctccagga gggctccccc    1020
atccaggcct ggcagctgtt cgtgaacgag gagtccacca tccccaggtc cccaccgtg     1080 gtgaagggcg tggctggcgg ctccgtggct gtgctgtgcc cctacaaccg caaggagtcc    1140
aagtccatca gtactggtg cctgtgggag ggcgctcaga acggcaggtg ccccctgctc    1200
gtggactccg agggctgggt gaaggcccag tacgagggca ggctgtccct gctcgaggag    1260
cccggcaacg gcaccttcac cgtgatcctg aaccagctga cctcccgcga cgccggcttc    1320
tactggtgcc tcaccaacgg cgacaccctg tggaggacca ccgtggagat caagatcatc    1380
```

```
gagggcgagc ccaacctgaa ggtcccaggg aacgtgaccg ctgtgctggg cgagaccctg    1440
aaggtcccct gccacttccc ctgcaagttc tcctcctacg agaagtactg gtgcaagtgg    1500
aacaacaccg gctgccaggc tctgccctcc caggacgagg gccccctccaa ggccttcgtg   1560 aactgcgacg agaactcccg cctggtgtcc ctgaccctga acctggtgac cagggccgac    1620
gagggctggt actggtgcgg cgtgaagcag ggccacttct acggcgagac cgccgctgtg    1680
tacgtggccg tggaggagag gaaggccgct ggctctaggg atgtttctct tgccaaggct    1740
gacgctgccc ccgacgagaa ggtgctggac tccggcttcc gcgagatcga gaacaaggcc    1800
atccaggacc cccgctga                                                  1818

<210> SEQ ID NO 36
<211> LENGTH: 1848
<212> TYPE: DNA
<213> ORGANISM: Artificial Sequence
<220> FEATURE:
<223> OTHER INFORMATION: DNA sequence for SC-chain optimized for Lemna.

<400> SEQUENCE: 36
atgcaggtcc tgaacacgat ggtcaacaag cacttcctct ccctgtccgt cctcatcgtc     60
ctcctcgggc tgagcagcaa cctcaccgcc ggcaagtccc cgatcttcgg gccggaggaa    120
gtgaactcgg tggaggggaa ctccgtcagc atcacctgct actatcctcc gacgagcgtg    180
aaccggcaca cgaggaagta ctggtgcagg caaggggcca gaggcgggtg catcacccct    240
atctccagcg aggggtacgt ctcgtccaag tacgccggtc gcgccaacct cacgaacttc    300
cccgagaacg gacgttcgt tgtgaacatc gcccagctgt cgcaggacga cagcggccgc    360
tacaagtgtg gcctcgggat caacagccgc gggctctcct tcgacgtctc gctggaggtg    420
tcccagggcc ccgcctcct gaacgacacg aaagtgtaca ccgttgacct cggccggacg    480
gtcactatca actgcccgtt caagaccgag aacgcccaga agcgcaagag cctctacaag    540
cagatcggcc tctacccgt cctggtgatc gactcctcgg gctacgtcaa cccgaactac    600
accggccgca tccggctgga catccagggg accgggcagc tgctcttctc cgtggtcatc    660
aaccagctcc gcctgagcga cgccgggcag tacctgtgcc aggccgggga cgatagcaac    720
tccaacaaga agaacgccga cctccaagtg ctgaagcccg agccggagct ggtctacgag    780
gacctccgcg gtccgtgac cttccactgc gccctgggcc cggaggtcgc caacgtggcg    840
aagttcctgt gccggcagtc ctcgggtgag aactgcgacg tggtcgtgaa caccctcggg    900
aagcgcgcgc ccgccttcga gggccgcatc ctgctcaatc cccaggacaa ggacgggtcc    960
ttcagcgtgg tcatcacggg cctccgcaag gaagacgcgg gccgctacct ctgcggcgcc   1020
cactcggacg gccagctcca ggaggggagc cccatccagg cctggcagct gttcgtcaac   1080
gaggagtcca cgatccccag aagccccacc gtggttaagg gcgtcgccgg tggctccgtg   1140
gcggtgctgt gcccgtacaa ccgcaaggag agcaagtcca tcaagtactg gtgcctgtgg   1200
gagggcgccc agaacgggag atgcccgctc ctggtggact ccgaggggtg ggtgaaggcg   1260
cagtacgagg gccgcctctc gctcctggag gagcccggca acggcacctt caccgtcatc   1320
ctcaaccagc tgacgtcgcg ggacgccggc ttctactggt gcctcaccaa cggcgacacc   1380
ctctggagga ccacggtgga gatcaagatc atcgagggcg agccgaacct gaaagtccct   1440
gggaacgtga ccgctgtcct cggcgagacc ctgaaggtgc cctgccactt cccctgcaag   1500
ttctccagct acgagaagta ctggtgcaag tggaacaaca ccggctgtca ggccctcccc   1560
tcgcaggacg aggggccgtc caaggcgttc gtgaactgcg acgagaacag ccgcctcgtg   1620
```

```
tccctcaccc tcaacctcgt gacccgcgcc gacgagggct ggtactggtg cggggtgaag    1680
cagggccact tctacgggga gaccgccgcg gtctacgtgg cggtcgagga gcgcaaggcc    1740
gctggctccc gcgacgtcag cctggccaag gccgacgccg cgcccgacga gaaggtgctg    1800
gactccgggt tccgggagat cgagaacaag gccatccagg atccccgg                1848
```

ANTI-TNF ALPHA MONOCLONAL SECRETORY IGA ANTIBODIES AND METHODS FOR TREATING INFLAMMATORY DISEASES

This application claims the benefit of priority under 35 U.S.C. §119(e) from U.S. provisional patent application Ser. No. 61/576,727, filed Dec. 16, 2011, and Ser. No. 61/576,922, filed Dec. 16, 2011; the entire contents of each provisional application being incorporated herein by reference.

FIELD OF THE INVENTION

The present invention relates to monoclonal secretory IgA antibodies, which bind to and neutralize human TNFα. The antibodies are useful in treating inflammatory diseases in humans, including by oral administration.

BACKGROUND OF THE INVENTION

Inflammation represents a key event of many diseases, such as psoriasis, inflammatory bowel diseases, rheumatoid arthritis, asthma, multiple sclerosis, atherosclerosis, cystic fibrosis, and sepsis. Inflammatory cells, such as neutrophils, eosinophils, basophils, mast cells, macrophages, endothelial cells, and platelets, respond to inflammatory stimuli and foreign substances by producing bioactive mediators. These mediators act as autocrines and paracrines by interacting with many cell types to promote the inflammatory response. There are many mediators that can promote inflammation, such as cytokines and their receptors, adhesion molecules and their receptors, antigens involved in lymphocyte activation, and IgE and its receptors.

Cytokines, for example, are soluble proteins that allow for communication between cells and the external environment. The term cytokines includes a wide range of proteins, such as lymphokines, monokines, interleukins, colony stimulating factors, interferons, tumor necrosis factors, and chemokines. Cytokines serve many functions, including controlling cell growth, migration, development, and differentiation, and mediating and regulating immunity, inflammation, and hematopoiesis. Even within a given function, cytokines can have diverse roles. For example, in the context of mediating and regulating inflammation, some cytokines inhibit the inflammatory response (anti-inflammatory cytokines), others promote the inflammatory response (pro-inflammatory cytokines). And certain cytokines fall into both categories, i.e., can inhibit or promote inflammation, depending on the situation. The targeting of proinflammatory cytokines to suppress their natural function, such as with antibodies, is a well-established strategy for treating various inflammatory diseases.

TNFα (Tumor Necrosis Factor alpha) is a cytokine which promotes an inflammatory response and is involved in several inflammatory and autoimmune diseases or disorders. Binding TNFα has been proposed as a strategy for providing various diagnostic and therapeutic effects. For example, U.S. Pat. No. 5,075,236 teaches forming murine anti-TNFα antibodies by a hybridoma method. The anti-TNFα antibodies can be used in an assay to detect Kawasaki Disease.

A line of patents including U.S. Pat. No. 5,656,272, U.S. Pat. No. 5,919,452, and U.S. Pat. No. 6,790,444 relate to treating TNF-α-mediated diseases using an anti-TNFα antibody or peptide. The antibody is preferably a monoclonal chimeric antibody known as cA2. The A2 refers to a murine antibody that effectively binds human TNFα. The antigen binding region of A2 is combined with the constant region of a human IgG1 to make a chimeric antibody designated cA2. The diseases to be treated include rheumatoid arthritis, Crohn's disease, ulcerative colitis, psoriasis, etc. The chimeric antibody cA2 has been commercialized under the name infliximab and is sold under the brand name REMICADE® (Centocor Ortho Biotech Inc).

U.S. Pat. No. 5,605,690 relates to a TNFα receptor polypeptide that binds TNFα. A recombinant chimeric antibody can be formed using the receptor sequence in place of the variable domain of the heavy and/or light chain. Human IgG1 is suggested for the constant regions. A chimeric antibody containing a combination of the TNFα receptor linked to an Fc portion of an IgG1 has been commercialized under the name etanercept, which is sold under the brand name ENBREL® (Immunex Corporation). Etanercept is approved to treat rheumatoid arthritis and plaque psoriasis.

U.S. Pat. No. 6,090,382 relates to human antibodies, or the antigen binding portions thereof, that bind human TNFα. The heavy chain constant regions of the human antibody can be IgG1, IgG2, IgG3, IgG4, IgA, IgE, IgM, or IgD and preferably is IgG1 or IgG4. The antibodies are taught to be useful in treating a variety of conditions including autoimmune (e.g., rheumatoid arthritis, multiple sclerosis) and intestinal disorders (e.g., Crohn's disease, IBD, ulcerative colitis). The preferred IgG1 antibody has been commercialized under the name adalimumab and is sold under the brand name HUMIRA® (Abbott Laboratories).

U.S. Pat. No. 7,012,135 and U.S. Pat. No. 7,186,820 relate to an antibody or fragment thereof that specifically binds TNFα wherein the variable domain region comprises specified CDR sequences. The constant region domains, when present, may be human IgA, IgD, IgE, IgG, or IgM domains, with IgG being preferred. A PEGylated modified Fab fragment has been commercialized as certolizumab pegol and sold under the brand name CIMZIA® (UCB Group of Companies) and is approved for treating rheumatoid arthritis and Crohn's disease.

Published U.S. application 2009/214528 shows the production of another anti-TNFα antibody known as golimumab and sold under the brand name SIMPONI® (Centocor Ortho Biotech Inc.). Golimumab is a fully human monoclonal antibody directed to TNFα. It is approved for treating rheumatoid arthritis.

The currently approved anti-TNFα antibodies are IgG-based. And these compounds are administered systemically to a patient via multiple injections or infusions (e.g., multiple intravenous or subcutaneous injections). See Reimund, J-M et al., Inflammation Allergy Drug Discovery 1, 21-34 (2007). These IgG-based anti-TNFα compounds, however, suffer from one or more undesirable effects. For example, it has been reported that REMICADE® infliximab; a chimeric IgG1κ monoclonal antibody specific for TNFα) is associated with hypersensitivity reactions in the patient, likely due to the non-human portions of the REMICADE® antibodies. Id. Similarly, it has been reported that patients taking HUMIRA® (adalimumab; a recombinant human IgG1 monoclonal antibody specific for human TNFα) developed an immune response against the HUMIRA® antibodies. Id. It has also been reported that patients taking CIMZIA® (certolizumab pegol; a recombinant humanized antibody Fab' fragment with specificity for human TNFα conjugated to an approximately 40 kDa polyethylene glycol) developed an immune response against the CIMZIA® compound and reported mild to moderate adverse effects (most common being headache). Id. Alternatively, it has also been reported that the subcutaneous injection of ENBREL® (etanercept; a dimeric fusion protein consisting of the extracellular ligandbinding portion of the human p75 TNF receptor linked to the Fc portion of human IgG1) was not shown to be better than placebos in treating Crohn's patients. Id.

Systemic depletion of TNFα furthermore increases the risk of the patient for infections, as indicated by black box warnings (as required by FDA for HUMIRA®, REMICADE®, SIMPONI® (golimumab; a human IgG1κ monoclonal antibody specific for human TNFα), and CIMZIA®) for increased risk of serious infections leading to hospitalization or death, including tuberculosis (TB), bacterial sepsis, invasive fungal infections (such as histoplasmosis), and infections due to other opportunistic pathogens.

In an attempt to reduce side effects associated with systemic treatment and to eliminate the inconvenience and expense of infusions, an article proposed an oral anti-TNF therapy that could be useful in treating Crohn's disease. Worledge et al. "Oral Administration of Avian Tumor Necrosis Factor Antibodies Effectively Treats Experimental Colitis in Rats." *Digestive Diseases and Sciences* 45(12); 2298-2305 (December 2000). This article describes immunizing hens with recombinant human TNF and an adjuvant, fractionating polyclonal yolk antibody (IgY, which in chickens is the functional equivalent to IgG), and administering the unformulated polyclonal IgY (diluted in a carbonate buffer to minimize IgY acid hydrolysis in the stomach) to rats in an experimental rodent model of colitis. The rats were treated with 600 mg/kg/day of the polyclonal IgY. The uses of animal antibodies and polyclonal antibodies, however, are undesirable.

In a similar attempt to avoid adverse events associated with systemic administration, another group, Avaxia Biologics Inc., describes a topical (e.g., oral or rectal) animal-derived polyclonal anti-TNF composition that could be useful in treating inflammation of the digestive tract, such as inflammatory bowel disease. WO2011047328. The application generally states that preferably the polyclonal antibody composition is prepared by immunizing an animal with a target antigen, and the preferably the polyclonal antibody composition is derived from milk or colostrum with bovine colostrums being preferred (e.g., p. 14). The application also generally states that the animal derived polyclonal antibodies could be specific for (among other targets) other inflammatory cytokines (e.g., pp. 6-7). This application describes working examples in which cows were immunized with murine TNF and the colostrum was collected post-parturition to generate bovine polyclonal anti-TNF antibodies (designated as AVX-470). The uses of animal-derived antibodies and polyclonal antibodies, however, are undesirable.

IgA molecular forms have been proposed as treatments for various diseases, most notably as treatments for pollen allergies, as treatments against pathogens, and as treatments for cancer.

For example, two articles proposed the use of an anti-streptococcal antigen I/II secretory IgA-G hybrid antibody. Ma et al. "Generation and Assembly of Secretory Antibodies in Plants." *Science* 268(5211), 716-719 (May 1995); Ma et al. "Characterization of a Recombinant Plant Monoclonal Secretory Antibody and Preventive Immunotherapy in Humans." *Nature Medicine* 4(5); 601-606 (May 1998). The hybrid antibody contains murine monoclonal kappa light chain, hybrid Ig A-G heavy chain, murine J-Chain, and rabbit secretory component. The antibody was made by successive sexual crossing between four transgenic *N. tabacum* plants and filial recombinants to form plant cells that expressed all four protein chains simultaneously. The parent antibody (the source of the antigen binding regions, is identified as the IgG antibody Guy's 13. The group proposes that although sIgA may provide an advantage over IgG in the mucosal environment, such is not always the case (1998 Ma at p. 604, right column).

A related article identifies the anti-streptococcal antigen I/II secretory IgA-G hybrid antibody, which was derived from Guy's 13 IgA, as CaroRx. Wycoff. "Secretory IgA Antibodies from Plants." *Current Pharmaceutical Design* 10(00); 1-9 (2004). Planet Biotechnology Inc. This related article states that the CaroRx antibody was designed to block adherence to teeth of the bacteria that causes cavities. Apparently, the CaroRx antibody was difficult to purify; the affinity of Protein A for the murine Ig domain was too low and protein G was necessary for sufficient affinity chromatography. Furthermore, the article states that several other chromatographic media had shown little potential as purification steps for the hybrid sIgA-G from tobacco leaf extracts. The article also indicates that the authors were unable to control for human-like glycosylation in tobacco, but that such was not a problem because people are exposed to plant glycans every day in food without ill effect.

WO9949024, which lists Wycoff as an inventor, Planet Biotechnology Inc. as the applicant, describes the use of the variable regions of Guy's 13 to make a secretory antibody from tobacco. The application contains only two examples—the first a working example and the second a prophetic example. Working Example 1 describes the transient production of an anti-*S. mutans* SA I/III (variable region from Guy's 13) in tobacco. The tobacco plant was transformed using particle bombardment of tobacco leaf disks. Transgenic plants were then screened by Western blot "to identify individual transformants expressing assembled human sIgA" (p. 25). Prophetic Example 2 states that in a transformation system for *Lemna gibba* (a monocot), bombardment of surface-sterilized leaf tissue with DNA-coated particles "is much the same as with" tobacco (a dicot). The prophetic example also stops at screening by immunoblot analysis for antibody chains and assembled sIgA, and states that the inventors "expect to find fully assembled sIgA."

It is desirable to have alternative antibody treatments for TNFα-related inflammatory diseases that preferably avoid the disadvantages of current systemic and previously-proposed topical treatments of inflammation.

SUMMARY OF THE INVENTION

The present invention relates to monoclonal secretory IgA antibodies, which bind to and neutralize human TNFα, and their use in treating inflammatory disorders.

In embodiments, the antibody can be a chimeric antibody, a humanized antibody, or a human antibody. The antibody can contain a human secretory chain and a human J-chain. The antibody can be a human secretory IgA1 antibody. The antibody can contain CDR sequences that are identical to the CDR sequences of an antibody selected from infliximab, adalimumab, golimumab, or certolizumab pegol, or thereof variation of one of the foregoing.

In an embodiment, the antibody can contain heavy chain constant regions having the sequence of one of SEQ ID NOS:10 and 12 preferably SEQ ID NO:10, kappa light chain constant, a human secretory chain, a human J-chain, heavy chain variable regions having the sequence of SEQ ID NO:4, and light chain variable regions having the sequence of SEQ ID NO:5. In another embodiment, the antibody can contain heavy chain constant regions have the sequence of one of SEQ ID NOS:10 and 12 preferably SEQ ID NO:12, kappa light chain constant regions, a human secretory chain, a human J-chain, heavy chain variable regions having the sequence of SEQ ID NO:2, and light chain variable regions having the sequence of SEQ ID NO:3.

Another aspect of the present invention relates to a composition containing a plurality of the secretory IgA antibodies. In embodiments, substantially all N-glycans in the plurality of antibodies lack fucose and xylose residues. In embodiments, the plurality of antibodies contains at least about 30% G0 glycans (preferably G0 glycans lacking Fuc and Xyl residues) relative to the total amount of N-glycans in the population. In embodiments, the a plurality of antibodies contains at least about 25% high-mannose glycans (e.g., Man5, Man6, Man7, Man8, and/or Man9 glycans) relative to the total amount of N-glycans in the population. In embodiments, the G0 glycans (preferably G0 glycans lacking Fuc and Xyl residues) and high-mannose glycans (e.g., Man5, Man6, Man7, Man8, and/or Man9 glycans) together are the majority of glycans present in the plurality of antibodies, such as at least 70% of the total amount of N-glycans in the plurality of antibodies.

Another aspect of the present invention relates to pharmaceutical compositions containing the secretory IgA antibodies, which can be adapted for oral administration and can be used to treat an inflammatory disease in a human.

Another aspect of the present invention relates to methods for treating an inflammatory disease in a human, which includes administering an anti-inflammatory effective amount of the secretory IgA antibodies (or compositions) to a human in need thereof, preferably orally administering the antibodies (compositions). The inflammatory disease can be selected from inflammatory bowel disease (including ulcerative colitis and Crohn's disease), rheumatoid arthritis, psoriasis, psoriatic arthritis, ankylosing spondylitis, and juvenile idiopathic arthritis.

BRIEF DESCRIPTION OF THE SEQUENCES

SEQ ID NO:1 provides the amino acid sequence of the soluble TNF-α receptor of etanercept (extracellular part of tumor necrosis factor receptor 2: amino acids 23-257 of UniProtKB/Swiss-Prot database entry P20333 (TNR1B_HUMAN)).

SEQ ID NO:2 provides the amino acid sequence of the heavy chain variable region of infliximab (cA2).

SEQ ID NO:3 provides the amino acid sequence of the light chain variable region of infliximab (cA2).

SEQ ID NO:4 provides the amino acid sequence of the heavy chain variable region of adalimumab (D2E7).

SEQ ID NO:5 provides the amino acid sequence of the light chain variable region of adalimumab (D2E7).

SEQ ID NO:6 provides the amino acid sequence of the heavy chain variable region of golimumab.

SEQ ID NO:7 provides the amino acid sequence of the light chain variable region of golimumab.

SEQ ID NO:8 provides the amino acid sequence of the heavy chain variable region of certolizumab pegol.

SEQ ID NO:9 provides the amino acid sequence of the light chain variable region of certolizumab pegol.

SEQ ID NO:10 provides the amino acid sequence of a human IgA α-1 heavy chain constant region (Cα1-Cα2-Cα3) (UniProtKB/Swiss-Prot database entry P01876 (IGHA1_HUMAN)).

SEQ ID NO:11 provides the amino acid sequence of a human IgA α-2 m(1)-allotype heavy chain constant region (Cα1-Cα2-Cα3) (UniProtKB/Swiss-Prot database entry P01877 (IGHA2_HUMAN)).

SEQ ID NO:12 provides the amino acid sequence of a human IgA α-2 m(2)-allotype heavy chain constant region (Cα1-Cα2-Cα3). (UniProtKB/Swiss-Prot database entry P01877 (IGHA2_HUMAN) with indicated modifications for allotype 2 variant).

SEQ ID NO:13 provides the amino acid sequence of a human IgA α-2 (n)-allotype.

SEQ ID NO:14 provides the amino acid sequence of a human λ1 light chain constant region ($C_L$) (UniProtKB/Swiss-Prot database entry P01834 (IGKC_HUMAN)).

SEQ ID NO:15 provides the amino acid sequence of a human 21 light chain constant region ($C_L$) (UniProtKB/Swiss-Prot database entry P0CG04 (LAC1_HUMAN)).

SEQ ID NO:16 provides the amino acid sequence of a human 22 light chain constant region ($C_L$) (UniProtKB/Swiss-Prot database entry P0CG05 (LAC2_HUMAN)).

SEQ ID NO:17 provides the amino acid sequence of a human 23 light chain constant region ($C_L$) (UniProtKB/Swiss-Prot database entry P0CG06 (LAC3_HUMAN)).

SEQ ID NO:18 provides the amino acid sequence of a human λ6 light chain constant region ($C_L$) (UniProtKB/Swiss-Prot database entry P0CF74 (LAC6_HUMAN)).

SEQ ID NO:19 provides the amino acid sequence of a human λ7 light chain constant region ($C_L$) (UniProtKB/Swiss-Prot database entry A0M8Q6 (LAC7_HUMAN)).

SEQ ID NO:20 provides the amino acid sequence of a human J-chain (amino acids 23-159 UniProtKB/Swiss-Prot database entry P01591).

SEQ ID NO:21 provides the amino acid sequence of a human secretory component (amino acids 19-603 of UniProtKB/Swiss-Prot database entry P01833 (PIGR_HUMAN), RCSB Protein Data Bank structure 2OCW).

SEQ ID NO:22 provides the amino acid sequence of a natural signal peptide (secretion signal) for a human J-chain (amino acids 1-22 UniProtKB/Swiss-Prot database entry P01591).

SEQ ID NO:23 provides the amino acid sequence for a signal peptide (heavy chain secretion signal).

SEQ ID NO:24 provides the amino acid sequence for a signal peptide (light chain secretion signal).

SEQ ID NO:25 provides the amino acid sequence for a signal peptide (SC-chain secretion signal).

SEQ ID NO:26 provides the amino acid sequence for a rice α-amylase signal peptide (secretion signal).

SEQ ID NO:27 provides the DNA sequence for the infliximab heavy chain IgA2m(n) optimized for maize.

SEQ ID NO:28 provides the DNA sequence for the infliximab heavy chain IgA1 and light chain κ optimized for HEK.

SEQ ID NO:29 provides the DNA sequence for the infliximab light chain optimized for maize.

SEQ ID NO:30 provides the DNA sequence for SC- and J-chains optimized for HEK.

SEQ ID NO:31 provides the DNA sequence for the adalimumab heavy chain IgA1 optimized for *Lemna*.

SEQ ID NO:32 provides the DNA sequence for the adalimumab light chain κ optimized for *Lemna*.

SEQ ID NO:33 provides the DNA sequence for a J-chain optimized for maize.

SEQ ID NO:34 provides the DNA sequence for a J-chain optimized for *Lemna*.

SEQ ID NO:35 provides the DNA sequence for an SC-chain optimized for maize.

SEQ ID NO:36 provides the DNA sequence for an SC-chain optimized for *Lemna*.

BRIEF DESCRIPTION OF THE DRAWINGS

FIG. 1 shows the amino acid sequences of the constant regions of human IgA1 (SEQ ID NO:10), IgA2 m(1) (SEQ ID NO:11), IgA2 m(2) (SEQ ID NO:12), and IgA2(n) (SEQ ID NO:13) antibody a heavy chains;

FIGS. 2A through 2I show the amino acid sequence of various TNF-α binding regions. FIG. 2A shows the amino acid sequence of the soluble TNF-α receptor of etanercept (SEQ ID NO:1); FIG. 2B shows the amino acid sequence of the heavy chain variable region of infliximab (cA2) (SEQ ID NO:2); FIG. 2C shows the amino acid sequence of the light chain variable region of infliximab (cA2) (SEQ ID NO:3); FIG. 2D shows the amino acid sequence of the heavy chain variable region of adalimumab (D2E7) (SEQ ID NO:4); FIG. 2E shows the amino acid sequence of the light chain variable region of adalimumab (D2E7) (SEQ ID NO:5); FIG. 2F shows the amino acid sequence of the heavy chain variable region of golimumab (SEQ ID NO:6); FIG. 2G shows the amino acid sequence of the light chain variable region of golimumab (SEQ ID NO:7); FIG. 2H shows the amino acid sequence of the heavy chain variable region of certolizumab pegol (SEQ ID NO:8); FIG. 2I shows the amino acid sequence of the light chain variable region of certolizumab pegol (SEQ ID NO:9).

FIGS. 3A and 3B show the amino acid sequences of various human antibody light chain subtypes and allotypes. FIG. 3A shows the amino acid sequence of a human κ light chain constant region ($C_L$) (UniProtKB/Swiss-Prot P01834) (SEQ ID NO:14); FIG. 3B shows the amino acid sequences of a human λ light chain constant region ($C_L$) allotypes (UniProtKB/Swiss-Prot P0CG04, P0CG05, P0CG06, P0CG74, and A0M8Q6; SEQ ID NOS:15 to 19).

FIG. 4 shows the amino acid sequence of a human J-chain (a.a. 23-159 of UniProtKB/Swiss-Prot entry P01591, SEQ ID NO:20).

FIG. 5 shows the amino acid sequence of a human secretory component (a.a. 19-603 of UniProtKB/Swiss-Prot database entry P01833 [PIGR_HUMAN], SEQ ID NO:21).

FIG. 14 is a representative depiction of mini-endoscopic pictures of the colitis score at day t=15 for a mouse from each test group.

DETAILED DESCRIPTION OF THE INVENTION

Figure 6:
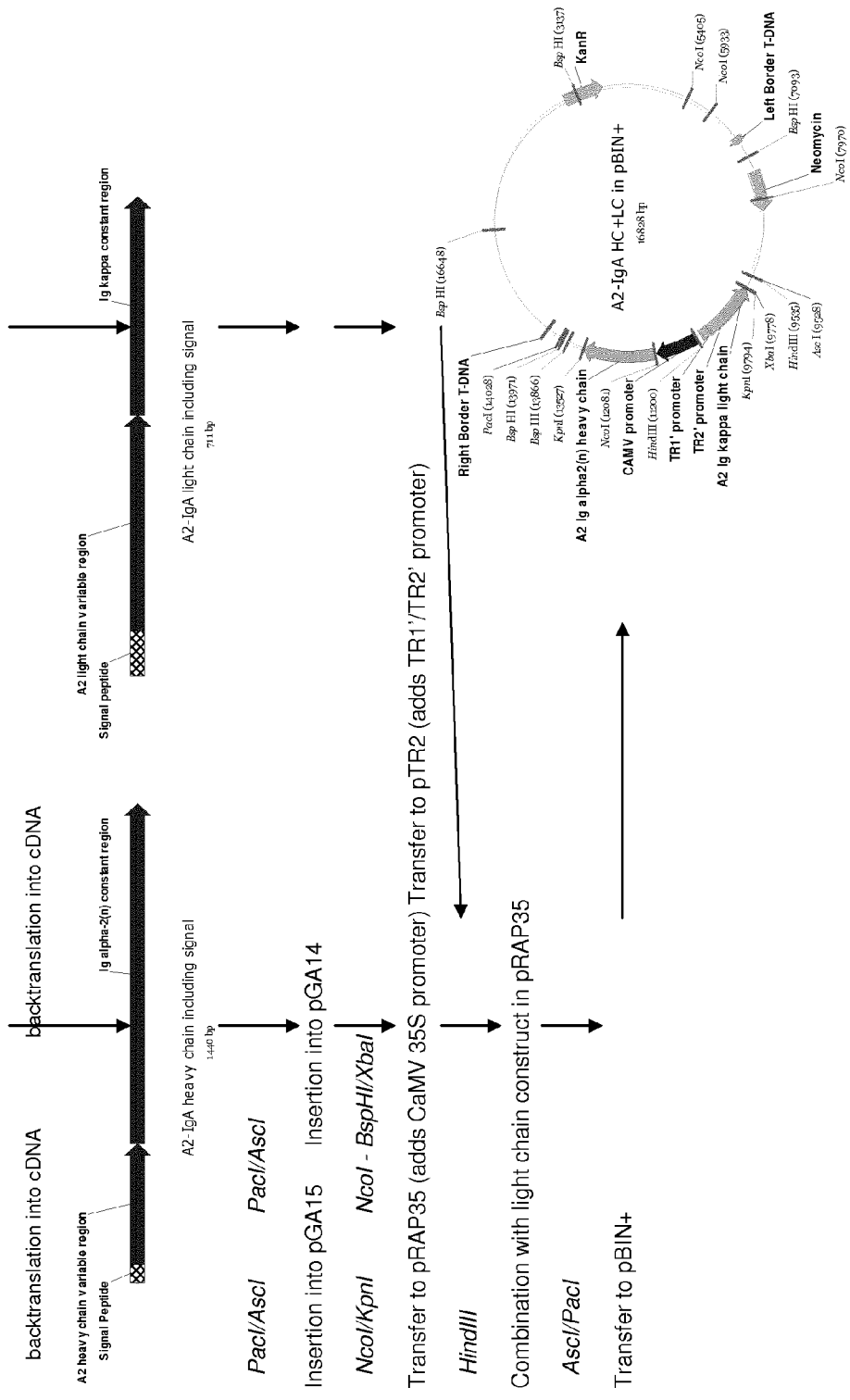
FIG. 6 shows the structure of the SIgA vector constructs of Example 1.

The present invention relates to monoclonal secretory IgA antibodies that bind to and neutralize human TNFα.

As is well known, the basic structural unit of an antibody consists of two heavy chain proteins (heavy chains) and two light chain proteins (light chains), which are bound together by non-covalent and covalent (e.g., disulfide bonds) interactions into a single unit. The heavy and light chains have N-terminal variable regions and C-terminal constant regions. The variable regions of the light and heavy chains together form an "antigen binding region." Because the antibody has two heavy and light chains, the antibody has two antigen binding regions.

Antibodies are classified based on the heavy chain constant region, e.g., classified as IgG, IgA, IgM, IgE, IgD, etc. The light chain constant region is not used for classification. In humans, for example, all classes use one of two types of light chain constant regions, namely the Cκ (kappa) or Cλ (lambda) type. The amino acid sequences of human kappa (SEQ ID NO:14) and several lambda light chain constant regions (SEQ ID NOS:15-19) are provided in FIGS. 3A and 3B, respectively. In nature, the heavy chain constant regions of the various classes are produced by different genes: the IgA class heavy chains are uniquely encoded-for by α genes, the IgG class heavy chains by γ genes, and so forth. The heavy chain constant regions also impart the various classes with differences in their physio-chemical properties, their isotypic antigenic determinants, and/or in their biological function. Lefranc et al., *The Immunoglobulin FactsBook*, Academic Press 2001, Chapter 2, (ISBN 0-12-441351-X). The constant region of an IgA heavy chain (Cα) typically has three domains that are referred to as Cα1, Cα2, and Cα3, a short hinge section between Cα1 and Cα2, and a short tail piece at the C-terminal end of Cα3. The definition and structure of antibodies are well known to workers skilled in this art, such as described in, e.g., Alberts, B. et al., *Molecular Biology of the Cell 3$^{rd}$ Edition*, Chapter 23, Garland Publishing Inc., New York, N.Y., 1994, and Nezlin, R., *The Immunoglobulins. Structure and Function* (1998) Academic Press (ISBN 0-12-517970-7).

The C-terminal section of two IgA antibodies, i.e., the tail pieces at the C-terminal ends of the Cα3 region, can be joined together via a J-chain to form a dimer. Dimeric IgA has four antigen binding regions; two from each IgA monomer. Typically the four antigen binding regions (and their complementarity determining regions or "CDRs") are identical for reasons such as ease of manufacture. But the antigen binding regions can, in certain circumstances, be different, e.g., different CDRs binding different epitopes on the same antigen or event different antigens (such as in the case of bispecific antibodies). Typically the CDRs of the four antigen binding regions are identical. A secretory chain, some-times called a secretory component or SC-chain, can be attached to the dimeric IgA antibody. The SC-chain provides increased resistance to proteolysis especially in the intestinal tract. The SC-bound dimeric IgA is referred to herein as "secretory IgA" or "SIgA."

Heavy chain constant regions that qualify as an IgA-class antibody are well known in the art. Generally the amino acid sequence of the heavy chain constant regions of an IgA, regardless of how it is produced (e.g., naturally or recombinantly), corresponds to an amino acid sequence encoded for by an α-gene. In addition, IgA antibodies have characteristic antigenic determinants unique to IgA-class antibodies and different from the antigenic determinants of other classes of antibodies, such as IgG-class antibodies (see, e.g., Nezlin, R., *The Immunoglobulins. Structure and Function* (1998) Academic Press (ISBN 0-12-517970-7); Lefranc et al., *The Immunoglobulin FactsBook*, Academic Press 2001, Chapter 2, (ISBN 0-12-441351-X)). Furthermore, IgA antibodies are the only isotype that is known to specifically bind to the FcαR (see, e.g., Alberts, B. et al., *Molecular Biology of the Cell* 3$^{rd}$ *Edition,* Chapter 23, Garland Publishing Inc., New York, N.Y., 1994; Lefranc et al., *The Immunoglobulin FactsBook*, Academic Press 2001, Chapter 2, (ISBN 0-12-441351-X)).

Accordingly, for purposes of the present invention, the terms "IgA antibody," "monomeric IgA," "dimeric IgA" and "SIgA" each refers to antibodies that contain the heavy chain constant regions of an IgA class of immunoglobulin, e.g., which corresponds to an amino acid sequence that can be encoded for by α genes and which react with an antibody specific for the IgA-class heavy chain. The amino acid sequence "corresponds" in that it is identical to, or contains only minor variations (insertions/deletions/substitutions) from, an amino acid sequence produced by any α gene, an individual human's IgA heavy chain sequence, or a human IgA heavy chain consensus sequence. Indeed, variations can and do exist in the amino acid sequence of the IgA heavy chain constant region without moving such antibodies outside of the IgA class. Examples of such variations can be found in various genomic databases such as browser.1000genomes.org/index.html and ensembl.org/index.html. For clarity, because the heavy chain sequence is determinative of the Ig class, a recombinant antibody containing the IgA heavy chain constant regions and further containing the antigen binding regions encoded for by DNA sequences obtained from a known IgG antibody is still an "IgA antibody." On the other hand, a secretory IgA antibody modified to replace the Cα2 heavy chain constant domain (encoded for by the IgA-specific α-gene) with a Cγ2 heavy chain constant domain (encoded for by the IgG-specific γ-gene) is not an IgA antibody, and is instead a hybrid IgA/IgG antibody. Such a hybrid is not within the scope of the terms "monomeric IgA," "dimeric IgA" and "SIgA" antibodies, and thus is not a secretory IgA antibody according to the invention.

Minor variations of the heavy chain constant regions are permitted only to the extent that the overall antibody class, framework, and functionality of SIgA is maintained; e.g., J-chain binds to monomers and SC-chain binds to the dimeric structure and provides proteolysis resistance. Such variations include conservative substitutions. Exemplary conservative substitutions are shown in Table 1. The amino acids in the same block in the second column and preferably in the same line in the third column may, for example, be substituted for each other.

TABLE 1

| ALIPHATIC | Non-polar | G A P |
| --- | --- | --- |
|  |  | I L V |
|  | Polar-uncharged | C S T M |
|  |  | N Q |
|  | Polar-charged | D E |
|  |  | K R |
| AROMATIC |  | H F W Y |

Typical minor variations of the constant regions from the normal or naturally-occurring sequence involve only conservative changes to the amino acid sequence using the recognized substitutions, insertions and/or deletions. Generally, the variations (substitutions, insertions, and/or deletions) of a constant domain of the heavy or light chain involve no more than 10 and usually no more than 5 amino acid additions, deletions, and/or substitutions (either naturally-occurring or genetically-engineered), in any Cα1, Cα2, or Cα3 domain or hinge or tail sections in comparison to a normal IgA constant domain. The sum of these minor variations in the constant domains of the SIgA antibody of the invention is usually less than 20 amino acids (acid/deletions/substitutions) and often less than 10 or less than 5.

Accordingly, at a minimum, SIgA includes any recognized amino acid sequence that is generally accepted as being within the IgA class. For example, information on the structure and function of IgA can be found in Snoeck et al., *Vet. Res.* 37; 455-467 (2006) and "Mucosal immune defense: Immunoglobulin A", C. S. Kaetzel ed., Springer, New York (2007) ISBN 978-0-387-72231-3. Electronic databases, such as RCSB Protein Data Bank, can also establish a known IgA sequence or portion/domain thereof. The constant domains contained in the SIgA antibodies of the invention can be human, non-human, or a combination of these. Preferred are mammalian constant regions. Most preferred are human constant regions.

In humans there are two recognized IgA subclasses: IgA1 and IgA2 which differ in the hinge section between the Cα1 and Cα2 domains of the heavy chain. In IgA1 this hinge section is relatively long and in nature typically O-glycosylated. In IgA2 the hinge section is relatively short and in nature lacks glycosylation. Both IgA1 and IgA2 SIgA antibodies are usually present in mucosal secretions. In humans, the IgA2 subclass has three known allotypes: IgA2m(1), IgA2m(2) and IgA2m(n). Unlike the subclasses, only one specific allotype will be found in a normal healthy individual. The m(1) allotype is strongly prevalent in the Caucasian population (98%) and varies between 23% and 96% for other populations. The m(2) allotype has a high prevalence in populations of African and Asian descent (50-70%). The m(n) allotype—which is considered to be a hybrid of the m(1) and m(2) allotypes—has been reported to be genetically possible, but has not been actually observed in any population. See Chintalacharuvu et al., *Journal of Immunology* 152, 5299-5304 (1994). Accordingly, SIgA antibodies of the present invention preferably contain human IgA heavy chain constant regions of the IgA1 or IgA2 sub-types, including IgA2m(1), IgA2m(2) and IgA2m(n) allotypes, and combinations thereof (e.g., one constant domain or hinge section from an IgA1 and another constant domain or hinge section from an IgA2).

Typically, the SIgA antibodies of the invention comprise the Cα1 domain, the hinge section, and the -Cα2-Cα3 domains and tail section of an IgA antibody (with or without minor variations), including a human IgA1 and/or IgA2 antibody. In this embodiment, the Cα1 domain, the hinge section, and the -Cα2-Cα3 domains can be of an IgA1, an IgA2m(1) allotype, an IgA2m(2) allotype, or a combination thereof. Amino acid sequences of a human IgA1 heavy chain constant region (SEQ ID NO:10), a human IgA2m(1) heavy chain constant region (SEQ ID NO:11), a human IgA2m(2) heavy chain constant region (SEQ ID NO:12), and a human IgA2(n) heavy chain constant region (corresponding to the Cα1 and Cα2 regions of an IgA2m(2) and the Cα3 region of an IgA2m(1)) (SEQ ID NO:13) are respectively shown in FIG. 1.

A modified, shortened, or removed linker/hinge section between Cα1 and Cα2 in IgA1 has been reported to increase resistance against proteases (for example see B. W. Senior et al., *J. Immunol.* 2005; 174: 7792-7799). Such can be incorporated into the SIgA antibodies of the present invention.

The J-chain is a protein that attaches to the tail piece of a monomeric IgA to join two monomeric IgAs to form a dimer. The J-chain is normally of mammalian origin, such as human, murine, rat, rabbit, sheep, cow, or goat origin, but is preferably of human origin. An example of the amino acid sequence of a human J-chain is set forth in FIG. 4 (SEQ ID NO:20). Usually, the sequence of the mammalian-derived J-chain is the same as the naturally-occurring sequence, but it can be subject to minor variations as described above for constant regions generally, e.g., up to 10 amino acid insertions, substitutions, or deletions. The minor variations do not significantly alter the function of the J-chain, and in particular the ability to join two monomeric IgA antibodies to form a dimer and to enable attachment of the SC-chain.

The secretory component, also referred to as "SC" or "SC-chain," is a protein that binds to the dimeric IgA framework and imparts increased resistance against proteolysis upon the antibody to which it is bound. Generally, the secretory component is of mammalian origin, such as human, murine, rat, rabbit, sheep, cow, or goat origin, but is preferably of human origin. The SC is the result of cleavage of the Polymeric IgA-receptor (PIGR) which usually occurs at a specific position. Some variation can occur in the position of the cleavage resulting in variant forms of SC. Usually, the sequence of the mammalian-derived SC-chain is the same as the naturally-occurring sequence, but it can be subject to minor variations as described above for constant regions generally, e.g., up to 10 amino acid insertions, substitutions, or deletions. The minor variations do not significantly alter the function of the secretory component, e.g., the ability to stabilize the SIgA against proteolysis. An example of the amino acid sequence of a human secretory component is set forth in FIG. 5 (SEQ ID NO:21).

The antigen binding region comprises a heavy and light chain variable region pair, each containing hypervariable regions (CDRs, which directly interact with the TNFα) and the supporting framework regions. The CDRs in each heavy and light chain variable region are separated from each other and from the constant domain by the framework regions, which serve to maintain the CDRs in the correct binding conformation. In general each variable part of an immunoglobulin heavy or light chain contains 3 different CDRs and four framework regions. For a more detailed description of antibody antigen binding regions, see for example C. A. Janeway et al., "*Immunobiology*" 6th Edition, Chapter 3, pp 110-115; Garland Science Publishing, New York, 2005 (ISBN 0815341016). Regarding framework regions in particular, see for example WO92/22653 (discussing that although framework regions do not directly interact with antigen, framework regions can influence binding of the CDRs with antigen, such as binding strength and/or downstream events).

The antigen binding regions of the secretory IgA antibodies of the present invention bind to human TNFα, although the antigen binding regions can also bind other mammalian TNFα. Thus the antigen binding regions of the secretory IgA antibodies must bind at least human TNFα, but may also bind other mammalian TNF-α. For example, the antigen binding regions of adalimumab bind human TNFα and also bind murine TNFα. Usually, though not necessarily, the antigen binding is specific to TNFα; meaning that it binds preferentially and with high affinity. A variety of protocols for binding, competitive binding or immuno-radiometric assays to determine the specific binding capability of an antibody are well known in the art (see for example Maddox et al, *J. Exp. Med.* 158, 1211-1226, 1993). Such immunoassays typically involve the formation of complexes between the specific protein and its antibody and the measurement of complex formation. Generally the secretory IgA antibodies of the present invention exhibit a preference or specificity for TNFα such that the affinity is at least two-fold, at least 10-fold, at least 50-fold, at least 100-fold, or at least 1000-fold or greater than its affinity for binding to a non-specific polypeptide such as, for instance, BSA or casein. Typically the secretory antibody of the present invention exhibits a binding affinity constant ($K_D$) with respect to TNF-α of $10^{-7}$ M or lower, preferably $10^{-8}$ M, $10^{-9}$ M, $10^{-10}$ M, $10^{-11}$ M, or $10^{-12}$ M or lower.

In embodiments, secretory IgA antibodies of the present invention neutralize a human TNFα to which it is bound. For the present invention, the term "neutralizes" means inhibits/reduces the effect of the cytokine to some degree, such as by at least 30%, at least 35%, at least 40%, and at least 45%. Typically the inhibition/reduction in the effect of the cytokine at least 50%. In these embodiments, the secretory IgA antibodies of the present invention preferably inhibit/reduce the proinflammatory effect of a human TNFα to which it is bound by at least 50%, such as by at least 55%, at least 60%, at least 65%, and at least 70%, and more preferably by at least 75%, at least 80%, at least 85%, at least 90%, at least 95%, and at least 98%.

The amino acid sequence of the antigen binding region, and in particular the CDRs thereof, is determined by the epitope to which it binds. The amino acid sequence of the antigen binding region can be novel or can be obtained from existing anti-TNFα antibodies. Methods for obtaining novel antigen binding sequences are well known in the art. See for example Mary A. Ritter and Heather M. Ladyman (Eds.) "*Monoclonal antibodies: production, engineering, and clinical application*", Cambridge University Press (1995), ISBN 0521425034, Zhiqiang An "*Therapeutic Monoclonal Antibodies: From Bench to Clinic*" Wiley, New York (2009), ISBN: 0470117915, and Christopher Dean and Philip Shepherd (Ed.) "*Monoclonal Antibodies: A Practical Approach*" Oxford University Press, USA (2000), ISBN 0199637229.

In embodiments, secretory IgA antibodies of the invention comprise CDR sequences that are identical to the CDR sequences of an antibody selected from infliximab, adalimumab, golimumab, and certolizumab. The CDR sequences for these antibodies are identified below in Table 2. Of course, the CDR sequences for these and other known antibodies can be obtained from other patent and non-patent literature, and commercially-available antibodies can be purchased and sequenced.

TABLE 2

| Pair No | Parental antibody | CDR1 | CDR2 | CDR3 |
|---|---|---|---|---|
| 1 | Infliximab-heavy chain variable region (FIG. 2B) (SEQ ID NO: 2) | 26-35 | 50-68 | 101-109 |
|  | Infliximab-light chain variable region (FIG. 2C) (SEQ ID NO: 3) | 24-34 | 50-56 | 89-97 |
| 2 | Adalimumab-heavy chain variable region (FIG. 2D) (SEQ ID NO: 4) | 26-35 | 50-66 | 99-107 |
|  | Adalimumab-light chain variable region (FIG. 2E) (SEQ ID NO: 5) | 24-34 | 50-56 | 89-97 |
| 3 | Golimumab-heavy chain variable region (FIG. 2F) (SEQ ID NO: 6) | 26-35 | 50-66 | 99-115 |
|  | Golimumab-light chain variable region (FIG. 2G) (SEQ ID NO: 7) | 24-34 | 50-56 | 89-108 |
| 4 | Certolizumab-heavy chain variable region (FIG. 2H) (SEQ ID NO: 8) | 26-35 | 50-66 | 99-107 |
|  | Certolizumab-light chain variable region (FIG. 2I) (SEQ ID NO: 9) | 24-34 | 50-56 | 89-97 |

In still other embodiments, antigen binding regions (or CDRs) of secretory IgA antibodies of the invention are obtained from other and/or novel anti-TNFα antibodies. Methods for obtaining antibodies against specific antigens are well known in the art and can be used to obtain suitable TNFα-binding variable regions. See, for example, Mary A. Ritter and Heather M. Ladyman (Eds.) "Monoclonal antibodies: production, engineering, and clinical application", Cambridge University Press (1995), ISBN 0521425034, Zhigiang An "Therapeutic Monoclonal Antibodies: From Bench to Clinic" Wiley, New York (2009), ISBN: 0470117915, and Christopher Dean and Philip Shepherd (Ed.) "Monoclonal Antibodies: A Practical Approach" Oxford University Press, USA (2000), ISBN 0199637229.

Secretory IgA antibodies of the invention can be non-human antibodies, chimeric antibodies, humanized antibodies, human antibodies, or other mixes of human and non-human sequences/regions. See, e.g., Yamashita et al. Cytotechnology 55: 55-60 (2007). A chimeric antibody is an antibody having an antigen binding region (CDRs and framework) originating from a first species (typically a mouse) and heavy chain constant regions originating from a second species (typically a human). A humanized antibody is a human antibody onto which non-human (typically murine) CDRs have been grafted. In the humanized antibody, certain human supporting framework amino acid residues can be replaced with their counterparts from the non-human parent antibody. Such an antibody containing certain non-human framework residues is still a humanized antibody. See, e.g., WO92/22653. In the humanized antibodies, the sequence of the supporting framework into which the non-human CDRs are grafted can be obtained from any human isotype/class, preferentially from IgG or IgA, and may be modified to improve the properties thereof (e.g., antigen binding and/or downstream effects). A human antibody is fully-human, containing only human constant and variable regions, i.e., having only human heavy and light chains (derivable from human genomic sequences by naturally-occurring recombination and mutation processes, consensus sequences, etc.). Likewise, a non-human antibody contains only non-human constant and variable regions, i.e., having only non-human heavy and light chains.

The secretory IgA antibodies of the invention may contain additional atoms, moieties, molecules, and/or modifications beyond the dimeric IgA, J-chain, and SC-chain. For example, the secretory IgA antibodies of the invention may be PEGylated or glycosylated (or aglycosylated) in various orientations and/or amounts. The location, attachment, amount, and structure of attached glycans found in naturally occurring antibodies shows substantial variability and mainly depends on the source of the glycoprotein (i.e., the type of cell producing the glycoprotein), but is also influenced by growing conditions (i.e., feed and environmental conditions). The secretory IgA antibodies of the present invention are not limited to any specific form of glycosylation and specifically include non-glycosylated proteins, partially or fully deglycosylated proteins, variants obtained by genetic or other manipulation of the glycosylation system of the producing cell, and variants with chemically or enzymatically modified glycans. The secretory IgA antibodies of the invention can be glycoproteins with glycosylation patterns native to plant, mammalian (human), or insect cells. Additionally the antibodies of the invention may be conjugated with (fluorescent) markers or therapeutic agents, etc. (see, e.g., Lash, A. "Making the case for antibody-drug conjugates;" In Vivo: The Business & Medicine Report; vol. 28, No. 11, pp. 32-39 (December 2010) (www.ElsevierBI.com).

It is recognized that antibodies having more than one glycosylation site can have the same glycan species attached to each glycosylation site, or can have different glycan species attached to different glycosylation sites. In this manner, different patterns of glycan attachment yield different glycoforms of a glycoprotein. Monomeric IgA1 antibodies have two conserved N-glycosylation sites (per chain): one on the CH2 region and one on the tailpiece. Monomeric IgA2 antibodies have an additional two or three N-glycosylation sites (per chain). Furthermore, the J-chain of dimeric IgA has one conserved N-glycosylation site, and the secretory component of secretory IgA has 7 conserved N-glycosylation sites.

The terms "N-glycan(s)" and "N-linked glycan(s)" are used interchangeably and refer to an N-linked oligosaccharide, e.g., one that is or was attached by an N-acetylglucos amine (GlcNAc) residue linked to the amide nitrogen of an asparagine residue in a protein. The predominant sugars found on glycoproteins are glucose (Glu), galactose (Gal), mannose (Man), fucose (Fuc), N-acetylgalactosamine (GalNAc), N-acetylglucosamine (GlcNAc), and sialic acid (e.g., N-acetyl-neuraminic acid (NeuAc)). The processing of the sugar groups occurs co-translationally in the lumen of the ER and continues in the Golgi apparatus for N-linked glycoproteins.

For the purposes of the present invention, the term "G2 glycan," "G2 glycan species," and "G2 glycan structure" are used interchangeably and refer to an N-linked glycan having the GlcNAc2Man3GlcNAc2Gal2 structure, in which two terminal galactose (Gal) sugar residues are present. For the purposes of the present invention, the term "G1 glycan," "G1 glycan species," and "G1 glycan structure" are used interchangeably and refer to an N-linked glycan having the GlcNAc2Man3GlcNAc2Gal structure, in which only one terminal galactose (Gal) sugar residue is present. For the purposes of the present invention, the term "G0 glycan," "G0 glycan species," and "G0 glycan structure" are used interchangeably and refer to an N-linked glycan having the GlcNAc2Man3GlcNAc2 structure, in which no terminal galactose (Gal) sugar residues are present.

For the purposes of the present invention, the term "high-mannose glycan," high-mannose glycan species," and "high-mannose glycan structure" are used interchangeably and refer to an N-linked glycan having the GlcNAc2ManX structure, wherein X is a whole number greater than three, such as 5, 6, 7, 8, or 9. For the purposes of the present invention, the term "Man5 glycan," Man5 glycan species,"

and "Man5 glycan structure" are used interchangeably and refer to an N-linked glycan having the GlcNAc2Man5 structure. The same is applicable for the terms Man6 glycan (species; glycan structure), Man7 glycan (species; glycan structure), Man8 glycan (species; glycan structure), Man 9 glycan (species; glycan structure), etc.

In mammals, naturally-occurring N-glycans contain a fucose (Fuc) residue attached to the GlcNAc2Man3 core structure by an α1,6 linkage. In plants, naturally-occurring N-glycans contain a fucose (Fuc) residue attached to the GlcNAc2Man3 core structure by an α1,3 linkage and further contain a xylose (Xyl) residue attached to the GlcNAc2Man3 core structure by a β1,2 linkage. For the purposes of the present invention, a G0 glycan containing the mammalian α1,6-linked Fuc residue attached to the GlcNAc2Man3 core structure is referred to as a "G0F<6> glycan." For the purposes of the present invention, a G0 glycan containing the plant α1,3-linked Fuc residue attached to the GlcNAc2Man3 core structure is referred to as a "G0F<3> glycan," a G0 glycan containing the plant β1,2-linked Xyl residue attached to the GlcNAc2Man3 core structure is referred to herein as a "G0X glycan," and a G0 glycan containing each of the plant α1,3-linked Fuc residue and the plant β1,2-linked Xyl residue attached to the GlcNAc2Man3 core structure is referred to herein as a "G0XF<3> glycan." In an embodiment, the invention relates to a secretory IgA antibody, or a population of secretory IgA antibodies, in which substantially all N-glycans lack Fuc and Xyl residues.

The present invention also relates to a composition comprising a plurality of secretory IgA antibodies containing multiple N-glycans, such as two or more different N-glycans. In embodiments, the plurality of secretory IgA antibodies contains at least about 30% G0 glycans (preferably G0 glycans lacking Fuc and Xyl residues) relative to the total amount of N-glycans in the population. In embodiments, the plurality of secretory IgA antibodies contains at least about 25% high-mannose glycans (e.g., Man5, Man6, Man7, Man8, and/or Man9 glycans) relative to the total amount of N-glycans in the population. In embodiments, G0 glycans (preferably G0 glycans lacking Fuc and Xyl residues) and high-mannose glycans (e.g., Man5, Man6, Man7, Man8, and/or Man9 glycans) together are the majority of glycans present in the plurality of secretory IgA antibodies, such as at least 70% relative to the total amount of N-glycans in the plurality of secretory IgA antibodies.

The nature of glycan species can be determined by measuring the glycosylation profile thereof. The term "glycosylation profile" means the characteristic fingerprint of the representative N-glycan species that have been released from an antibody, either enzymatically or chemically, and then analyzed for their carbohydrate structure, for example, using LC-HPLC, or MALDI-TOF MS, and the like. See, for example, the review in *Current Analytical Chemistry*, Vol. 1, No. 1 (2005), pp. 28-57." For more information on glycosylation of therapeutic antibodies, see, e.g., Fernandes et al., *Eur. Biopharm. Rev.*, Summer 2005, pp. 106-110; Jefferis, *Nature Reviews/Drug Discovery*, vol. 8, March 2009, pp. 226-234.

The SIgA antibodies of the present invention are preferably monoclonal antibodies. A "monoclonal antibody" refers to a population or collection of antibodies that are substantially identical because they were all produced by clones of a single cell. For the present invention, a monoclonal SIgA is a SIgA containing monoclonal monomeric IgA antibodies. Preferably, a monoclonal SIgA contains monomeric IgA antibodies, a J-Chain, and an SC-chain that were all produced by a clone of a single cell.

The antibodies of the present invention are often isolated or in an isolated form. As used herein, the terms "isolate," "isolating" and "isolation" refer to separating the antibody from its production environment. The extent of separation is generally at least 50%, but is frequently at least 70%, 80%, 90%, 95%, 98%, 99%, 99.5%, or 99.9% (w/w). When the SIgA antibody of the present invention is produced in a cell, which is the typical process, the separation refers to separating the antibody from the host cells and native host cell proteins. Isolation is thus related to purification. Preferably the antibody of the present invention in isolated form has removed, or been separated from, at least 90%, more typically at least 99% (w/w) of the host cell proteins of the original composition.

Various compositions that contain the secretory IgA antibodies of the present invention, whether in an isolated form or not, are also contemplated as being part of the present invention. For instance, compositions that contain low amounts of incomplete secretory IgA antibodies are often desirable. With respect to the amount of secretory IgA antibodies in the composition, the amount of dimer IgA (no SC-chain) is desirably less than 50%, more desirably less than 25% and often less than 10%. Thus in a composition that contained 10 mg of secretory IgA, the amount of non-SC-chain dimeric IgA would preferably be less than 1 mg, i.e., less than 10%. The same is true for monomeric IgA: the content of IgA monomers is desirably less than 50% the amount of secretory IgA, more desirably less than 25% and often less than 10%. In some embodiments, the combined amount of dimer IgA (i.e., no SC-chain) and monomer IgA is less than 25% of the amount of secretory IgA in the composition, often less than 10%, and even less than 5%. The above amounts apply to both isolated and non-isolated forms of secretory IgA compositions. Accordingly, the low relative amounts of incomplete secretory IgA can be a result of the expression system (native low-production of incomplete secretory IgA), the result of some separation or purification that removes incomplete secretory IgA antibodies, or both.

Purified secretory IgA compositions are also useful. A purified secretory IgA (composition) contains a secretory IgA antibody of the present invention in an amount of at least 85%, often at least 90%, more often at least 95%, and preferably at least 97%, 98%, or 99%, based on the total soluble protein content. The purified composition can be a solid, such as a lyophilized product, or a liquid. A typical liquid form contains no solids, e.g., no insoluble cell wall materials, and is often based on water as the main or sole solvent and optionally containing salts, pH adjusting agents, or buffers. A purified liquid composition generally contains the secretory IgA antibody of the invention in a concentration of 50 µg/ml or more, often at least 100 µg/ml, preferably at least 1 mg/ml.

Production of Proteins of the Present Invention

The SIgA antibodies of the invention can be produced using recombinant techniques. Although several expression systems are known, including CHO, HEK, yeast, tobacco, etc., the use of duckweed as the host cell has been found to be advantageous for the production of SIgAs. Other plant host cells, namely tobacco and lettuce, tend to give very low expression rates of the desired SIgA and typically render impractical a measurable recovery of the antibody. Similarly, CHO cells also tend to give low results. HEK generally have higher titers than CHO cells, but have certain production and regulatory disadvantages. Accordingly, duckweed is, surprisingly, a convenient host cell for expressing secretory IgAs of the present invention.

Generally, a genetically modified duckweed is a known expression system for producing various proteins (see U.S. Pat. No. 6,040,498), including for the production of monoclonal antibodies (see U.S. Pat. No. 7,632,983). Duckweed is the common name for the members of the monocotyledonous family Lemnaceae. The five known genera and 38 species of Lemnaceae are all small, free-floating, freshwater plants whose geographical range spans the entire globe: genus *Lemna* (*L. aequinoctialis, L. disperma, L. ecuadoriensis, L. gibba, L. japonica, L. minor, L. minuscula, L. obscura, L. perpusilla, L. tenera, L. trisulca, L. turionifera, L. valdiviana*); genus *Spirodela* (*S. intermedia, S. polyrrhiza*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) genus *Wolfiella* (*Wl. caudata, Wl. denticulata, Wl. gladiata, Wl. hyalina, Wl. lingulata, Wl. repunda, Wl. rotunda*, and *Wl. neotropica*), and genus *Landoltia* (*L. punctata*). For clarity, the term "duckweed' as used in the present invention includes the foregoing species, genetically modified variants thereof (e.g., modified to control glycosylation, secretion, etc.), and any other genera or species of Lemnaceae, if they exist, optionally in a genetically modified form. Typically the genus *Lemna* is preferred, especially the species *L. minor* and *L. gibba* in natural or genetically modified forms. Also, the use of the term "duckweed," or any genus or species thereof, is meant to include individual plant cell(s), nodules, as well as whole plants including mature plants having root and fronds, unless otherwise indicated by context or express statement.

Recombinant production of sIgAs in duckweed requires transformation of duckweed, either transiently or stably. For production purposes, a stable transformation, wherein the nucleic acid sequences and/or genes needed to produce the desired SIgA have been operably introduced into the genome of a duckweed, is typically preferred. Stable transgenesis in duckweed can be obtained by different techniques as described in U.S. Pat. Nos. 6,040,498 and 7,161,064 to Stomp et al. Briefly stable duckweed transgenesis can be achieved by DNA-coated particle bombardment, electroporation, and *Agrobacterium* spp.-mediated transformation. Preferably, transgenesis of duckweed is performed by using *A. tumefaciens*-mediated transformation. Briefly, *Agrobacterium*-mediated transformation is carried out by dedifferentiating fully grown duckweed plants or tissues, preferably tissues of meristematic origin, into calli. Callus induction is carried out by growing duckweed in medium containing plant growth regulators and supplements. Calli can/will re-differentiate into organized nodules. Both nodules or calli can be infected with *Agrobacterium*, according to the procedure described in U.S. Pat. Nos. 6,040,498 and 7,161,064 to Stomp et al. Regeneration of plants from infected calli/nodules and concomitant selection for transformants by applying the desired selective pressure results in the isolation of transgenic duckweed lines carrying the exogenous DNA of interest.

Construct for expression of SIgAs, to be used for transformation of duckweed, can be produced by using standard techniques for example, the techniques described in Sambrook & Russell, Molecular Cloning: A Laboratory Manual, 3rd Edition, Cold Spring Harbor Laboratory, NY (2001) and Ausubel et al, Current Protocols in Molecular Biology (Greene Publishing Associates and Wiley Interscience, NY (1989)). Vectors for transformation of duckweed have been described elsewhere, such as in U.S. Pat. Nos. 6,040,498 and 7,161,064 to Stomp et al. Preferably, an *A. tumefaciens* binary vector (generated, for example, by standard cloning in *E. coli*) is used to first transform *A. tumefaciens*; the transgenic line obtained can then be employed to transform duckweed. Preferably, such vectors contain multiple resistance genes, to allow for selection in bacteria and in duckweed. Genes for bacterial selection are known in the art. Suitable resistance genes for selection in plants have been described in U.S. Pat. Nos. 6,040,498 and 7,161,064 to Stomp et al., and include gentamycin and kanamycin.

For expression of SIgAs, multiple transformations can be performed with separate vectors including different cassette coding for the J-chain, the SC-chain, the antibody H chain and L chain. In a preferred embodiment, a single vector is used for transformation that contains 4 cassettes each encoding for one of the structural subunit of the SiGA (namely, H chain, L chain, SC-chain and J-chain). Construction of vectors containing multiple expression cassette for antibody expression have been described in U.S. Pat. No. 7,632,983 to Dickey et al.

In one embodiment, expression of the cassettes is driven by individual promoters. Examples of suitable promoter can be found in U.S. Pat. No. 4,771,002 to Stanton, U.S. Pat. No. 5,428,147 to Barker et al., U.S. Pat. No. 7,622,573 & U.S. Pat. No. 8,034,916 to Dickey et al., disclosures of which are incorporated herein by references. Most preferably, four different promoters are used for each expression cassette (such as the chimeric *A. tumefaciens* octopine and mannopine synthase promoter, the *L. minor* polyubiquitin promoter (LmUbq), *Lemna aequinoctialis* polyubiquitin promoter (LaUbq) and *Spirodela polyrrhiza* polyubiquitin promoter (SpUbq). In a preferred embodiment, the expression vector includes cassettes coding for all 4 of the SIgA components, i.e. J-chain, SC-chain, H-chain and L-chain. In even more preferred embodiment, each of the 4 cassettes is driven by a different promoter. In a different embodiment, the constructs are driven by, heat shock gene promoters, cold-induced promoters, drought-inducible gene promoters, pathogen-inducible gene promoters, wound-inducible gene promoters, and light/dark-inducible gene promoters, promoters from genes induced by abscissic acid, auxins, cytokinins, and gibberellic acid, as described in U.S. Pat. No. 7,632,983 to Dickey et al.

In an advantageous embodiment, the vectors used for expression include, 5' of the coding sequence of the expression cassette, a signal peptide sequence placed in frame with the N-terminal portion of the protein of interest. Such signal peptide sequence interacts with a receptor protein on the membrane of the endoplasmic reticulum (ER) to direct the translocation of the growing polypeptide chain across the membrane and into the endoplasmic reticulum for secretion from the cell. Presence of the signal peptide sequence ensures efficient secretion into the extracellular space. This signal peptide is generally cleaved from the precursor polypeptide to produce a mature polypeptide lacking the signal peptide. Suitable signal peptide include the *Arabidopsis thaliana* chitinase signal peptide, the *Oryza sativa* α-amylase signal peptide, or any other suitable duckweed signal peptide sequences, as described in U.S. Pat. No. 7,632,983 to Dickey et al. In a most preferred embodiment, the sequence of the signal peptide used in the *O. sativa* α-amylase signal peptide. In some embodiments of the present invention, the secreted SIgAs are retained within the apoplast, the region between the plasma membrane and the cell wall. In other embodiments, the polypeptide diffuses across the cell wall of the plant host cell into the external environment/media.

Other suitable nucleotide sequences including enhancers, 5' leader sequences, such as the leader sequence of *L. gibba* ribulose-bis-phosphate carboxylase small subunit 5B gene, 3' UTR sequences, introns, enhancers, "ACC" and "ACA" trinucleotides to be introduced directly upstream of the translation initiation codon of the nucleotide sequence of interest can be used to improve expression as disclosed in the art and in U.S. Pat. Nos. 6,040,498 and 7,161,064 to Stomp et al as well as 7,622,573 & U.S. Pat. No. 8,034,916 7,632,983 to Dickey et al, disclosures of which are all incorporated by reference herein.

For example, the expression from the transgenic lines obtained can be improved by optimizing the codon distribution of the encoded proteins for expression in duckweed. Duckweed-preferred codons, as used herein, refers to codons that have a frequency of codon usage in duckweed of greater than 17%. Likewise the codons can be optimized for expression in *L. minor* or *L. gibba*. In each case the codons have a frequency of codon usage of greater than 17%. Duckweed and *Lemna* ssp. codon optimization is known in the art and is carried out, e.g. as described in U.S. Pat. No. 7,632,983 to Dickey et al.

Another option is to modify the glycosylation profile of the duckweed. The stably transformed duckweed can also contain a genetic modification that alters the glycan profiles. For example, the N-glycans of the SIgA can be expressed with reduced levels of fucose and xylose residue, preferably less than 10%, more preferably less than 1%. This modification from natural glycan profile can be achieved by several techniques, including knocking out endogenous α1,3-fucosyltransferase (FucT) and β1,2-xylosyltransferase (XylT), or otherwise inhibiting their transcription of the gene/expression or enzymatic activity. In a preferred embodiment, the duckweed is transformed with at least one recombinant nucleotide construct that provides for the inhibition of expression of α1,3-fucosyltransferase (FucT) and β1,2-xylosyltransferase (XylT) in a plant. In a more preferred embodiment, these constructs triggers RNA interference targeting the mRNAs of α1,3-fucosyltransferase (FucT) and β1,2-xylosyltransferase (XylT). In an even more preferred embodiment, the construct is a RNA hairpin construct. These methods for altering the N-glycosylation pattern of proteins in duckweed are known in the art and are described in U.S. Pat. No. 7,884,264 to Dickey et al. The use of the RNA hairpin construct can be advantageous for obtaining a glycan profile where at least 30% of the N-glycans are G0 glycans lacking Fuc and Xyl residues and/or where the combination of G0 glycans lacking Fuc and Xyl plus high-mannose glycans are at least 70% relative to the total amount of N-glycans in the plurality of secretory IgA antibodies.

Once the transformed duckweed is obtained, the genetic modification will cause the duckweed to express the desired SIgA antibody during its otherwise normal metabolic activity. The term "express" and its grammatical variants refers to the biosynthesis of the SIgA antibody, which includes the transcription, translation, and assembly of the antibody by the duckweed. Generally this entails providing an environment to keep the duckweed alive and/or to promote growth; e.g., providing light (natural and/or artificial) and a liquid medium typically based on water. Providing this environment is often referred to as "culturing" the duckweed. Methods of culturing duckweed including the media, supplements (if any), conditions, etc., are known in the art and have been disclosed in, e.g., U.S. Pat. Nos. 6,040,498; 7,161,064; and 7,632,983; and references cited therein, respectively.

Culturing of transgenic duckweed of the invention can be performed in transparent vials, flask, culture bags, or any other container capable of supporting growth using defined media. In some embodiments of the invention large scale growth of duckweed, necessary to achieve industrial production levels, is carried out in bioreactor tailor-designed for growth of duckweed. In a preferred embodiment, duckweed bioreactors, which can be inoculated aseptically, support aseptic growth of duckweed. In even more preferred embodiments, a bioreactor can be directly connected to harvest bag to separate the media from the plant material, either of which can then be piped into downstream purification steps. Suitable bioreactors, methods/devices to inoculate them aseptically, and aseptic harvest bags are described in U.S. Pat. No. 7,176,024 to Branson et al. or in US application 2010/209966 To Everett et al.

Following expression of the fully formed SIgA antibody, recovery of the antibody from the duckweed and/or the culture media is often desired. The first step, generally, is to separate the SIgA antibody from the duckweed. If the antibody is secreted and diffuses into the culture media, then a simple filter can separate the crude antibody product from the duckweed. Typically, however, the fully formed SIgA antibody is retained within the duckweed's apoplast. Separation in this case generally requires extraction.

Extraction of secreted SIgAs typically involves a homogenization step to disrupt the plant material and allow for release of the secreted SIgA from the apoplast into the homogenization buffer; also referred to as extraction buffer or extraction media. Homogenization buffers and techniques are known in the art. Small scale homogenization can be performed manually, such as by using mortar-and-pestle crushing, and the like. Larger scale homogenization is preferably performed using a mechanical mixer, typically a high shear mixer such as a Silverson 275 UHS mixer, or similar apparatuses. The buffer is typically an aqueous phosphate buffer composition though such is not required. The buffer may contain additional functional ingredients as is known in the art. For example, to reduce proteolysis by metallated proteases, EDTA may be added to the extraction buffer, typically in amounts from 1 to 20 mM, including 5 to 10 mM. Also, one or more anti-oxidants, such as ascorbic acid, sodium metabisulfite, benzyl alcohol, benzoic acid, and the like, may be added during the homogenization process. Homogenization is generally followed by centrifugation and filtration to obtain a buffer solution that contains the SIgA antibodies and other soluble proteins.

To remove some of the unwanted soluble proteins, homogenization is often followed by clarification; a step that seeks to remove certain naturally abundant impurities including (host cell proteins), such as RuBiSco, as well as non-proteinaceous impurities, such as tannins. This is usually achieved by acidic precipitation. For example, clarification can be performed by adjusting the pH of the filtrated homogenate to 4.5, followed by centrifugation (such as for 30 min at 12000), neutralization to pH 7.4, and an additional filtration step. In a preferred embodiment, pH adjustments are performed using 1 M citric acid pH 1.5, or 1M sodium acetate for acidification and 2M tris-base for neutralization, though other suitable pH adjusting agents can also be used instead of or in addition to such agents. Filtration is performed as known in the art, often by using a 0.22 μm filter.

The recovery of the SIgA antibodies from duckweed may end with the extraction buffer or the clarified material. However, for some uses, purification of the antibody is desired. Purification can be performed using known methods and techniques and generally comprises subjecting the clarified material to affinity chromatography (AC), size exclusion chromatography (SEC), and optional polishing steps. For efficiency, AC usually precedes SEC, though such is not required.

Methods of using affinity chromatography (AC) as a purification step to remove contaminant proteins and impurities are known in the art and are described in Process Scale Purification of Antibodies (2009), Edited by U. Gottschalk, J. Wiley and son, Hoboken, N.J., and references cited therein. Usually the SIgA antibody is bound to the affinity resin material while one or more impurities are not bound. The conditions are modified and the previously bound SIgA antibody is eluted from the column. The opposite can also be performed with the desired antibody passing though and the impurity or impurities being bound to the column. The light chain constant region can be the affinity target. Useful affinity columns include KappaSelect and Capto L from GE Healthcare Life Sciences (Piscataway, N.J., USA). When KappaSelect is used, the addition of $MgCl2$ is often advantageous. The use of Protein A as an AC column is usually avoided. Another kind of AC step is known as IMAC (immobilized copper affinity chromatography). IMAC can be used as the sole AC step or in combination with more traditional AC steps. When used, IMAC is often carried out first. If the crude antibody composition, such as the clarified material, contains EDTA, then it is advantageous to add $CuSO4$ to the column in order to remove EDTA, which interferes which the IMAC purification process. Often IMAC is used for small to medium scale purification of SIgA where the amounts are less than 10 g, typically less than 5 grams.

Methods of using SEC for purification of monoclonal antibodies are known in the art. In general, SEC allows the separation of fully assembled SIgAs of interest from lower molecular forms (such a monomer of IgA, J-chain and SC-chain, or combinations thereof). Furthermore, SEC also permits a buffer change, such as, for example, the reformulation of the SIgA of interest into a new desired buffer. Suitable columns include, for example, a Sephacryl S300 HR column.

Other purification steps can be employed as well. For example, ion exchange chromatography (IEX) can be useful for removing colored impurities associated with the plant material. Methods and techniques for performing IEX chromatographic purification of antibodies are known in the art and are described, e.g., in Graf et al. (1994) "Ion exchange resins for the purification of monoclonal antibodies from animal cell culture" Bioseparation, vol. 4, no. 1 pages 7-20, or in "Process scale purification of antibodies (2009) Edited by U. Gottschalk, ed. J. Wiley and son, Hoboken, N.J., and references cited therein. Often IEX, such as anion exchange chromatography (AEX) or cation exchange chromatography (CEX), is performed before IMAC or other AC step is employed, but is not limited thereto and can be employed at other points of the purification and/or can be employed multiple times with the same or different exchange resin (e.g., AEX and subsequently CEX). In some embodiments an AEX column such as DOWEX 1X2 is employed, often before the AC column.

Further polishing/purification steps can be added, as is known in the art. For example, after any and/or each purification step (chromatography step) an ultrafiltration (UF) step can be performed. Typically, a UF step is performed at or near the end of the polishing phase in order to increase purity and/or change the buffer or concentration of antibody in the buffer.

The SIgA antibodies are often sufficiently recovered so as to be "isolated" or in an isolated form. Isolation is thus related to purification and is generally achieved by completion of the recovery/extraction step, clarification, and/or capture steps described above.

Pharmaceutical Compositions

The SIgA antibodies of the invention can be used in various pharmaceutical compositions. Typically the pharmaceutical composition comprises the antibody and at least one pharmaceutically acceptable excipient. The pharmaceutical compositions can be solid, semi-solid, or liquid. Generally the pharmaceutical composition is adapted for a particular route of administration. For example, the pharmaceutical composition can be adapted for oral administration, rectal administration, buccal administration, topical administration, etc. Preferably, the pharmaceutical composition is adapted for oral administration.

Pharmaceutical compositions for administering SIgA antibodies via topical administration include powders, creams, ointments, gels, lotions, solutions and suspensions (including mouth washes). The excipient carrier is often aqueous, oil, or polymer based, each optionally in the form of an emulsion or microemulsion. The term "topical administration" includes, for example, optical administration (e.g., via a cream/ointment) and administration to the skin (e.g., at an inflamed joint).

Pharmaceutical compositions for administering the antibody via oral administration include solid oral dosage forms such as tablets, capsules, enteric coated forms thereof, lozenges, and films, as well as liquid dosage forms including solutions, suspensions, liquid filled capsules, and mouth washes. Tablets can be soluble tablets, dispersible tablets, effervescent tablets, chewable tablets, lyophilized tablets, coated tablets (e.g., sugar-coated or enteric-coated), and modified release tablets. Capsules include hard gelatin capsules that can be filled with powder, pellets, granules, small tablets, or mini-tablets, or solutions or emulsions or combinations and can be coated for enteric or modified release. Soft capsules are also contemplated and are more typically filled with liquids, gels or dispersions, but are not limited thereto. Granules can be effervescent granules, coated granules (e.g., sugar-coated or enteric-coated), and modified release granules. Although the SIgA antibody of the present invention is preferably administered orally, it should be understood that such administration may be considered to be a topical administration to the GI tract. Likewise, a suppository or rectal injection may also be used to topically treat the intestines. The use of an oral dosage form to treat gastrointestinal disease(s) using the sIgA of the present invention is a specific aspect of the present invention.

Pharmaceutical compositions for administering the SIgA antibody via parenteral administration are typically liquid. Water is commonly used as a main excipient, although other pharmaceutically-acceptable liquids such as ethanol, glycerol, ethyl oleate, Myglyol, benzyol oleate, castor oil, MCT, benzyl alcohol isopropyl myristate can be used alone or in combination with water or each other. Aqueous compositions that contain no other excipients are also contemplated, and can be prepared from lyophilized, amorphous, or crystalline compounds. Often the injectable composition, which can be for subcutaneous, IM, or IV injection, contains isotonizing agents. An injectable solution or suspension is typically sterile, as are all liquid pharmaceutical dosage forms.

An overview of dosage forms can be found in *Ansel's Pharmaceutical Dosage forms and Drug Delivery Systems.* $9^{th}$ ed. L. V. Allan, N. G. Popovitch, H. C. Ansel, 2010

Lippincott, ISBN: 978-0781779340; *Formularium der Nederlandse Apothekers.* 2004 WINAp ISBN 90-70605-75-9; *Recepteerkunde,* G. K. Bolhuis, Y. Bouwman-Boer, F. Kadir en J. Zuiderma, 2005 WINAp ISBN 90-70605-65-1; and *Apothekenrezeptur und-defektur. Deutscher Apotheker Verlag* Stuttgart 1986 ISBN 3-7692-1092-1. See also U.S. Pat. No. 7,147,854 for a description of topical preparations for delivering IL-8 antibodies to treat skin inflammatory disease such as psoriasis.

The pharmaceutical composition generally contains about 0.01 to 1000 mg of the antibody per dose, depending in part upon the dosage form employed. The dose can be, for example, fixed or variable (e.g, based on body weight) Pharmaceutically-acceptable excipients are known in the art and include diluents, carriers, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, preservatives, antioxidants and specialized oils. Specific to the field of biopharmaceutical proteins are excipients intended to stabilize proteins and cryo-protectants to provide protection during freeze-drying. Suitable excipient(s) are selected based in part on the dosage form, the intended mode of administration, the intended release rate, and manufacturing reliability. Non-limiting examples of commonly used excipients include polymers, waxes, calcium phosphates, sugars (e.g., trehalose, sucrose, or mannitol), buffers (such as phosphate, acetate, citrate, histidine, or glycine based buffers at pH between 5 and 7.5), salts (e.g., NaCl or NaEDTA), polysorbate 20, polysorbate 80, human albumin, dextran, and benzyl alcohol.

Treatments

As used herein, the term "treat" or "treatment" means the application or administration of a SIgA antibody of the invention, alone or as part of a composition, to a patient with the purpose to cure, heal, alleviate, improve or prevent an inflammatory disease. The term "inflammatory disease" means a condition associated with symptoms of inflammation, which may be caused by external factors, such as infectious disease, or by internal dysfunctions, such as an autoimmune disease. In this context, the terms disease, disorder, syndrome, condition, and the like are used interchangeably. In embodiments, the SIgA antibodies of the present invention are useful in the topical treatment of inflammatory diseases in humans, e.g., local administration to the site of inflammation, such as orally or rectally. Preferably, the SIgA antibodies of the present invention are useful in the oral treatment of inflammatory diseases.

As used herein, an amount of the SIgA of the present invention effective to treat an inflammatory disease, or a "therapeutically effective amount," refers to an amount of the antibody which is effective beyond that which is expected in the absence of such treatment.

As used herein, the term "patient" is intended to include humans and non-human animals. The term "non-human animals" includes all vertebrates, e.g., non-mammals (such as chickens, amphibians, reptiles) and mammals, such as non-human primates, sheep, dog, cow, horse, pig, etc. In a preferred instance, the patient is human.

The SIgA antibodies of the present invention are generally useful in treating inflammatory diseases in a human. Specific targets of inflammation include rheumatoid arthritis (RA), inflammatory bowel disease (IBD, which includes Crohn's disease and ulcerative colitis), psoriasis, psoriatic arthritis, ankylosing spondylitis, juvenile idiopathic arthritis (JIA), uveitis, (eosinophilic allergic) asthma, and Alzheimer's disease.

In a preferred embodiment, the SIgA antibodies of the present invention are orally administered to treat inflammation, inflammatory diseases or disorder, and/or autoimmune disorders of the gut. It should be understood that "treating" in this context includes prophylactic treatment as well as symptomatic treatment. The amount administered to be effective for prophylactic or symptomatic treatment can be determined by routine skill and experimentation for the given patient and condition and will often be in the range of 0.1 mg to 1000 mg per day. The constant regions of the SIgA antibody preferably are the same as, or closely resemble, the normal or natural constant regions of IgA found in the species of patient to be treated as such is believed to minimize the patient's immune response to antibody. The antibody can be administered by itself, such as by a capsule containing the lyophilized protein or as a plant extract added to food, etc., or, in a pharmaceutical composition such as a tablet or capsule.

In other embodiments, the SIgA antibodies of the present invention targets include skin disorders such as psoriasis, acne ectopica (hidradenitis suppurativa), oral aphta (aphthous stomatitis), bullous and cicatricial pemphigoid, mucocutaneous symptoms of Behcet's Disease, dermatomyositis, erythema annulare centrifugum, skin manifestations of graft-versus-host-disease, non-infectious (non-caseating) granulomatous skin diseases, including granuloma annulare, granuloma cheilitis, and granulomatous rosacea. Additionally, inflammation and/or disorders of the eye such as uveitis can also be a target of the SIgA antibodies of the present invention. The SIgA antibody of the invention can be administered systemically such as via injection and in some circumstances orally. Preferably the antibody can be administered locally by topical application (lotion or ophthalmic compositions, etc.) or by local injection near the affected area; e.g., subcutaneous injection or an injection in the eye.

Additional conditions include those recited in U.S. Pat. Nos. 5,656,272, 5,919,452, 6,790,444, 5,605,690, 6,090,382, 7,012,135 and 7,186,820 and include any TNF-α-mediated diseases, disorders, or conditions wherein reduction of TNF-α is desirable.

EXAMPLES

The present invention will be further illustrated in the following non-limiting examples.

Example 1

Transient Expression of an Anti-TNF-α Secretory Protein Based on Infliximab (IIB-SA2n) in Plants a) Preparation of cDNA Constructs The amino acid sequences of a suitable leader sequence (e.g., secretion signal, SEQ NO:23), the heavy chain variable region of infliximab (SEQ ID NO:2), and the human α2(n) IgA heavy chain constant region (Chintalacharuvu et aL, *Journal of Immunology,* 1994, 152, 5299-5304; SEQ ID NO:13) were joined together. Cleavage of the signal sequence (a.a. 1-19) corresponded to the predicted cleavage site using the SignalP program This program is available online via the site of the Center for Biological Sequence Analysis at the Technical University of Denmark.

The resulting amino acid sequence was back-translated into a cDNA sequence optimized for expression in maize (Z.

*mays*) (SEQ ID NO:27) (see Liangjiang Wang and Marilyn J. Roossinck., "Comparative analysis of expressed sequences reveals a conserved pattern of optimal codon usage in plants." *Plant Mol Biol* (2006) 61:699-710).

Similarly the cDNA sequence for the light chain of the construct was obtained by joining the sequences of a suitable secretion signal (SEQ ID NO:24), the light chain variable region of infliximab (SEQ ID NO:3), and the human κ Ig light chain constant region (SEQ ID NO:14), and back-translating the obtained amino acid sequence into a cDNA sequence optimized for expression in maize (*Zea mays*) (SEQ ID NO:29).

The cDNA sequence for the human J-chain was obtained by joining the amino acid sequences of secretion signal (SEQ ID NO:22) and J-chain sequence (SEQ ID NO:20), both obtained from UniprotKB/Swiss-Prot database entry P01591, and back-translating the obtained amino acid sequence into a cDNA sequence optimized for expression in maize (*Z. mays*) (SEQ ID NO:33).

The cDNA sequence for the SC-chain was obtained by joining the amino acid sequences of a suitable secretion signal (SEQ ID NO:25) and SC-chain sequence (SEQ ID NO:21, amino acids 19-603 of UniprotKB/Swiss-Prot database entry P01833), and back-translating the obtained amino acid sequence into a cDNA sequence optimized for expression in maize (*Z. mays*) (SEQ ID NO:35). The used secretion signal sequence was derived from the natural SC secretion signal by the addition of codons for two extra amino acids in order to obtain more favorable splicing sites for the construction of plasmid vectors.

The cDNA's of the four constructs (the heavy chain, the light chain, the J-Chain and the SC-Chain) were obtained from a commercial source.

b) Vector Construction and Cloning Strategy

The cDNAs for the heavy chain of the construct (HC) and of the J-chain (JC) were ligated into the pGA15 and pGA14 plasmid vectors, respectively, using PacI and AscI restriction sites. After transfer to *E. coli* K12 XL10 gold and expansion, the constructs were each transferred to separate pRAP plasmids using NcoI and KpnI restriction sites, resulting in the expression cassettes 35S:HC:Tnos and 35S:JC:Tnos. The pRAP plasmids containing the expression cassettes were transferred to and expanded in *E. coli* K12 DH10B.

The cDNAs for the light chain (LC) and of the SC-chain (SC) were ligated into the pGA14 and pGA15 plasmid vectors, respectively, using PacI and AscI restriction sites. After transfer to *E. coli* K12 XL10 gold and expansion, the constructs were each transferred into separate pTR2 plasmids using NcoI and XbaI restriction sites, resulting in the expression cassettes TR1'TR2':LC:T35S and TR1'TR2':SC:T35S. The pTR2 plasmids containing the expression cassettes were transferred to and expanded in *E. coli* K12 DH10B.

The light chain expression cassette TR1'TR2':LC:T35S was transferred to the pRAP vector containing the heavy chain expression cassette 35S:HC:Tnos using HindIII restriction sites, and transferred to and expanded in *E. coli* K12 DH10B. Finally, the combined cassettes containing HC and LC (35S:HC:Tnos:TR1'TR2':LC:T35S) were transferred to a pBIN+ expression vector using AscI and PacI restriction sites. This pBIN+ vector containing the combined HC and LC cassettes was transferred to *Agrobacterium tumefaciens* strain MOG101 using electroporation. Similarly the cassettes containing JC and SC (35S:JC:Tnos:TR1'TR2':SC:T35S) were combined in a pBIN+ expression vector. This pBIN+ vector containing the combined JC and SC cassettes was transferred to *A. tumefaciens* strain MOG101 using electroporation.

The two transfected *A. tumefaciens* strains were used in combination for transient plant transformation and expression of the full SIgA construct. For vector information see also van Engelen et al., *Plant Molecular Biology* 1994, 26: 1701-1710. Information on A1MV leader sequence: van der Vossen et al., *Nucleic Acids Research* 1993, 21: 1361-1367. pBIN+ is described in: van Engelen et al., Transgenic Research 1995, 4: 288-290. (In the referenced literature sources: pRAP35=pCPO31). By way of example, FIG. 6 shows a schematic representation of the building of the pBIN+ vector containing the combined HC and LC cassettes.

c) Transient Expression in Tobacco Plants

The youngest fully expanded leaves of six week old tobacco plants were infiltrated with a mixture of the two *A. tumefaciens* strains by placing a 2-ml syringe (without needle) containing the bacterial cell suspension at the lower side of a leaf and gently pressing the suspension into the leaf. The infiltrated area was usually clearly visible. Expression took 4-6 days with optimum levels at days 5-6.

The leaves were frozen at −80° C., crushed and 2 ml extraction buffer per gram of leaf material was added. The extraction buffer was PBS pH=7.4; 0.02% Tween-20 (v/v); 2% polyclar AT (v/v); and 1% inhibitor cocktail (v/v). The suspension was homogenized with an Ultra Turrax (Janke & Kunkel). Solid material was removed by centrifugation (15 minutes, 10.000 g). The solid material was extracted twice more with extraction buffer, the same as above except the inhibitor cocktail was replaced with 10 mM PMSF. The combined extracts were stored at −20° C. Using SDS-page and immunoblotting, formation of a complete SIgA could be shown, but the product was not isolated or purified. The SIgA comprises IgA(2)(n) heavy chain constant region, human κ light chain constant region, and the heavy and light chain variable regions of infliximab, and is referred to herein as "IIB-SA2n"

d) Transient Expression in Lettuce

The SIgA construct was transiently expressed in lettuce by vacuum infiltration using the same vectors as for expression in tobacco (see: Negrouk et al., Highly efficient transient expression of functional recombinant antibodies in lettuce., Plant Science 2005, 169, 433-438). Full grown crops of lettuce *Lactuca sativa* L. (oak leaf lettuce) and vacuum infiltrated with a mixture of the two *A. tumefaciens* strains and harvested 3-5 days after infiltration. Formation of complete SIgA could be shown, but the product was not isolated or purified.

Example 2

Expression of an Anti-TNF-α Secretory Protein Based on Infliximab (IIB-SA2n) in Mammalian Cells 2a: Transient Expression of IIB-SA2n (1) Vector Generation:

cDNAs encoding SIgA heavy chain (HC), light chain (LC), J-chain, and SC-chain were cut from the pGA14 and pGA15 plasmids described in Example 1. The excised HC and LC sequences were PCR amplified and cloned into pMQR-hIgG1 (Neo) to give pMQR-zma2-iib (Neo) and pMQR-zmκ-iib (Neo) vectors. Similarly, the excised J-chain and SC-chain were PCR amplified and cloned into pMQR-kappa (Hygro) to give the pMQR-zmJ (Hygro) and pMQR-zmSC (Hygro) vectors. The pMQR-hIgG1 (Neo) and pMQR-kappa (Hygro) vectors are based on the pcDNA3 (Invitrogen) backbone, which was modified to receive any combination of Ig V- and C-region "cassettes". This was performed by subcloning well-defined genomic Ig gene segments into pcDNA3, after which silent mutations were introduced flanking the V- and C-regions to create restrictions sites allowing for the exchange of V- and C-gene segments. Other occurrences of these specific introduced restriction sites were removed from the vector backbone to ensure proper exchange of V and C regions on unique restriction sites. In short, the BsmI site was removed by exchanging the original BsmI sequence (5'-TGCATTC-3') present in the vector into 5'-TGCAAAC-3'. Furthermore the MunI/MfeI and HindIII sites were destroyed by restriction digestion followed by end-filling and re-ligation.

Large-scale production of each of the four expression vectors for transfection was performed using Maxiprep-kits (Sigma).

(2) Cell Transfection and Culture:

Transient SIgA producing CHO-S and HEK-293F cells (Invitrogen) and HEK293-EBNA1 (ATCC CRL-10852) were made as follows: Invitrogen derived cell types were used as host for transfection using FreeStyle Max or Amaxa Nucleofection. HEK293-EBNA1 was used for large scale (10 l) transient polymer transfection. To obtain a complete SIgA-producing transfectant, all 4 different vectors were transferred simultaneously into each of these cell types (CHO-S, HEK293F, and HEK203-EBNA1).

(3) FreeStyle MAX Transfection

To transfect 30×10⁶ CHO-S and HEK-293F cells (separately), 9,375 ug of each vector was used. SIgA production was performed by culturing cells in a 200 ml shake flask at 37° C., 130 rpm and 8% $CO_2$ during 120 hours in respectively CHO-S FreeStyle and 293F FreeStyle medium. The cell conditions and transfection efficiency were determined by GUAVA ViaCount and Expresse Pro analysis to guarantee the optimal cell growth conditions in between 0.5×10⁶ to 2.0×10⁶ cells/ml. Each time the cells had to be diluted the volume was increased and if necessary transferred to a 500 ml baffled shake flask.

CHO-S/SIgA 24 hours post transfection: Transfection efficiency; 25.04% and cell viability; 91.59%.

HEK-293F/SIgA 24 hours post transfection: Transfection efficiency; 25.52% and cell viability; 80.36%.

(4) Amaxa Transfection

To transfect 1×10⁶ Invitrogen's CHO-S or HEK-293F cells 1 ug of each vector was used. SIgA production was performed by static culturing cells in a T25 flask at 37° C. and 5% $CO_2$ during 96 hours. At 96 hours post transfection cell suspensions fractions were taken for production analysis.

CHO-S/SIgA 24 hours post transfection: Transfection efficiency; 54.27% and cell viability; 94.19%.

HEK-293F/SIgA 24 hours post transfection: Transfection efficiency; 61.57% and cell viability; 68.15%.

(5) Polymer Transfections

Transfections of HEK293-EBNA1 cells were performed essentially as described by Durocher at al. *Nucleic Acids Res.* 30, E9 (2002) (see also Morlot C. et al., *Acta Crystallogr Sect F Struct Biol Cryst Commun.* 63, 689-91 (2007)). The day prior to transfection, the cells were routinely diluted 4-5 times in fresh Freestyle medium (without further addition of FCS or G418) to a density of 0.3×10⁶/ml. The next day transfection mixtures were prepared. For transfection of 1 liter of cell culture 500 µg of high quality DNA was diluted in 25 ml OptiMEM medium (Invitrogen) 1 ml of a 1 mg/ml stock solution of linear 25 kDa PEI (Polysciences) was added to the mixture and immediately vortexed for 10 seconds. After 10 minutes for incubation the DNA:PEI mixture was added to the cells. Cells or conditioned medium were routinely harvested six days post transfection. Culture was performed at 10 L scale. The anti-TNF-α secretory IgA antibody, IIB-SA2n, in the supernatant of this culture can be isolated and purified as described in Example 3a.

2b: Stable Expression in HEK293F of IIB-SA1

(1) Vector Construction cDNA encoding the heavy chain variable region of infliximab was cut from the previously obtained vector pMQR-zma2-iib (Neo) (see Example 2a(1)). This cDNA was fused into a pMQR vector containing the human genomic DNA sequence encoding the IgA α1 heavy chain constant region to give vector pMQR-hα1-iib (Neo). Similarly, the light chain variable region of infliximab was cut from pMQR-zmκ-iib (Neo) and transferred to a pMQR vector containing the human genomic DNA sequence encoding the K-light chain constant region to give vector pMQR-huκ-iib (Neo). The two vectors pMQR-huα1-iib (Neo) and pMQR-huκ-iib (Neo) were fused into a single vector pMQR-huIgA1-iib (Neo) (SEQ ID NO:28).

Previously obtained vectors pMQR-zmJ (Hygro) and pMQR-zmSC (Hygro) were also combined into a single vector PMQR-zmJ/SC (Hygro) (SEQ ID NO:30).

(2) Transfection

HEK-293F cells were transformed with both of the two vectors described above using polymer transfection as described in experiment 2a(5). Cells were grown in neomycin and hygromycin containing medium. After recovery, cells were grown on semisolid medium with neo/hygromycin and clones were selected using Clonepix analysis and selection. A suitable clone (2D5) was selected. Clone 2D5 was expanded under various conditions and scales. Ultimately 15 L of culture medium containing 440 mg of complete SIgA (according to ELISA analysis) was obtained from the expanded 2D5 cells. The SIgA comprises IgA(1) heavy chain constant region, human κ light chain constant region, and the heavy and light chain variable regions of infliximab; and is referred to herein as "IIB-SA1." IIB-SA1 can be isolated from culture medium and purified as described in Example 3b.

Example 3

Purification of Anti-TNF-α Secretory IgA Antibodies (IIB-SA2n and IIB-SA1) from Mammalian Cell Culture 3a—Affinity and SEC (IIB-SA2n)

The supernatant obtained from the transient expression of IIB-SA2n in HEK-293-EBNA1 cells using polymer transfection (experiment 2a(5)) was purified using affinity chromatography with an anti-IgA lama antibody fragment immobilized on sepharose (CaptureSelect human IgA, BAC, product code 2880) followed by SEC.

(1) Affinity Chromatography:

Anti-human IgA matrix (Capture Select) was poured into a XK16/20 column (16×200 mm) in 20% ethanol in MilliQ water at a flow rate of 15 ml/min. After adjusting the position of the upper flow adaptor, the column was equilibrated in PBS buffer pH 7.4. The HEK-cell culture medium was filtered to remove large cell debris and subsequently loaded on the pre-equilibrated anti-human IgA column with a flow rate of 4.5 ml/min. After washing with 10 column volumes PBS pH 7.4, the active secretory IgA antibody was isocratically eluted from the column with 5 column volumes of citrate/arginine/NaCl buffer pH 2.5, followed by immediate neutralization to pH 7.7 with a 1 M Tris stock solution.

(2) SEC Chromatography:

In the second step, the adjusted pool from the first step was concentrated 4-fold down to 5 ml using a Vivaspin 15R device (30 kDa cut-off filter) and loaded on a prepacked Superdex 200 16/60 GL column equilibrated with PBS pH 7.4. The sample loading volume was 4% of the bed volume and the flow rate was 1.5 ml/min. This size exclusion gel filtration step resulted in fractionation of SIgA and monomeric IgA according to their molecular weights. The elution fractions containing SIgA or monomeric IgA as determined by non-reducing SDS-PAGE were pooled separately and subsequently concentrated 10-fold using a Vivaspin 15R device (30 kDa cut-off filter).

Samples of substantially pure IIB-SA2n and the corresponding monomeric anti-TNF-α IgA were collected and characterized.

3b—Jacalin Affinity and SEC (IIB-SA1)

Culture medium obtained from HEK-293F clonal cell line 2D5 expressing IIB-SA1 (see Example 2b) was purified using Jacalin affinity chromatography followed by SEC.

(1) Jacalin Affinity Chromatography 500 ml culture medium was filtered through a 0.45/0.2 µm Sartopore 2 filter. A Jacalin column was prepared by packing 15 ml of immobilized Jacalin resin (Pierce art nr. 20395) in an omnifit 15 mm glass column. The column was equilibrated using 5 column volumes of PBS buffer pH 7.4. Culture medium was loaded at a flow rate of 3 ml/min. after washing with 5 column volumes of PBS buffer pH7.4 at 5 ml/min followed by elution of bound material with 8 column volumes of PBS buffer pH7.4 containing 0.5M galactose. The fractions of the eluate containing SIgA were pooled (detection by UV OD280 measurement). The pooled eluate (64 ml) was concentrated to a volume of 5 ml using Vivaspin filters. Measurement of SIgA content using ELISA showed that only appr. 30% was bound to the Jacalin, the remainder being in the flow-through fraction.

(2) SEC Chromatography

Figure 7:
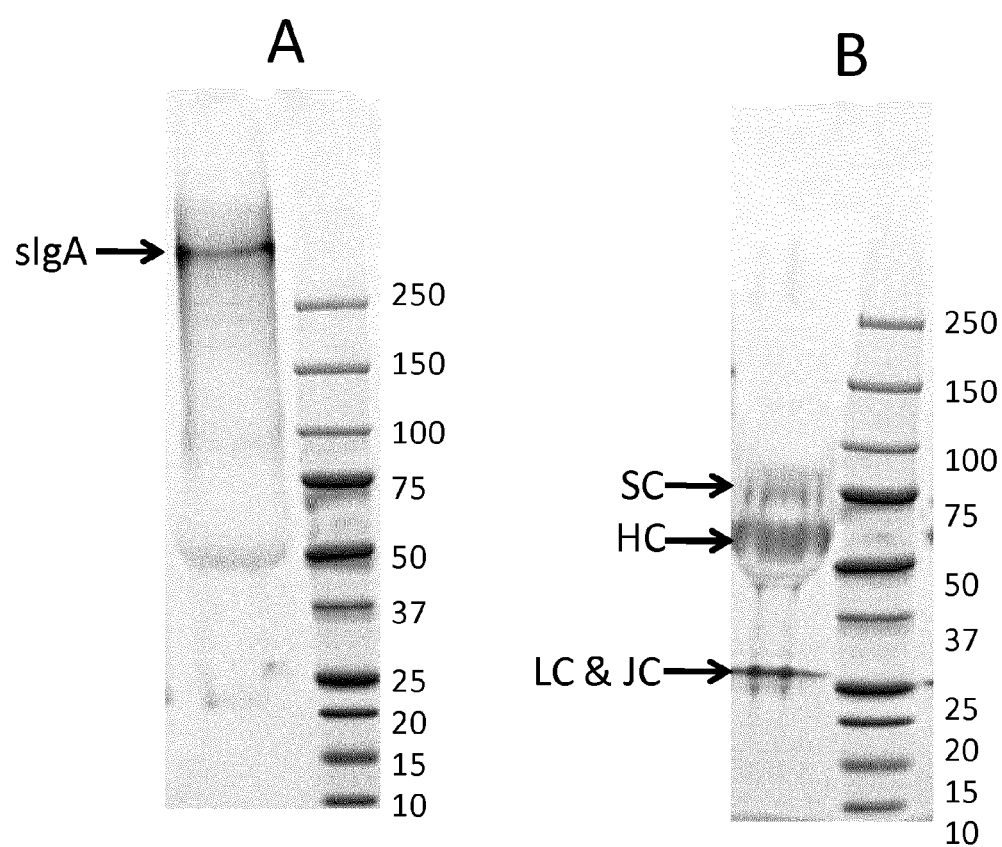
FIG. 7 shows reducing and non reducing gels of an anti-TNFα SIgA of the invention, having infliximab variable regions and being produced in mammalian HEK-293F cells. The label "A" shows non-reducing SDS-PAGE analysis demonstrating expression of complete SIgA while the label "B" shows reducing SDS-PAGE analysis.

The concentrated eluate was placed in a superloop and loaded on a Sephacryl S300 column (GE-Healthcare art.nr. 17-1167-01) with a flow rate of 1 ml/min. The product was eluted using 1.5 column volumes of PBS buffer (50 mM phosphate pH 7.4) containing 0.5M arginine. The chromatogram (UV OD280 detection) showed three overlapping peaks. Fractions were analysed by SDS-PAGE to identify the SIgA containing fraction. The fractions containing the product were pooled. Reducing and non-reducing SDS-PAGE analyses of the purified product, IIB-SA1, are shown in FIG. 7.

Example 4

Stable Expression of Anti-TNF-α Secretory IgA Antibody (ADB-SA1g) in *Lemna*

Anti-TNF-α SIgA was produced in *Lemna* by stable insertion of DNA coding for the following proteins: The amino acid sequence of the heavy chain consisted of the *Oryza sativa* (rice) amylase secretion signal (SEQ ID NO:26) attached to the N-terminal amino acid of the heavy chain variable region of adalimumab (anti-TNF-α IgG1, Humira®, CAS number 331731-18-1) (SEQ ID NO:4) attached to the N-terminal amino acid of a human IgA1 heavy chain constant region (SEQ ID NO:10). The amino acid sequence of the light chain of the Anti-TNF-α SIgA combines the rice α-amylase secretion signal (SEQ ID NO:26) with the TNF-α binding light chain variable region of adalimumab (SEQ ID NO:5) and the human κ-light chain constant region (SEQ ID NO:14). The amino acid sequence of the J-chain consisted of the rice α-amylase secretion signal (SEQ ID NO:26) attached to the N-terminal amino acid of the human J-chain (SEQ ID NO:20). The amino acid sequence of the SC-chain consisted of the rice amylase secretion signal (SEQ ID NO:26) attached to the N-terminal amino acid of the human SC-chain (SEQ ID NO:21). The produced SIgA, having IgA1 heavy chain constant region, human κ-light chain constant region, and adalimumab heavy and light chain variable regions, combined with human J-chain and SC-chain is referred to as ADB-SA1.

Genes were designed for each of the four components with *Lemna minor* preferred codon usage (63-67% GC content). Tables with suitable preferred codon use in Lemnaceae can be found in PCT application WO2005/035768 and in relevant references contained therein. The synthetic genes also contained the rice α-amylase signal sequence (GenBank M24286; SEQ ID NO:26) fused to the 5' end of their coding sequences. Restriction endonuclease sites were added to allow cloning into *A. tumefaciens* binary vectors. Design of DNA sequences and vector construction was performed by Biolex Therapeutics, Inc., Pittsboro, N.C., USA. DNA sequences were produced by DNA2.0 (Menlo Park, Calif., USA).

The ADB-SA1g antibody was expressed in *L. minor* by transfection via an *A. tumefaciens* binary vector containing DNA sequences encoding all four of the SIgA components: J-chain (SEQ ID NO:34), SC-chain (SEQ ID NO:36), H-chain (SEQ ID NO:31) and L-chain (SEQ ID NO:32). To prepare this vector, independent expression cassettes were created containing a promoter and also DNA sequences encoding the protein and terminator for the J-chain, SC-chain, H-chain and L-chain. The H chain was fused to the modified chimeric octopine and mannopine synthase promoter with *Lemna gibba* 5' leader from ribulose bis-phosphatecarboxylase small subunit-1. The L-chain, SC-chain and J-chain genes were fused to high expression Lemnaceae Ubiquitin promoters *L. minor* polyubiquitin promoter (LmUbq), *Lemna aequinoctialis* polyubiquitin promoter (LaUbq) and *Spirodela polyrrhiza* polyubiquitin promoter (SpUbq), respectively. Sequences of these promoters have been disclosed in PCT application WO2007/124186. These expression cassettes were then cloned into a single *A. tumefaciens* transformation vector EC2.2 (a modification of the *A. tumefaciens* binary vector pBMSP3, which is a derivative of pBINPLUS. See Ni, M., Cui, D., Einstein, J., Narasimhulu, S., Vergara, C. E., and Gelvin, S. B., *Plant J.* 7, 661-676, (1995), van Engelen, *Transgenic Res.* 4:288-290 (1995), and Gasdaska et al., *Bioprocessing J.,* 3:50-56 (2003)), with the appropriate restriction sites to create the final transformation vector SynB02. This vector also contained the gentamicin acetyltransferase-3-I gene (aacC1) which confers resistance to gentamicin and allows for selection of transgenic *L. minor* lines.

SynB02 was used to create an additional transformation vector to generate a glycan optimized version of anti-TNF-α SIgA, having G0 glycans lacking fucose and xylose residues. A chimeric hairpin RNA was used to silence endogenous *L. minor* mRNAs encoding α-1,3-fucosyltransferase (Fuct1, GenBank DQ789145) and β-1,2-xylosytransferase (Xylt1, GenBank DQ789146). A DNA sequence for this chimeric RNAi molecule was fused to the high expression SpUbq promoter and subsequently moved into the SynB02 vector creating the final transformation vector SynB03. Further details on production of glycan optimized proteins in Lemnaceae can be found in PCT applications WO2007/084672, WO2007/084922, WO2007/084926 and in Cox, K. M., *Nature Biotechnology* 2006, 12: 1591-1597.

*L. minor* strain 8627 was transfected with vector SynB03, and glycosylation modified *L. minor* strain XF04 was transfected with vector SynB02. Once transformed plants were regenerated (approximately three months), single plants were harvested from the antibiotic selection plates and propagated separately in liquid growth media, without selection antibiotic, for further screening and characterization. Thus several hundred individual transgenic plant lines from each construct were generated. Independent transgenic lines were harvested and clonally propagated in individual harvest jars. For screening of transgenic lines, clonal lines were preconditioned for 1 week at light levels of 150 to 200 $\mu mol/m^2 \cdot s$ in vented plant growth vessels containing SH medium (Schenk R. U. et al., *Can. J. Biol.* 1972, 50: 199-204) without sucrose. Fifteen to twenty preconditioned fronds were then placed into vented containers containing fresh SH medium, and allowed to grow for two weeks. Tissue samples from each line were collected and frozen for analysis.

To determine SIgA expression, frozen tissue samples were homogenized and centrifuged, and the supernatant was removed and screened by an ELISA method using sheep anti-human IgA secretory chain (AbD Serotec catalog #5111-4804—1:1000 dilution) coated plates to capture the SIgA antibody. The samples were then detected using a goat anti-human kappa light chain HRP conjugated antibody (Sigma catalog #A7164—1:2000 dilution). The highest-expressing lines from this primary screening were then grown again for two weeks in small research vessels under the optimal growth conditions. The resulting tissue was harvested and the ELISA was performed to determine the percent of the total soluble protein that is the expressed SIgA antibody (ADB-SA1g). The results are summarized in Table 1.

TABLE 3

| Construct | Glycosylation | # of lines screened | Highest Expression level |
|---|---|---|---|
| SynB02 | G0 glycans | 55 | 16.2% TSP |
| SynB03 | G0 glycans | 227 | 13.6% TSP |

Figure 8:
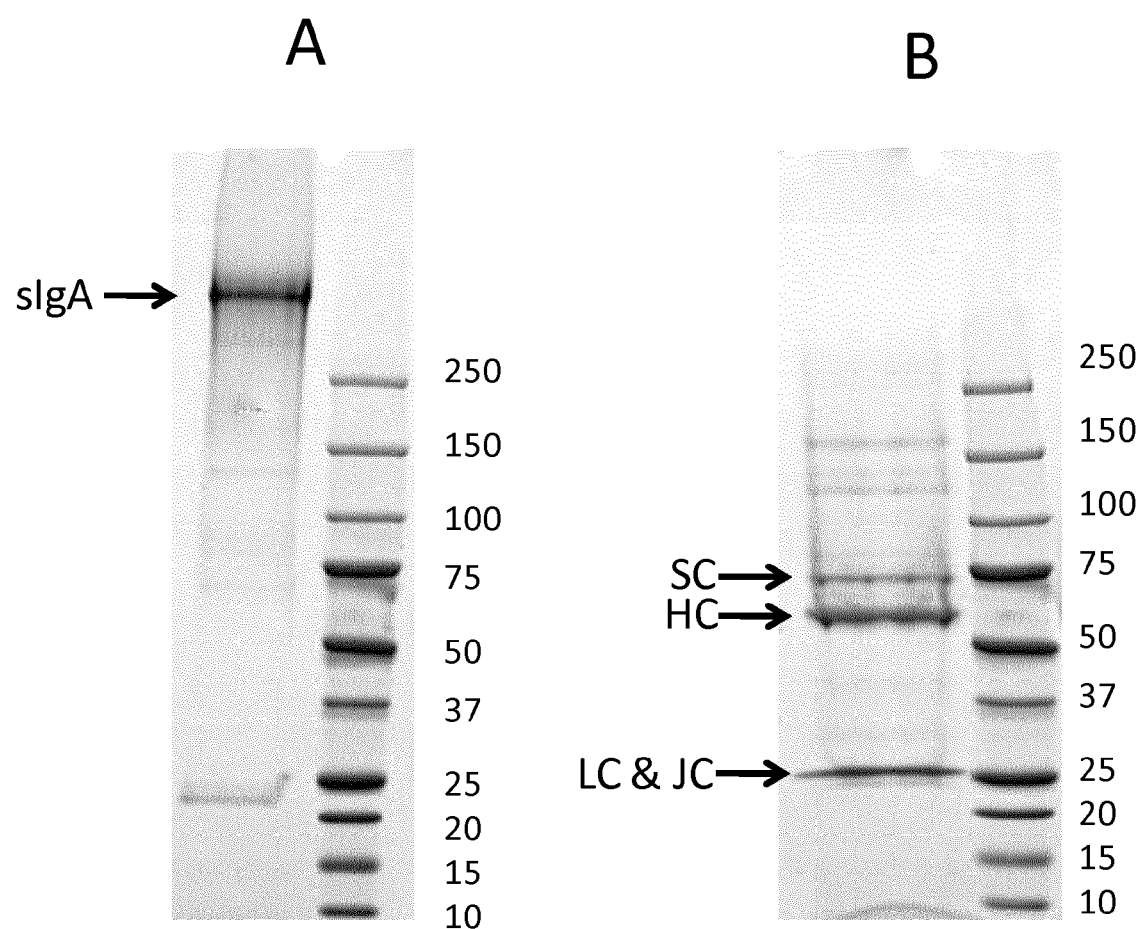
FIG. 8 shows reducing and non reducing gels of an anti-TNFα SIgA of the invention, having adalimumab variable regions and being produced in *Lemna*. The label "A" shows non-reducing SDS-PAGE analysis demonstrating expression of complete SIgA while the label "B" shows reducing SDS-PAGE analysis.

Results of non-reducing and reducing SDS-PAGE analyses of purified material obtained from *Lemna* transfected with construct SynB02 are shown in FIG. 8. ADB-SA1g can be isolated from *Lemna* culture and purified as described in Example 5.

Example 5

Isolation and Purification of Anti-TNF-α Secretory IgA Antibody ADB-SA1g from *Lemna*

Biomass from transgenic *Lemna* expressing anti TNF-α SIgA, having variable regions that are the amino acid sequence of the variable regions (antigen binding regions) of adalimumab, was homogenized in 50 mM Sodium phosphate, 0.3M Sodium chloride, buffer pH 7.4, at a buffer to tissue ratio of 4:1. An acid precipitation step was performed on the crude extract to remove ribulose bis-phosphate carboxylase (RuBisCo) and other plant proteins by adjusting the extract to pH 4.5 using 1M Sodium acetate, pH 2.5. The precipitate was removed by centrifugation of the material at 14,000×g for 30 minutes at 4° C. The supernatant was adjusted to pH 7.4 and loaded on DOWEX (Dowex 1X2 anion exchange resin) to remove colored impurities. The flow-through fraction containing anti TNF-α SIgA was 0.22 μm was filtered prior to chromatography using affinity chromatography and Size Exclusion Chromatography.

Affinity purification: A KappaSelect (GE Healthcare prod. Nr. 17-5458-03) column was prepared according to manufacturer instructions (28-9448-22 AA). The column was equilibrated with 5 column volumes (cv) of TBS buffer (50 mM Tris, 0.15M Sodium chloride, pH 7.4). The supernatant was loaded on the column Approximately 5 mg sIgA/ml resin was loaded on columns of up to 1 L KappaSelect. Non-binding material was washed from the column with 5 cv TBS buffer. The product was eluted from the column using 10 cv of 25 mM Sodium Acetate, pH 6.6 buffer containing 3.5 M $MgCl_2$. The fractions containing the secretory proteins were pooled and immediately diluted 4-fold using TBS buffer (50 mM Tris, 0.15M Sodium chloride, pH 7.4). $MgCl_2$ was replaced by buffer exchange with at least 10 volumes of TBS buffer using a Pall Centramate cassette ultrafiltration system and a Pellicon 2 Mini Filter (Millipore prod.Nr. P2C005C01-PLCCC 5K, regenerated cellulose) with 5 kDa cut-off.

SEC purification: Material obtained by KappaSelect chromatography was further purified on a Sephacryl 5300 HR column. The column was equilibrated with 2 cv of PBS buffer at a flow rate of 1.0 ml/min. The KappaSelect eluate was concentrated 3-4× using ultra filtration using a Pellicon 2 Mini Filter (Millipore prod.Nr. P2C005C01-PLCCC 5K, regenerated cellulose) with 5 kDa cut-off.

Typically, a concentration of 3-5 mg/ml and feed volume of 50 ml was used for a 1 L column. The feed was applied using an AKTA purifier at 1.0 ml/min. Elution was performed with at least 2 column volumes of PBS buffer at room temperature and a flow rate of 1.0 ml/min Fractions were collected and sufficiently pure fractions were pooled.

Example 6

Binding of Anti-TNF-α SIgA IIB-SA1 to TNF-α

Binding of IIB-SA1 (infliximab binding head) after purification as described in Example 3b, to TNF-α was determined using ELISA according to the following procedure.

96-Well plates were incubated overnight at 4° C. with 100 μl/well of 0.5 μg/ml TNF-α in PBS pH7.4. After emptying the wells were incubated for 2 hours at RT with 200 μl/well of PBS pH7.4 containing 1% BSA and 0.05% Tween-20. After washing (room temperature) with 300 μl/well of PBS/0.05% Tween-20 three times for 30 seconds, shaking, the plates were used. The wells were incubated with samples, 1 hour at 37° C., 100 μl/well. The wells were washed (room temperature) with PBS/0.05% Tween-20 three times for 30 seconds, shaking, 300 μl/well. The wells were incubated with 100 μl/well of 0.5 μg/ml HRP labeled anti-human kappa light chain antibody (Sigma, A7164) for 1 h at RT, and then washed (room temperature) with PBS/0.05% Tween-20 three times for 30 seconds, shaking, 300 μl/well.

Figure 9:
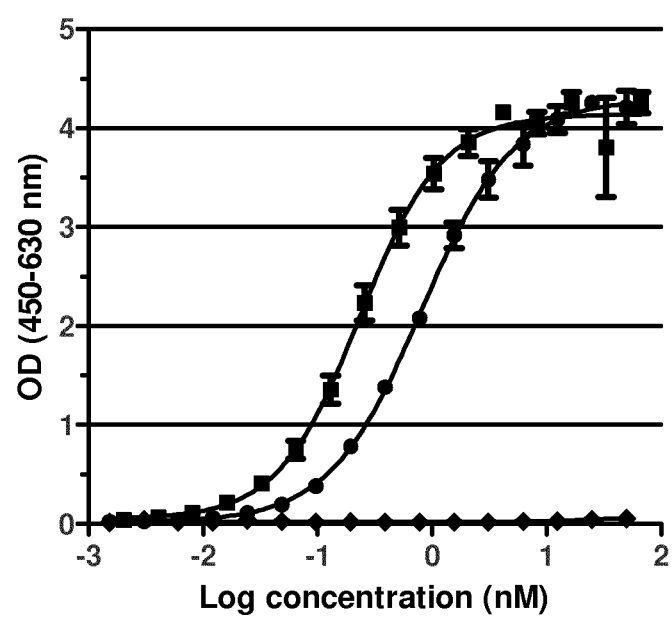
FIG. 9 shows binding curves of antibodies to TNFα. The closed circle represents a SIgA of the invention having infliximab variable regions, square represents infliximab, and diamond represents colostral secretory IgA.

For detection, the wells were incubated with TMB (Tebu Bio), 10 minutes at room temperature, 100 μl/well. The reaction was stopped with 0.3 M sulphuric acid, 100 μl/well, and the OD at 450 nm was measured with well correction at 630 nm. Measurement of IIB-SA1 from expression in mammalian cells (Example 2b) showed strong TNF-α affinity at a level comparable to that of infliximab as shown in FIG. 9. Note that the closed circle represents the SIgA of the invention (IIB-SA1), square represents Infliximab, and diamond represents Colostral SIgA. Equilibrium constants of $8.1 \times 10^{-10}$ and $2.4 \times 10^{-10}$ for IIB-SA1 and for Infliximab itself (REMICADE®), respectively, were calculated. This shows that the transfer of the TNF-α binding variable part of IgG1 antibody infliximab to a secretory IgA does not substantially alter affinity (taking the variation and discriminatory power of the experimental setup into account), and that the obtained product is fully functional.

Example 7

Proteolytic Stability of Anti-TNF-α SIgAs (IIB-SA1 and ADB-SA1g)

The stability of IIB-SA1 (Example 3b), and of ADB-SA1g (Example 4, from SynB03) was determined in simulated intestinal fluid (SIF, 0.05M phosphate buffer pH 6.8 containing 10 mg/ml pancreatin). Stability was compared to a human colostral SIgA which was purified to contain only kappa light chains and α-1 heavy chains.

Figure 10:
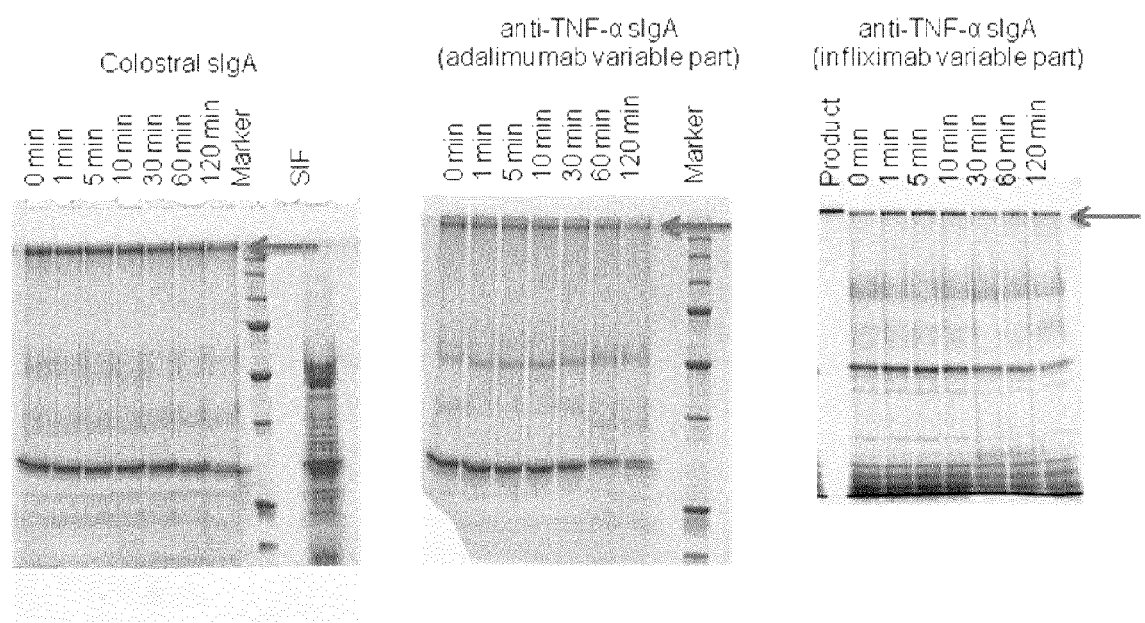
FIG. 10 shows the degradation of an anti-TNFα SIgA according to the invention having infliximab variable regions and being produced in mammalian cells, and an anti-TNFα SIgA according to the invention having adalimumab variable regions and being produced in *Lemna*, compared to colostral SIgA in simulated intestinal fluid (SIF).

150 μl of a 0.14 mg/ml solution of the material to be tested (i.e., IIB-SA1, ADB-SA1g, or human colostral SIgA (kappa light chain, α-1 heavy chain) was added to 550 μl of pre-heated SIF at 37° C. 100 μl samples were drawn at T=0, 5, 15, 30, 60 and 120 min, added to 25 ul protease inhibitor cocktail (Roche, 1169749800) followed by immediate freezing in liquid nitrogen. Samples were analyzed by non-reducing SDS-Page gel electrophoresis. Briefly; 57.5 μl of a 0.08 M solution of iodoacetamide in LDS sample buffer was added to each of the frozen samples. Samples were thawed and applied to Criterion Tris-HCl gel (12.5%, 18 well, 30 μl comb (Biorad, 345-0015). After electrophoresis gels were treated with Krypton protein stain and analyzed. Stability of the samples was qualitatively assessed visually. Results are shown in FIG. 10.

The two forms of anti-TNF-α SIgA, i.e., IIB-SA1 (labeled as infliximab variable part in FIG. 10) and ADB-SA1g (labeled as adalimumab variable part in FIG. 10) each showed a stability which was slightly less than that of the colostral SIgA.

Example 8a

Caco-2 Cell Based Assays

The aims of Caco-2 cell experiments were: (a) to evaluate in vitro the capacity of anti-TNF-α SIgA's to block the biological activity of TNF-α and (b) to study transport over an epithelial cell monolayer.

Caco-2 Cell Culture Conditions and Exposure to TNF-α

Human colonic adenocarcinoma epithelial Caco-2 cells (HTB 37, American Type Tissue Collection) were grown in C-DMEM consisting of DMEM-Glutamax (Life Technologies) supplemented with 10% fetal calf serum (FCS), 1% non essential amino acids, 10 mM HEPES, 0.1% transferrin and 1% streptomycin/penicillin Cells cultivated to 80% confluency were seeded on Snapwell filters (diameter, 12 mm; pore size, 0.4 mm; Corning Costar) at a density of $0.4 \times 10^5$ cells/cm$^2$. The formation of a polarized Caco-2 cell monolayer at week 3 was established by morphology (laser scanning confocal microscopy) and monitoring of the transepithelial electrical resistance (TER; 300-350 Ω×cm$^2$) using a Millicell-ERS apparatus (Millipore). After formation of the Caco-2 cell monolayer, the apical compartment medium was replaced by culture medium lacking FCS. One hour later, the medium lacking FCS was then replaced by medium containing 10 or 20 ng/ml of TNF-α, The polarized Caco-2 cell monolayers were sensitized with the TNF-α for 28 hours and the integrity of the monolayer was monitored by measurement of the TER.

Effect of SIgA's on Polarized Caco-2 Cell Monolayer Sensitized by TNF-α Applied Apically Caco-2 cell monolayers were established as described above. For each Snapwell insert, 10 ng TNF-α was mixed with an equimolar, or a 10-fold molar excess, of an antibody IIB-SA1 or ADB-SA1g to a final volume of 40 microliters phosphate-buffered saline (PBS). The TNF and antibody mixture was incubated for 20 minutes at ambient temperature followed by dilution with 460 microliters of culture medium lacking FCS. The medium in the apical compartment was replaced by the TNF and antibody mixture. The Caco-2 cell monolayers were sensitized for 28 hours and the integrity of the monolayer was monitored by measurement of the TER.

Figure 11:
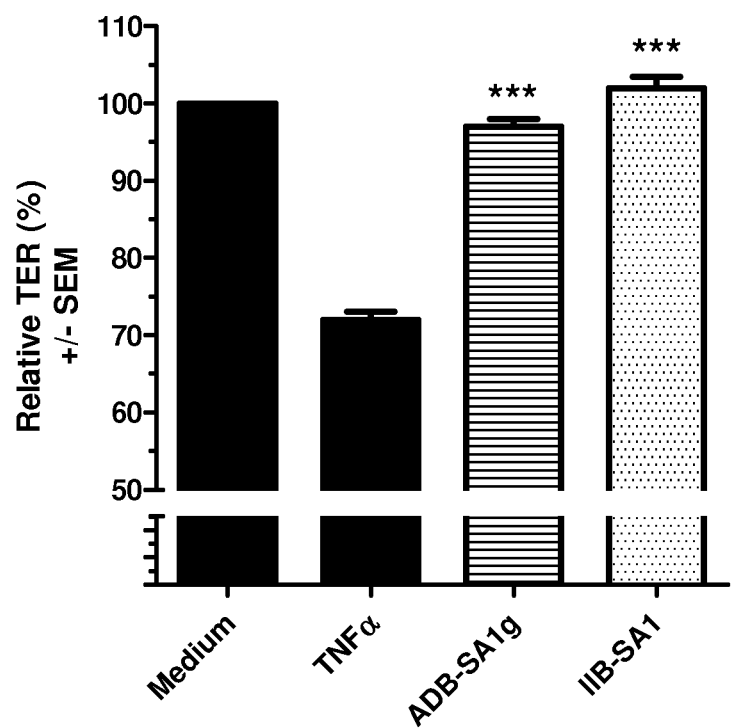
FIG. 11 shows TNFα-induced disturbance of Caco-2 monolayer integrity as measured by transepithelial electrical resistance (TER).

Results:

As shown in FIG. 11 for the 10-fold molar excess assay, taking the medium condition as 100%, the drop in TER values induced by TNF-α could be completely compensated by the presence of either anti-TNF-α SIgA preparation. The data are a mean of 6 independent replicates for each condition. Statistical analysis using ANOVA followed by Dunnett's Multiple Comparison test found a p<0.001 for the ADB-SA1g and IIB-SA1 results (indicated with *** in FIG. 11).

Effect of SIgA's on Polarized Caco-2 Cell Monolayer Sensitized by TNF-α Applied Apically: Possible Recovery after Apical Delivery.

Polarized Caco-2 cell monolayers were established as described above. The medium in the apical compartment was replaced by 20 ng/ml TNF-α as indicated above, and the polarized Caco-2 cell monolayers were sensitized for respectively 15 or 28 hours prior to addition of SIgA's (specifically IIB-SA1 or ADB-SA1g). After sensitization, Caco-2 cell were exposed to SIgA's for 24 hours and TER was monitored.

Figure 12:
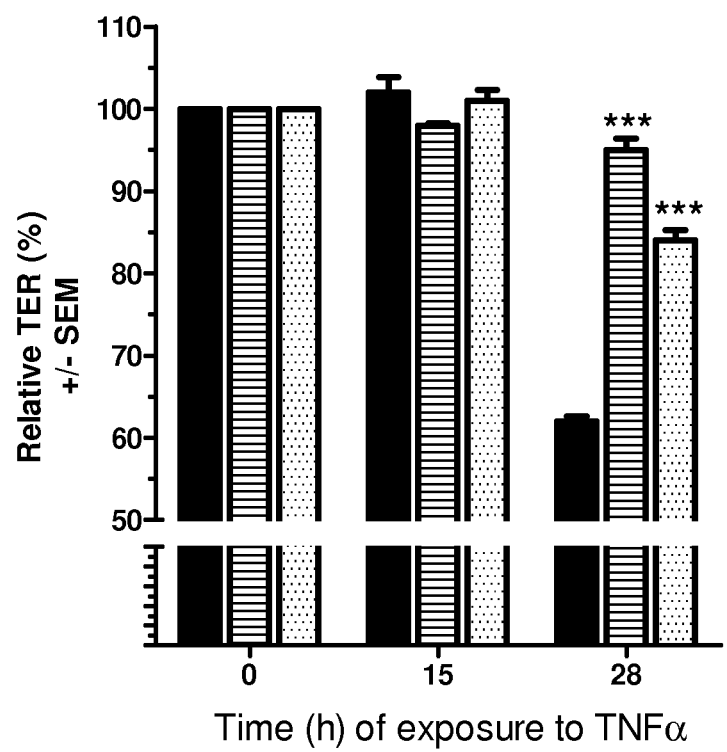
FIG. 12 shows the restoration of TNFα-induced disturbance of Caco-2 monolayer integrity as measured by TER.

Results:

The results are shown in FIG. 12. Black bars represent exposure to TNF-α only, striped bars represent addition of ADB-SA1g after indicated time of exposure to TNF-α, dotted bars represent addition of IIB-SA1 after indicated time of exposure to TNF-α. Statistical analysis using ANOVA followed by Dunnett's Multiple Comparison test, ADB-SA1g and IIB-SA1 were compared to TNF-α and had a p<0.001 (indicated by *** in FIG. 12). Data are means of 4 independent replicates Snapwell inserts for each condition. As expected, no effect was seen when adding the SIgA compounds at t=15 h, a time-point when the TER is not yet affected. At a later time-point (28 hours), which is known to dramatically affect TER (see e.g., Dongmei Ye, et al., *Am J Physiol Gastrointest Liver Physiol* 290: pp 496-504, 2006), application of the SIgA compound in the apical compartment resulted in marked recovery of the TER measured 24 hours later.

Conclusion:

These data suggests that delayed apical neutralization of the effect of TNF-α on polarized Caco-2 cell monolayers can lead to recovery, as long as the SIgA's are delivered within 28 hours post-cytokine exposure.

Tracking of the Bio-Availability of Fluorescent ADB-SA1g Applied in the Apical Compartment of Polarized Caco-2 Cell Monolayers ADB-SA1g was labeled with indocyanine Cy5 using the antibody labeling kit (General Electrics Healthcare), following the procedure provided by the kit's manufacturer. One microgram of labeled ADB-SA1g diluted in 500 microliters of FCS-free Caco-2 cell culture medium was added to the apical compartment and incubated overnight. Snapwell inserts were washed twice with PBS prior to fixation overnight with 5 ml of 4% paraformaldehyde at 4° C. After washing with PBS, filters were permeabilized with 0.2% Triton X-100, and non-specific binding sites were blocked with 5% FCS in PBS. Inserts were incubated with rabbit anti-human zonula occludens-1 (ZO-1) (1/200 dilution), washed in PBS prior to addition of secondary Ab (goat anti-rabbit IgG conjugated with Alexa Fluor 647; 1/100 dilution). After PBS washing, filters were then incubated with 4',6-diamidino-2-phenylindole (DAPI) at a concentration of 100 ng/ml in PBS (Invitrogen) for 30 min. Filters were recovered from their holders, and mounted in Vectashield (Vector Laboratories) for observation using a Zeiss LSM 710 Meta confocal microscope (Carl Zeiss, Germany) equipped with a 40× objective (Cellular Imaging Facility platform, Lausanne University, Switzerland) and processed using Zeiss ZEN 2009 light software.

Results:

Because 3D image reconstitution does not allow to finely pinpoint the location of the SIgA in contact with the Caco-2 cell monolayer, reliable tracking was carried out by analyzing successive confocal plans. Cell sections were selected at the bottom of microvilli, at the level of tight junctions, in the nuclear periphery, and at the level of the nucleus. Proper visualization was ensured by simultaneous staining with anti-ZO-1 antibodies and DAPI. ADB-SA1g was localized on the cell surface. The antibody was detected in the form of dense fluorescent spots within the cell cytosol, most likely in endocytotic/micropinocytic compartments.

Conclusion:

This indicates that intracellular distribution may serve as second line of defense and that ADB-SA1g could eventually neutralize internalized TNF-α.

Example 8b

Localization of Anti-TNF SIgA ADB-SA1g in In-Vivo Animal Models of IBD

In an animal model of IBD, disease was induced in female C57Bl/6 mice, 8 weeks of age, by topical sensibilization (day 1) with 0.5% TNBS in acetonitril (4:1), followed by a rectal challenge of 2.5% TNBS in 100% Ethanol on day 4 Animals were treated orally 3 times with ADB-SA1g (100 µg/mouse): 2 days before topical sensibilization (day −1) and on day 1 and 4. At day 6, when disease symptoms became apparent, animals were sacrificed and distal colon was collected for histological analyses. Fresh frozen tissue was fixed in 4% paraformaldehyde and washed 3 times with wash buffer (1×PBS+2% BSA). Unspecific binding sites were blocked with protein block reagent, washed 3 times and incubated with primary antibody over night at 4° C. After 3 wash steps, tissue slides were incubated with secondary antibody for 4 hours at 4° C., washed 3 times and incubated with streptavidin-Alexa488 for 1 hour at 4° C. Finally tissue slides were mounted with Vectashield mounting medium. Primary antibodies used were: sc-20656 (human SC chain) rabbit (Santa Cruz) 1:200, CD31 (Dendritic cells) rat antibody (Biolegend) 1:200, CD326 (EpCam) rat antibody (Biolegend) 1:200, CD11c (Dendritic cells) arm.Hamster (Biolegend) 1:200 and M-cells ULEX-1: lectin-FITC directly conjugated (Sigma-Aldrich) 1:200. Secondary antibodies used were: donkey-anti-rabbit Dylight 549 nm (red) (Dianova) for sc-20565, goat-anti-rat biotin antibody (BD Pharmingen) 1:500+Streptavidin-Alexa488 nm (green) 1:200 for CD31 and CD326, and goat-anti-arm. Hamster biotin antibody (Caltag) 1:500+Streptavidin Alexa488 nm for CD11c.

Results:

To demonstrate the presence of ADB-SA1g, antibody sc-20656 was used. This antibody binds to the human secretory chain, but not to mouse secretory chain. Positive staining for ADB-SA1g was found in epithelial cells (positive for CD 326) and in dendritic cells (positive for CD11c+ and CD31+). Surprisingly, no co-localization of ADB-SA1g with M-cells was found under the above described experimental conditions.

Conclusion:

This data confirms the "tracking of the bio-availability" results from Example 8a and indicates that intracellular distribution may serve as second line of defense and that ADB-SA1g could eventually neutralize internalized TNF-α.

Example 9

Efficacy of Anti-TNF SIgA ADB-SA1g in In-Vivo Animal Models of IBD

C57BL/6 mice were pre-treated orally 5 times a week (not in weekend) with PBS control, ADB-SA1g (100 µg/mouse), or 3 times per week subcutaneous with Adalimumab (100 µg/mouse). Start of pre-treatment is t=0. At day t=7 mice were treated with 2% dextran sulfate sodium (DSS) in drinking water to induce inflammation symptoms in intestine. First signs of inflammation can be seen at day 10-12, together with declined body weight. With mini-endoscopic system an analysis of the status of disease was performed. Briefly, a mini-endoscope (1.9 mm outer diameter) was introduced via the anus and the colon was carefully inflated with an air pump. Endoscopic pictures obtained allow the monitoring and grading of inflammation. Thereafter, endoscopic scoring of five parameters from 0-3 (1; translucent structure, 2; granularity, 3; fibrin, 4; vascularity, and 5; stool) resulting in the overall score from 0 (no change) to 15 (severe colitis) was performed. Typically, after one week exposure to DSS the symptoms are so strong that mice need a resting period to recover. At day t=16 the experiment was terminated and clinical score analyzed.

Figure 13:
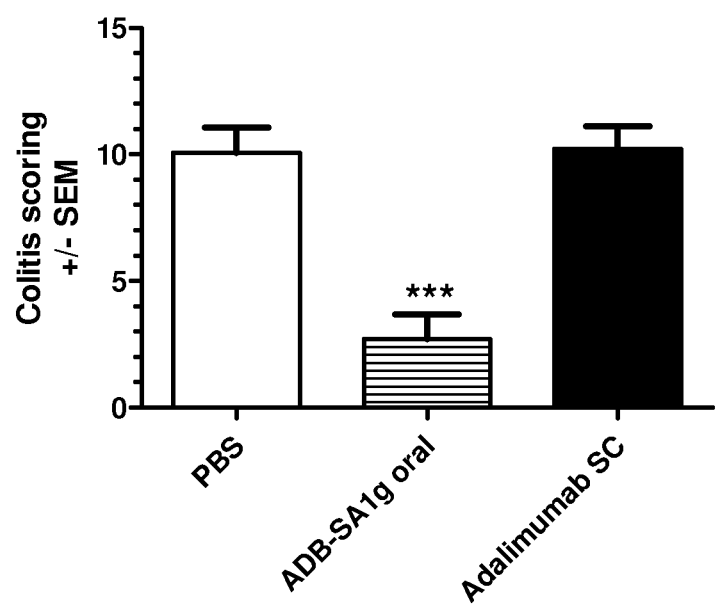
FIG. 13 represents the colitis scoring of DSS-induced inflammatory bowel disease in C57BL/6 mice with and without treatment.

The results are depicted in FIG. 13. Statistical analysis using ANOVA followed by Dunnett's Multiple Comparison test was performed comparing all groups to PBS control group. The ADB-SA1g was significant having a p<0.001 (indicated as *** in FIG. 13). n=7 mice per group. Oral treatment with ADB-SA1g significantly inhibited DSS-induced inflammatory bowel disease in C57BL/6 mice. In contrast, subcutaneous treatment with Adalimumab was not effective, even though both antibodies used the same binding head (variable region).

In FIG. 14 a representative mini-endoscopic picture of the colitis score at day t=15 is depicted.

Example 10

Efficacy of Anti-TNF SIgA ADB-SA1g in an In-Vivo Animal Model of RA

The therapeutic efficacy of oral ADB-SA1g was evaluated in a rheumatoid arthritis (RA) model based on a TNFα-overexpressing transgenic mouse model which spontaneously develops arthritis.

TNF driven spondylitis mouse (TNF$^{\Delta ARE/+}$) male mice (available via BiomedCode Hellas SA, heterozygous for the mouse TNFα mutation (maintained in a C57BL/6J genetic background) were crossed with C57BL/6J females. Their heterozygous offspring used in this study were identified by tail DNA genotyping which was further confirmed by the phenotype of these animals which exhibit a ruffled fur coat. Mixed sex mice were used in this study.

From the fourth week of age and onwards, the mice received daily (Monday-Friday) by oral gavage either drinking water, buffer (vehicle), ADB-SA1g (5 mg/kg), or subcutaneously every other day (Mon-Wed-Fri) etanercept (10 mg/kg).

Figure 15:
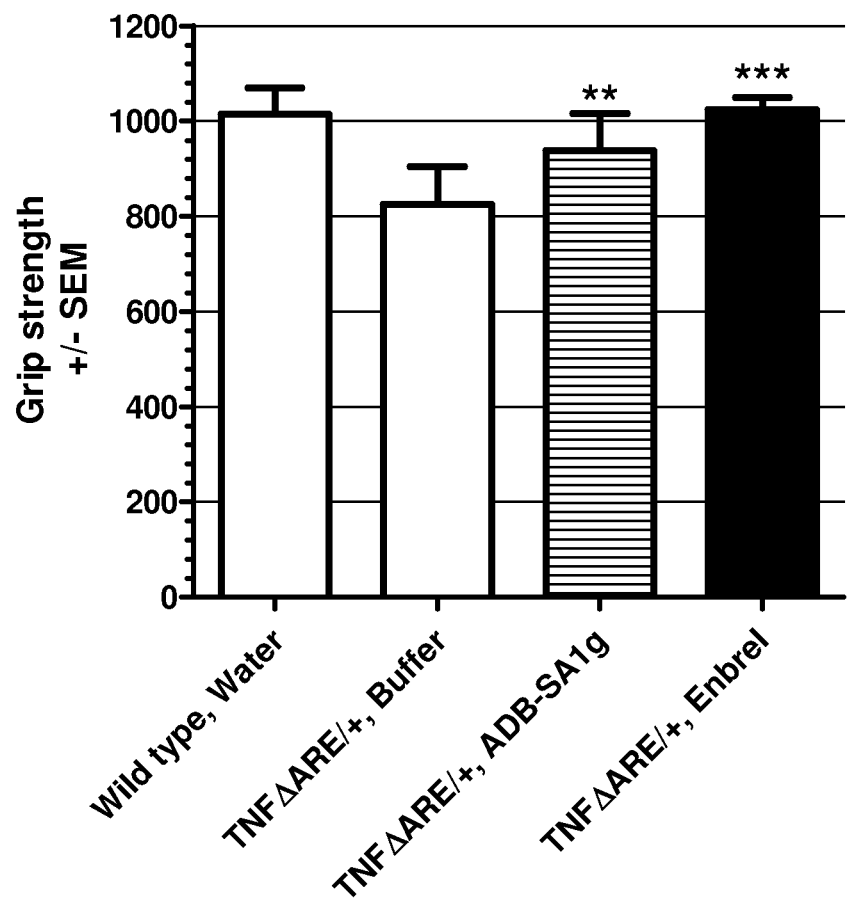
FIG. 15 shows the effects of subcutaneous application of etanercept and of oral application of ADB-SA1g on gripping strength of a transgenic TNFα-overexpressing mice that spontaneously develop arthritis ($TNF^{\Delta ARE/+}$-mice).

Body weight and grip strength measurements were recorded weekly for each mouse. All TNF$^{\Delta ARE/+}$ mice showed normal body weight gain when compared to wild-type littermate control mice. Statistical analysis using ANOVA followed by Newman-Keuls Multiple Comparison Test was performed comparing all groups to TNF$^{\Delta ARE/+}$ vehicle treated group (n=6-8 per group,  p<0.01, * p<0.001). At 11 weeks of age, the vehicle-treated TNF$^{\Delta ARE/+}$ mice displayed significantly reduced grip strength in comparison to wt littermate control mice and etanercept-treated TNF$^{\Delta ARE/+}$ mice. Mice treated orally with ADB-SA1g and mice treated subcutaneously with etanercept displayed comparable, statistically-significant increased grip strength (FIG. 15).

At 11 weeks of age, when the control TNF$^{\Delta ARE/+}$ group had obvious signs of arthritic pathology, mice from all groups were sacrificed and tissue samples from ankle joints were collected and processed for histopathological analysis. Ankle joints were assessed histopathologically. The hind joints of the TNF$^{\Delta ARE/+}$ mice were scored for synovial hyperplasia, existence of inflammatory foci, cartilage destruction, and bone erosion using the scoring scale detailed below:

0=normal
1=mild inflammation in periarticular tissue and/or mild oedema
2=moderate inflammation and pannus formation with superficial cartilage and bone destruction
3=marked inflammation with pannus formation and moderate cartilage and bone destruction (depth to middle zone)
4=severe inflammation with pannus formation and marked cartilage and bone destruction (depth to tidemark).

Figure 16:
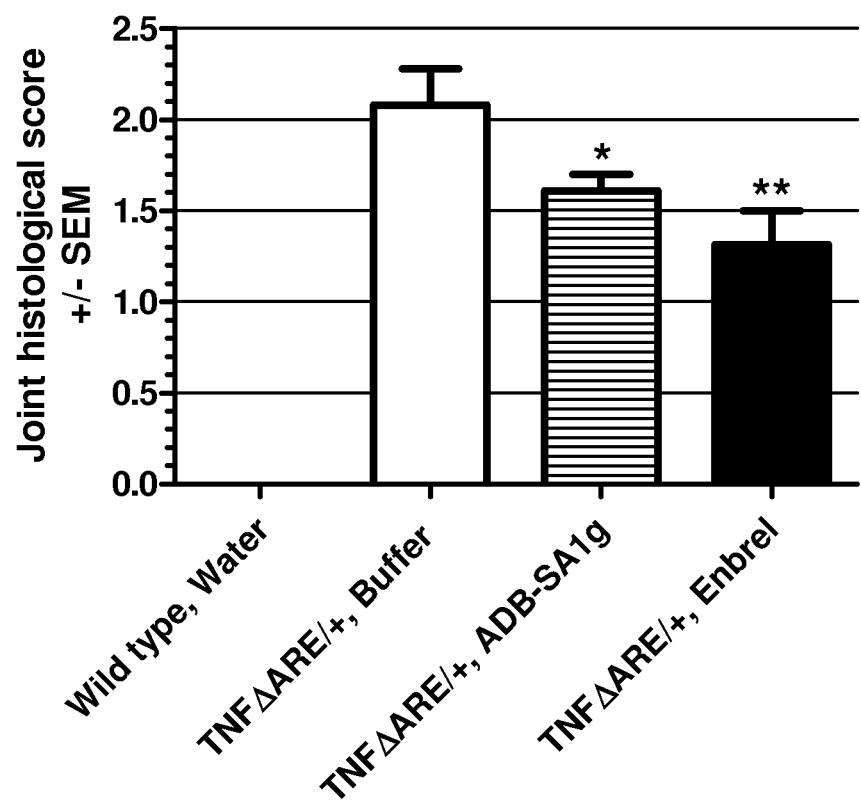
FIG. 16 shows the effects of subcutaneous application of etancercept and of oral application of ADB-SA1g on arthritic score of hind paws of transgenic TNFα-overexpressing mice which spontaneously develop arthritis ($TNF^{\Delta ARE}$-mice).

Histopathological analysis of the ankle joints revealed that the vehicle treated TNF$^{\Delta ARE/+}$ mice displayed severe signs of arthritis. Statistical analysis using ANOVA followed by Newman-Keuls Multiple Comparison Test was performed comparing all groups to TNF$^{\Delta ARE/+}$ vehicle treated group (n=6-8 per group, * p<0.05, ** p, 0.01). Etanercept-treated animals displayed significantly decreased signs of pathology. Mice treated orally with ADB-SA1g also showed decreased joint inflammation when compared to vehicle-treated TNF$^{\Delta ARE/+}$ mice with an effect comparable to sc etanercept treated animals (FIG. 16).

Each of the patents, patent applications, and journal articles mentioned above are incorporated herein by reference in their entirety. The invention having been described it will be obvious that the same may be varied in many ways and all such modifications are contemplated as being within the scope of the invention as defined by the claims appended hereto.

The invention claimed is:

1. A monoclonal secretory IgA antibody, which binds to and neutralizes human TNFα, wherein said antibody comprises:
   (a) a heavy chain constant region having a sequence selected from the group consisting of SEQ ID NO:10, SEQ ID NO:11, SEQ ID NO:12 and SEQ ID NO:13, a heavy chain variable region having the sequence of SEQ ID NO:2, and a light chain variable region having the sequence of SEQ ID NO:3; or
   (b) a heavy chain constant region having a sequence selected from the group consisting of SEQ ID NO:10, SEQ ID NO:11, SEQ ID NO:12 and SEQ ID NO:13, a heavy chain variable region having the sequence of SEQ ID NO:4, and a light chain variable region having the sequence of SEQ ID NO: 5.

2. The antibody according to claim 1, wherein said antibody comprises a human secretory chain having the sequence of SEQ ID NO:21.

3. The antibody according to claim 1, wherein said antibody comprises a human J-chain having the sequence of SEQ ID NO:20.

4. The antibody according to claim 1, wherein said antibody contains the light chain variable region having the sequence of SEQ ID NO:5 and inhibits the proinflammatory effect of a human TNFα by at least 50%.

5. The antibody according to claim 4, wherein said antibody contains the light chain variable region having the sequence of SEQ ID NO:5 and inhibits the proinflammatory effect of a human TNFα by at least 98%.

6. A monoclonal secretory IgA antibody, which binds to and neutralizes human TNFα, wherein said antibody comprises:
   (a) a heavy chain constant region having a sequence selected from the group consisting of SEQ ID NO:10, SEQ ID NO:11, SEQ ID NO:12 and SEQ ID NO:13, or minor variations thereof, a heavy chain variable region having the sequence of SEQ ID NO:2, and a light chain variable region having the sequence of SEQ ID NO:3; or
   (b) a heavy chain constant region having a sequence selected from the group consisting of SEQ ID NO:10, SEQ ID NO:11, SEQ ID NO:12 and SEQ ID NO:13, or minor variations thereof, a heavy chain variable region having the sequence of SEQ ID NO:4, and a light chain variable region having the sequence of SEQ ID NO: 5; and
   wherein the minor variations are no more than 10 conservative amino acid additions, deletions, or substitutions.

7. A monoclonal secretory IgA antibody, which binds to and neutralizes human TNFα, wherein said antibody comprises:
   (a) a heavy chain constant region having a sequence selected from the group consisting of SEQ ID NO:10, SEQ ID NO:11, SEQ ID NO:12 and SEQ ID NO:13, or minor variations thereof, a heavy chain variable region having the sequence of SEQ ID NO:2, and a light chain variable region having the sequence of SEQ ID NO:3; or
   (b) a heavy chain constant region having a sequence selected from the group consisting of SEQ ID NO:10, SEQ ID NO:11, SEQ ID NO:12 and SEQ ID NO:13, or minor variations thereof, a heavy chain variable region having the sequence of SEQ ID NO:4, and a light chain variable region having the sequence of SEQ ID NO: 5; and
   (c) a human secretory chain having the sequence of SEQ ID NO:21, or minor variations thereof, wherein the minor variations are no more than 10 conservative amino acid additions, deletions, or substitutions, and
   wherein said amino acid insertions, substitutions, or deletions do not significantly alter the ability of the secretory chain to stabilize secretory IgA proteolysis.

8. A monoclonal secretory IgA antibody, which binds to and neutralizes human TNFα, wherein said antibody comprises:
   (a) a heavy chain constant region having a sequence selected from the group consisting of SEQ ID NO:10, SEQ ID NO:11, SEQ ID NO:12 and SEQ ID NO:13, or minor variations thereof, a heavy chain variable region having the sequence of SEQ ID NO:2, and a light chain variable region having the sequence of SEQ ID NO:3; or
   (b) a heavy chain constant region having a sequence selected from the group consisting of SEQ ID NO:10, SEQ ID NO:11, SEQ ID NO:12 and SEQ ID NO:13, or minor variations thereof, a heavy chain variable region having the sequence of SEQ ID NO:4, and a light chain variable region having the sequence of SEQ ID NO: 5; and
   (c) a human J-chain having the sequence of SEQ ID NO:20, or minor variations thereof, wherein the minor variations are no more than 10 conservative amino acid additions, deletions, or substitutions, and
   wherein said amino acid insertions, substitutions, or deletions do not significantly alter the ability of the J-chain to join two monomeric IgA antibodies to form a dimer and to enable attachment of the secretory chain.

9. A pharmaceutical composition comprising a therapeutically effective amount of a monoclonal secretory IgA antibody, which binds to and neutralizes human TNFα, wherein said antibody comprises:
   (a) a heavy chain constant region having a sequence selected from the group consisting of SEQ ID NO:10, SEQ ID NO:11, SEQ ID NO:12 and SEQ ID NO:13, a heavy chain variable region having the sequence of SEQ ID NO:2, and a light chain variable region having the sequence of SEQ ID NO:3; and or (b) a heavy chain constant region having a sequence selected from the group consisting of SEQ ID NO:10, SEQ ID NO:11, SEQ ID NO:12 and SEQ ID NO:13, a heavy chain variable region having the sequence of SEQ ID NO:4, and a light chain variable region having the sequence of SEQ ID NO: 5, and at least one pharmaceutically acceptable excipient.

10. The composition of claim 9, wherein the composition comprises about 0.01 to 1000 mg of the antibody.

11. The composition of claim 9, wherein the composition comprises a plurality of secretory IgA antibodies.

12. The composition of claim 11, wherein said plurality of secretory IgA antibodies contains at least about 30% G0 glycans.

13. The composition of claim 12, wherein said G0 glycans lack fucose and xylose residues.

14. The composition of claim 9, wherein said plurality of secretory IgA antibodies contains at least about 25% high-mannose glycans.

15. The composition of claim 14, wherein said high-mannose glycans are selected from the group consisting of Man5, Man6, Man7, Man8, and Man9.

16. The composition of claim 11, wherein said plurality of secretory IgA antibodies contains at least 70% of G0 glycans and high-mannose glycans relative to the total amount of N-glycans in the plurality of secretory IgA antibodies.

17. The composition of claim 9, wherein the composition can be administered to a human by oral, rectal, buccal, topical, systemic, subcutaneous, or ophthalmic administration.

18. The composition of claim 9, wherein the composition comprises less than 10% of dimer IgA and monomer IgA.

19. A method for treating an inflammatory disease or skin disorder in a human, which comprises administering an anti-inflammatory effective amount of a monoclonal secretory IgA antibody which binds to and neutralizes human TNFα, wherein said antibody comprises:

(a) a heavy chain constant region having a sequence selected from the group consisting of SEQ ID NO:10, SEQ ID NO:11, SEQ ID NO:12 and SEQ ID NO:13, a heavy chain variable region having the sequence of SEQ ID NO:2, and a light chain variable region having the sequence of SEQ ID NO:3; or (b) a heavy chain constant region having a sequence selected from the group consisting of SEQ ID NO:10, SEQ ID NO:11, SEQ ID NO:12 and SEQ ID NO:13, a heavy chain variable region having the sequence of SEQ ID NO:4, and a light chain variable region having the sequence of SEQ ID NO: 5.

20. The method according to claim 19, wherein said administering is oral, rectal, buccal, topical, systemic, subcutaneous, or ophthalmic.

21. The method according to claim 20, wherein said disease or disorder is selected from the group consisting of inflammatory bowel disease, ulcerative colitis, Crohn's disease, rheumatoid arthritis, psoriasis, psoriatic arthritis, ankylosing spondylitis, juvenile idiopathic arthritis, uveitis, asthma, Alzheimer's disease, acne ectopica, oral aphtha, bullous and cicatricial pemphigoid, mucocutaneous symptoms of Behcet's Disease, dermatomyositis, erythema annulare centrifugum, skin manifestations of graft-versus-host disease, non-infectious granulomatous skin disease, granuloma annulare, granuloma cheilitis, granulomatous rosacea, and inflammation or disorders of the eye.

\* \* \* \* \*